US009853222B2

(12) United States Patent
Kim et al.

(10) Patent No.: US 9,853,222 B2
(45) Date of Patent: Dec. 26, 2017

(54) CONDENSED-CYCLIC COMPOUND AND ORGANIC LIGHT-EMITTING DIODE COMPRISING THE SAME

(71) Applicant: Samsung Display Co., LTD., Yongin, Gyeonggi-do (KR)

(72) Inventors: Se-Hun Kim, Yongin (KR); Mi-Kyung Kim, Yongin (KR); Kwan-Hee Lee, Yongin (KR); Chang-Woong Chu, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 434 days.

(21) Appl. No.: 13/973,831

(22) Filed: Aug. 22, 2013

(65) Prior Publication Data

US 2014/0291628 A1 Oct. 2, 2014

(30) Foreign Application Priority Data

Mar. 27, 2013 (KR) ........................ 10-2013-0033083

(51) Int. Cl.
*H01L 51/50* (2006.01)
*H01L 51/00* (2006.01)
(Continued)

(52) U.S. Cl.
CPC ........ *H01L 51/0072* (2013.01); *C07D 471/16* (2013.01); *C07D 491/16* (2013.01);
(Continued)

(58) Field of Classification Search
None
See application file for complete search history.

(56) References Cited

U.S. PATENT DOCUMENTS

2010/0032658 A1 2/2010 Lee et al.
2013/0026422 A1* 1/2013 Parham ................ C07D 471/06 252/500

FOREIGN PATENT DOCUMENTS

KR 10-2010-0007780 A 1/2010
KR 10-2010-0105099 A 9/2010
(Continued)

*Primary Examiner* — Gregory Clark
(74) *Attorney, Agent, or Firm* — Lewis Roca Rothgerber Christie LLP

(57) ABSTRACT

A condensed-cyclic compound is represented by Formula 1, and an organic light-emitting diode includes the condensed-cyclic compound. The organic light-emitting diode includes a first electrode, a second electrode facing the first electrode, and an organic layer. The organic layer includes an emission layer and the condensed-cyclic compound. The condensed-cyclic compound can be included in the emission layer as a host, and the emission layer may further include a dopant.

Formula 1

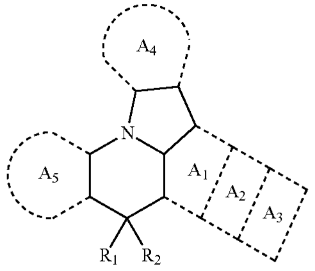

21 Claims, 1 Drawing Sheet

(51) Int. Cl.

| | |
|---|---|
| ***C07D 471/16*** | (2006.01) |
| ***C07D 491/16*** | (2006.01) |
| ***C07D 495/16*** | (2006.01) |
| ***C09K 11/06*** | (2006.01) |
| ***C09B 57/00*** | (2006.01) |

(52) U.S. Cl.

CPC ............ *C07D 495/16* (2013.01); *C09B 57/00* (2013.01); *C09K 11/06* (2013.01); *H01L 51/0061* (2013.01); *H01L 51/0067* (2013.01); *H01L 51/0071* (2013.01); *C09K 2211/1007* (2013.01); *C09K 2211/1011* (2013.01); *C09K 2211/1033* (2013.01); *C09K 2211/1037* (2013.01); *C09K 2211/1044* (2013.01); *C09K 2211/1059* (2013.01); *H01L 51/0077* (2013.01); *H01L 51/0081* (2013.01); *H01L 51/0085* (2013.01); *H01L 51/5016* (2013.01)

(56) References Cited

FOREIGN PATENT DOCUMENTS

| | | | |
|---|---|---|---|
| KR | 10-2011-0066763 | A | 6/2011 |
| KR | 10-2011-0113470 | A | 10/2011 |
| KR | 10-2011-0117547 | A | 10/2011 |
| WO | WO 2010/107244 | A2 | 9/2010 |

* cited by examiner

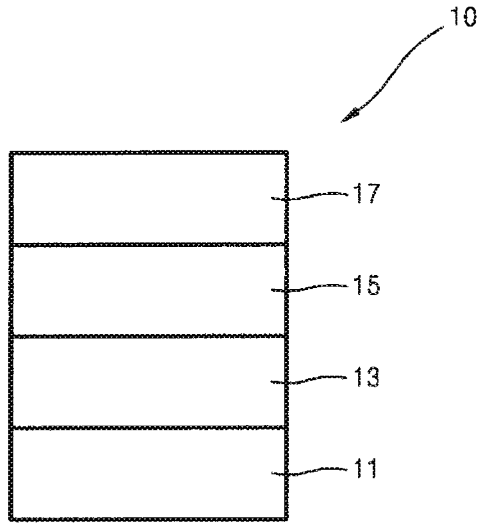
10
17
15
13
11

CONDENSED-CYCLIC COMPOUND AND ORGANIC LIGHT-EMITTING DIODE COMPRISING THE SAME

CROSS-REFERENCE TO RELATED APPLICATION

This application claims priority to and the benefit of Korean Patent Application No. 10-2013-0033083, filed on Mar. 27, 2013 in the Korean Intellectual Property Office, the entire content of which is incorporated herein by reference.

BACKGROUND

1. Technical Field

Embodiments of the present invention relate to compounds for organic light-emitting diodes and to organic light-emitting diodes including the same.

2. Description of the Related Art

Organic light-emitting diodes (OLEDs) are self-emitting devices having advantages such as wide viewing angles, good contrast, quick response speeds, high brightness, and good driving voltage characteristics. Also, OLEDs can provide multicolored images.

A typical organic light-emitting diode structure includes a substrate, and an anode, a hole transport layer (HTL), an emission layer (EML), an electron transport layer (ETL), and a cathode sequentially stacked on the substrate. The HTL, the EML, and the ETL are organic thin films formed of organic compounds.

An operating principle of a typical organic light-emitting diode having the above-described structure is as follows. When a voltage is applied between the anode and the cathode, holes injected from the anode move to the EML via the HTL, and electrons injected from the cathode move to the EML via the ETL. Carriers, such as the holes and electrons, recombine in the EML to generate excitons. When the excitons drop from an excited state to a ground state, light is emitted.

SUMMARY

Embodiments of the present invention are directed to compounds for organic light-emitting diodes and to organic light-emitting diodes including the same.

According to an aspect of the present invention, a condensed-cyclic compound is represented by Formula 1 below.

Formula 1

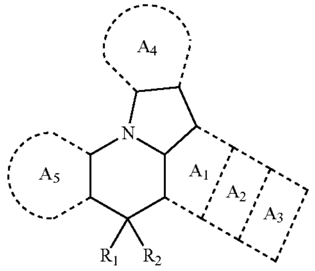

Formula 2

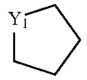

In Formula 1, ring $A_1$, ring $A_2$, and ring $A_3$ are condensed with each other. Ring $A_2$ is represented by Formula 2 above, in which $Y_1$ is O, S, or N-$(L_1)_{aa}$-$(R_{11})_{ab}$. Ring $A_1$, ring $A_3$, ring $A_4$, and ring $A_5$ are each independently a substituted or unsubstituted benzene ring or a substituted or unsubstituted naphthalene ring.

$R_1$ and $R_2$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group. $R_1$ and $R_2$ are non-ring forming substituents which are not linked to each other and do not form a ring.

$L_1$ is a substituted or unsubstituted $C_6$-$C_{60}$ arylene group or a substituted or unsubstituted $C_2$-$C_{60}$ heteroarylene group.

aa is an integer from 0 to 5.

$R_{11}$ is a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, or a substituted or unsubstituted $C_2$-$C_{60}$ heteroaryl group.

ab is an integer from 1 to 10.

According to another aspect of the present invention, an organic light-emitting diode includes: a first electrode; a second electrode facing the first electrode; and an organic layer between the first electrode and the second electrode and including an emission layer. The organic layer includes at least one condensed-cyclic compound.

BRIEF DESCRIPTION OF THE DRAWINGS

The above and other features and advantages of the present invention will become more apparent by reference to the following detailed description when considered in conjunction with the attached drawing, in which:

FIG. 1 is a schematic cross-sectional view of an organic light-emitting diode according to an embodiment of the present invention.

DETAILED DESCRIPTION

Hereinafter, embodiments of the present invention will be described with reference to the accompanying drawings, in which exemplary embodiments of the invention are shown.

As used herein, the term "and/or" includes any and all combinations of one or more of the associated listed items. Expressions such as "at least one of," when preceding a list of elements, modify the entire list of elements and do not modify the individual elements of the list.

A condensed-cyclic compound according to an embodiment of the present invention is represented by Formula 1 below.

Formula 1

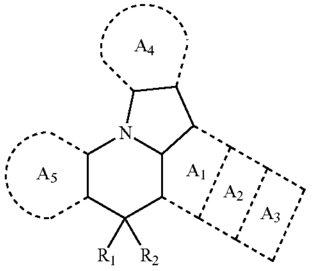

In Formula 1, ring $A_1$, ring $A_2$, and ring $A_3$ are condensed with each other. Each of ring $A_1$, ring $A_4$, and ring $A_5$ are condensed with a neighboring ring.

In Formula 1, the ring $A_2$ is represented by Formula 2 below. In Formula 2, $Y_1$ may be O, S, or $N-(L_1)_{aa}-(R_{11})_{ab}$. $L_1$, aa, $R_{11}$, and ab will be described later.

Formula 2

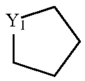

In Formula 1, ring $A_1$, ring $A_3$, ring $A_4$, and ring $A_5$ may each independently be a substituted or unsubstituted benzene ring or a substituted or unsubstituted naphthalene ring.

In Formula 1, ring $A_1$, ring $A_2$, ring $A_3$, ring $A_4$, and ring $A_5$ may have various structures depending on their condensation methods.

For example, the compound of Formula 1 may be represented by Formula 3 or 4 according to a condensation method of the ring $A_2$.

Formula 3

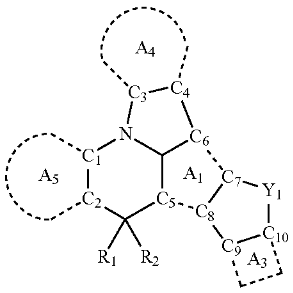

Formula 4

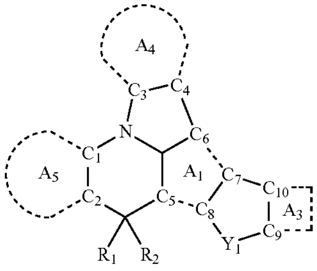

In Formulae 3 and 4, $C_1$ to $C_{10}$ indicate chemically distinct carbon atoms.

In Formulae 3 and 4, the ring $A_1$ may be represented by one of Formulae 5(1) and 5(2).

Formula 5(1)

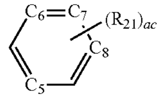

Formula 5(2)

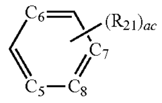

In Formulae 5(1) and 5(2), ac may be 1 or 2. If ac is 2, the two $R_{21}$s may be the same or different.

In Formulae 3 and 4, the ring $A_3$ may be represented by one of Formulae 6(1) to 6(4) below.

Formula 6(1)

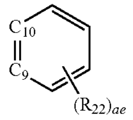

Formula 6(2)

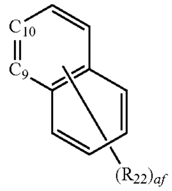

Formula 6(3)

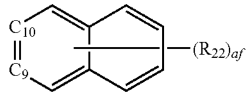

Formula 6(4)

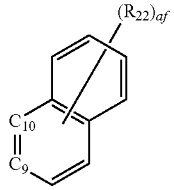

In Formulae 6(1) to 6(4), ae may be an integer from 1 to 4, and af may be an integer from 1 to 6. If ae is 2 or greater, the two or more $R_{22}$s may be the same or different. If af is 2 or greater, the two or more $R_{22}$s may be the same or different.

In Formulae 3 and 4, the ring $A_4$ may be represented by one of Formulae 7(1) to 7(4) below.

Formula 7(1)

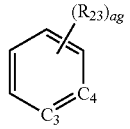

Formula 7(2)

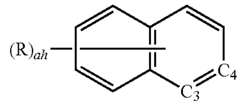

-continued

Formula 7(3)

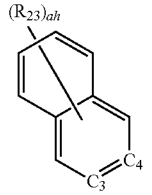

Formula 7(4)

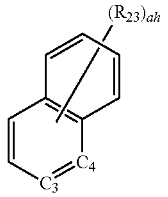

In Formulae 7(1) to 7(4), ag may be an integer from 1 to 3, and ah may be an integer from 1 to 5. If ag is 2 or greater, the two or more $R_{23}$s may be the same or different. If ah is 2 or greater, the two or more $R_{23}$s may be the same or different.

In Formulae 3 and 4, the ring $A_5$ may be represented by one of Formulae 8(1) to 8(4) below.

Formula 8(1)

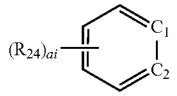

Formula 8(2)

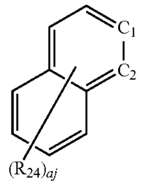

Formula 8(3)

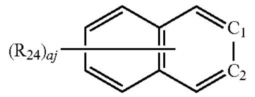

Formula 8(4)

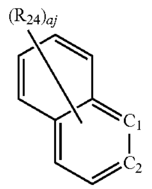

In Formulae 8(1) to 8(4), ai may be an integer from 1 to 4, and aj may be an integer from 1 to 7. If ai is 2 or greater, the two or more $R_{24}$s may be the same or different. If aj is 2 or greater, the two or more $R_{24}$s may be the same or different.

The locations of the carbon atoms represented as $C_1$ to $C_{10}$ in Formulae 5(1) and 5(2), 6(1) to 6(4), 7(1) to 7(4), and 8(1) to 8(4) are the same as those shown in Formulae 3 and 4.

In Formulae 5(1) and 5(2), 6(1) to 6(4), 7(1) to 7(4), and 8(1) to 8(4), $R_{21}$ to $R_{24}$ may each independently be a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or $-(L_2)_{ao}-(R_{12})_{ap}$. In $-(L_2)_{ao}-(R_{12})_{ap}$, $L_2$ may be a substituted or unsubstituted $C_6$-$C_{60}$ arylene group or a substituted or unsubstituted $C_2$-$C_{60}$ heteroarylene group. ao may be an integer from 0 to 5. $R_{12}$ may be a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, or a substituted or unsubstituted $C_2$-$C_{60}$ heteroaryl group. ap may be an integer from 1 to 10.

For example, $R_{21}$ to $R_{24}$ may each independently be:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group (e.g., a methyl group, an ethyl group, a propyl group, a butyl group, a pentyl group, a hexyl group, a heptyl group, or an octyl group) or a $C_1$-$C_{20}$ alkoxy group (e.g., a methoxy group, an ethoxy group, a propoxy group, a butoxy group, or a pentoxy group); or a $C_1$-$C_{20}$ alkyl group or a $C_1$-$C_{20}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a $C_6$-$C_{14}$ aryl group (e.g., a phenyl group, a naphthyl group, or an anthracenyl group) or a $C_2$-$C_{14}$ heteroaryl group (e.g., a pyridinyl group, a pyrimidinyl group, a pyrazinyl group, or a triazinyl group); or a $C_6$-$C_{14}$ aryl group or a $C_2$-$C_{14}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; or $-(L_2)_{ao}-(R_{12})_{ap}$. However, $R_{21}$ to $R_{24}$ are not limited to the above moieties.

$L_2$ may be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group.

ao may be selected from 0, 1, or 2.

$R_{12}$ may be a substituted or unsubstituted 5-membered hetero ring, a substituted or unsubstituted 6-membered hetero ring, a substituted or unsubstituted 9-membered hetero ring, or a substituted or unsubstituted 10-membered hetero ring, and includes at least one nitrogen (N) as a ring-forming atom.

ap may be 1 or 2.

According to another embodiment of the present invention, $R_{21}$ to $R_{24}$ may each independently be:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a hexyl group, a heptyl group, an octyl group, a methoxy group, an ethoxy group, a propoxy group, a butoxy group, or a pentoxy group; or a methyl group, an ethyl group, a propyl group, a butyl group, a pentyl group, a hexyl group, a heptyl group, an octyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a phenyl group, a naphthyl group, an anthracenyl group, a pyridinyl group, a pyrimidinyl group, a pyrazinyl group, or a triazinyl group; or a phenyl group, a naphthyl group, an anthracenyl group, a pyridinyl group, a pyrimidinyl group, a pyrazinyl group, or a triazinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; or $-(L_2)_{ao}-(R_{12})_{ap}$.

$L_2$ may be a phenylene group, a naphthylene group, a fluorenylene group, or an anthracenylene group; or a phenylene group, a naphthylene group, a fluorenylene group, or an anthracenylene group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

ao may be 0, 1, or 2.

$R_{12}$ may be a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

ap may be 1 or 2. However, $R_{21}$ to $R_{24}$ are not limited thereto.

According to an embodiment of the present invention, the condensed-cyclic compound may be represented by Formula 3, where the ring $A_1$ may be represented by one of Formulae 5(1) and 5(2). The moieties of Formulae 5(1) and 5(2) are described above.

According to another embodiment of the present invention, the condensed-cyclic compound may be represented by Formula 3, where the ring $A_1$ may be represented by one of Formulae 5(1) and 5(2), the ring $A_3$ may be represented by one of Formulae 6(1) and 6(2), the ring $A_4$ may be represented by one of Formulae 7(1) and 7(3), and the ring $A_5$ may be represented by one of Formulae 8(1) and 8(3), but the condensed-cyclic compound and the rings $A_1$, $A_3$, $A_4$ and $A_5$ are not limited thereto. The moieties of Formulae 5(1), 5(2), 6(1), 6(2), 7(1), 7(3), 8(1), and 8(3) are described above.

In Formula 2, $Y_1$ may be O, S, or $N-(L_1)_{aa}-(R_{11})_{ab}$. For example, in Formula 2, $Y_1$ may be $N-(L_1)_{aa}-(R_{11})_{ab}$. In $N-(L_1)_{aa}-(R_{11})_{ab}$, $L_1$ may be a substituted or unsubstituted $C_6$-$C_{60}$ arylene group or a substituted or unsubstituted $C_2$-$C_{60}$ heteroarylene group. For example, $L_1$ may be a substituted or unsubstituted $C_6$-$C_{60}$ arylene group.

According to some embodiments, for example, $L_1$ may be a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group.

For example, $L_1$ may be a substituted or unsubstituted phenylene group, a substituted or unsubstituted naphthylene group, a substituted or unsubstituted a fluorenylene group, a substituted or unsubstituted spiro-fluorenylene group, a substituted or unsubstituted anthracenylene group, or a substituted or unsubstituted pyrenylene group.

For example, $L_1$ may be a phenylene group, a naphthylene group, a fluorenylene group, a spiro-fluorenylene group, an anthracenylene group or a pyrenylene group; or a phenylene group, a naphthylene group, a fluorenylene group, a spiro-fluorenylene group, an anthracenylene group, or a pyrenylene group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl, a naphthyl group, or an anthracenyl group. However, $L_1$ is not limited thereto.

In N-$(L_1)_{aa}$-$(R_{11})_{ab}$, aa may be an integer from 0 to 5. For example, aa may be 0, 1, or 2. If aa is 2 or greater, the two or more $L_1$s may be the same or different.

In N-$(L_1)_{aa}$-$(R_{11})_{ab}$, $R_{11}$ may be a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, or a substituted or unsubstituted $C_2$-$C_{60}$ heteroaryl group.

For example, $R_{11}$ may be a substituted or unsubstituted $C_6$-$C_{14}$ aryl group or a substituted or unsubstituted $C_2$-$C_{60}$ heteroaryl group.

For example, $R_{11}$ may be a substituted or unsubstituted 5-membered hetero ring, a substituted or unsubstituted 6-membered hetero ring, a substituted or unsubstituted 9-membered hetero ring, or a substituted or unsubstituted 10-membered hetero ring that includes at least one nitrogen (N) as a ring-forming atom.

According to an embodiment, $R_{11}$ may be a substituted or unsubstituted pyrrolyl group, a substituted or unsubstituted pyrazolyl group, a substituted or unsubstituted imidazolyl group, a substituted or unsubstituted pyridinyl group, a substituted or unsubstituted pyrazinyl group, a substituted or unsubstituted pyrimidinyl group, a substituted or unsubstituted indolyl group, a substituted or unsubstituted purinyl group, a substituted or unsubstituted benzoimidazolyl group, a substituted or unsubstituted quinolinyl group, or a substituted or unsubstituted isoquinolinyl group.

For example, $R_{11}$ may be:

a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group. However, $R_{11}$ is not limited thereto.

In N-$(L_1)_{aa}$-$(R_{11})_{ab}$, $R_{11}$ may be represented by one of Formulae 9 to 15 below.

Formula 9

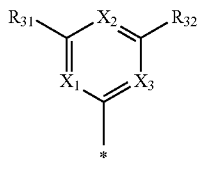

-continued

Formula 10

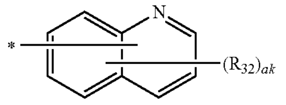

Formula 11

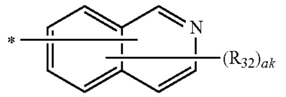

Formula 12

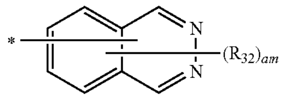

Formula 13

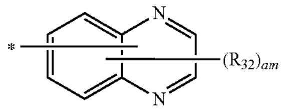

Formula 14

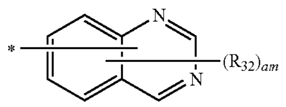

Formula 15

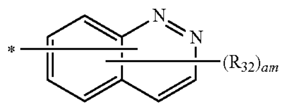

In Formulae 9 to 15, $X_1$ may N or $C(R_{33})$, $X_2$ may be N or $C(R_{34})$, and $X_3$ may be N or $C(R_{35})$. At least one of $X_1$, $X_2$, and $X_3$ may be N.

$R_{31}$ to $R_{35}$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

ak may be an integer from 1 to 6.

am may be an integer from 1 to 5.

* may be a binding site to $L_1$ or nitrogen in $Y_1$.

In Formula 9, $X_1$ may N or $C(R_{33})$, $X_2$ may be N or $C(R_{34})$, and $X_3$ may be N or $C(R_{35})$. At least one of $X_1$, $X_2$, and $X_3$ may be N. $R_{31}$ to $R_{35}$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

In Formula 9, for example, $X_1$, $X_2$ and $X_3$ may be N; or $X_1$ and $X_3$ may be N, and $X_2$ may be $C(R_{34})$; or $X_1$ and $X_2$ may be N, and $X_3$ may be $C(R_{35})$. However, Formula 9 is not limited thereto.

In Formula 1, $Y_1$ may be S or O. In Formula 1, the ring $A_5$ may be represented by one of Formulae 8(1) to 8(4), where at least one of the $R_{24}$s (i.e., ai) of Formula 8(1) and at least one of $R_{24}$s (i.e., aj) of Formula 8(2) may be $-(L_2)_{ao}$-$(R_{12})_{ap}$ as described above. The $-(L_2)_{ao}$-$(R_{12})_{ap}$ is as described above.

For example, the condensed-cyclic compound of Formula 1 may be represented by Formula 3A below.

Formula 3A

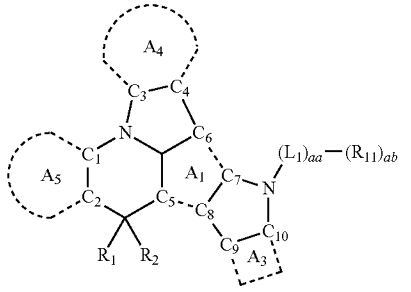

In Formula 3A, the ring $A_1$ may be represented by any one of Formulae 5(1) and 5(2), the ring $A_3$ may be represented by any one of Formulae 6(1) to 6(4), the ring $A_4$ may be represented by any one of Formulae 7(1) to 7(4), and the ring $A_5$ may be represented by any one of Formulae 8(1) to 8(4). In Formulae 5(1), 5(2), 6(1) to 6(4), 7(1) to 7(4), and 8(1) to 8(4), $R_{21}$ to $R_{24}$ may be hydrogen.

Alternatively, in Formula 3A, the ring $A_1$ may be represented by any one of Formulae 5(1) and 5(2), the ring $A_3$ may be represented by any one of Formulae 6(1) and 6(2), the ring $A_4$ may be represented by any one of Formulae 7(1) and 7(3), and the ring $A_5$ may be represented by any one of Formulae 8(1) and 8(3). In Formulae 5(1) to 5(3), 6(1), 6(2), 7(1), 7(3), and 8(1) and 8(3), $R_{21}$ to $R_{24}$ may be hydrogen.

Alternatively, the condensed-cyclic compound of Formula 1 may be represented by Formula 3B or 3C below.

Formula 3B

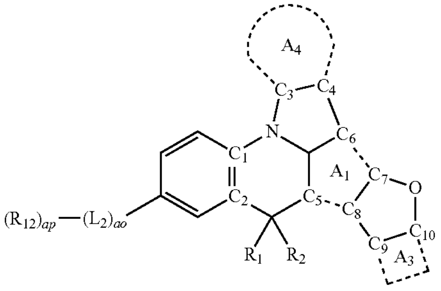

Formula 3C

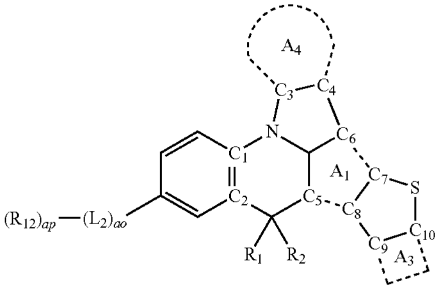

In Formulae 3B and 3C, the ring $A_1$ may be represented by any one of Formulae 5(1) and 5(2), the ring $A_3$ may be represented by any one of Formulae 6(1) to 6(4), and the ring $A_4$ may be represented by any one of Formulae 7(1) to 7(4). In Formulae 5(1) and 5(2), 6(1) to 6(4), and 7(1) to 7(4), $R_{21}$ to $R_{23}$ may be hydrogen. In Formulae 3B and 3C, $L_2$, ao, $R_{12}$, and ap are as described above.

Alternatively, in Formulae 3B and 3C, the ring $A_r$ may be represented by any one of Formulae 5(1) and 5(2), the ring $A_3$ may be represented by any one of Formulae 6(1) and 6(2), and the ring $A_4$ may be represented by any one of Formulae 7(1) and 7(3). In Formulae 5(1) and 5(2), 6(1) to 6(2), and 7(1) to 7(3), $R_{21}$ to $R_{23}$ may be hydrogen. In Formulae 3B and 3C, $L_2$, ao, $R_{12}$, and ap are as described above.

In Formula 1, $R_1$ and $R_2$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group. $R_1$ and $R_2$ are non-ring forming substituents which are not linked to each other and do not form a ring. That is, in Formula 1, $R_1$ and $R_2$ are not linked to each other and do not form a ring.

In Formula 1, $R_1$ and $R_2$ may each independently be a substituted or unsubstituted $C_1$-$C_{10}$ alkyl group, a substituted or unsubstituted $C_1$-$C_{10}$ alkoxy group, or a substituted or unsubstituted $C_6$-$C_{14}$ aryl group.

For example, in Formula 1, $R_1$ and $R_2$ may each independently be:

a $C_1$-$C_{20}$ alkyl group or a $C_1$-$C_{20}$ alkoxy group; or a $C_1$-$C_{20}$ alkyl group or a $C_1$-$C_{20}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a $C_6$-$C_{14}$ aryl group; or a $C_6$-$C_{14}$ aryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

For example, in Formula 1, $R_1$ and $R_2$ may each independently be:

a methyl group, an ethyl group, a propyl group, a butyl group, a pentyl group, a hexyl group, a heptyl group, an octyl group, a methoxy group, an ethoxy group, a propoxy group, a butoxy group, or a pentoxy group; or a methyl group, an ethyl group, a propyl group, a butyl group, a pentyl group, a hexyl group, a heptyl group, an octyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a phenyl group, a naphthyl group, or an anthracenyl group; or a phenyl group, a naphthyl group, or an anthracenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

According to an embodiment, the condensed-cyclic compound may be represented by any one of Formulae 3-1 to 3-20 below, but is not limited thereto.

Formula 3-1

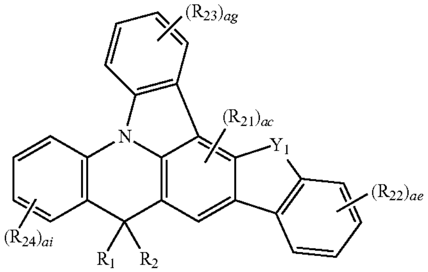

Formula 3-2

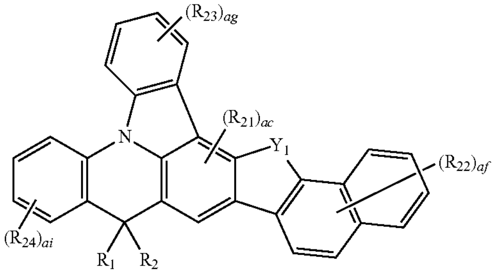

Formula 3-3

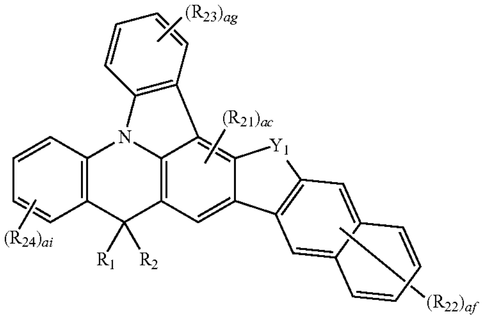

Formula 3-4

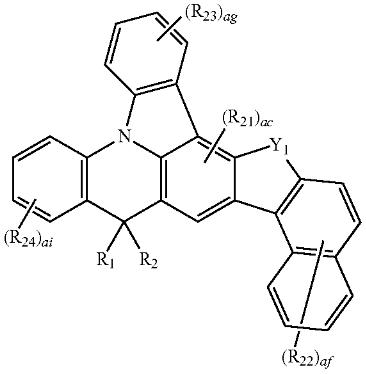

-continued

Formula 3-5

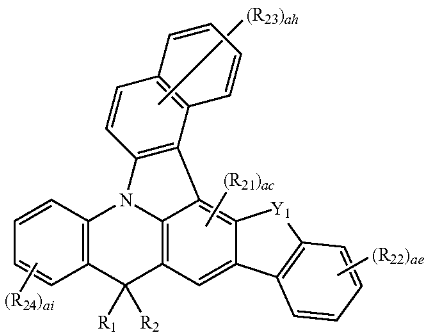

Formula 3-6

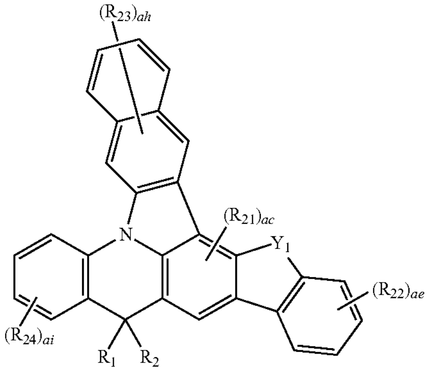

Formula 3-7

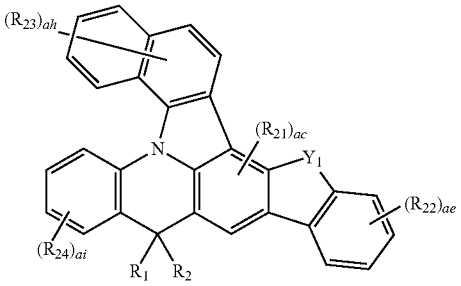

Formula 3-8

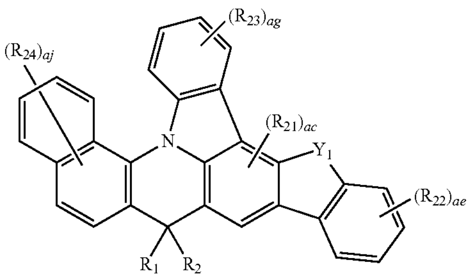

Formula 3-9
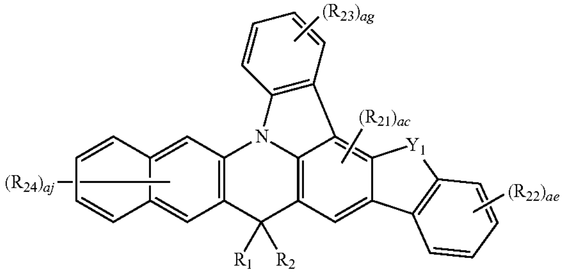
Formula 3-10
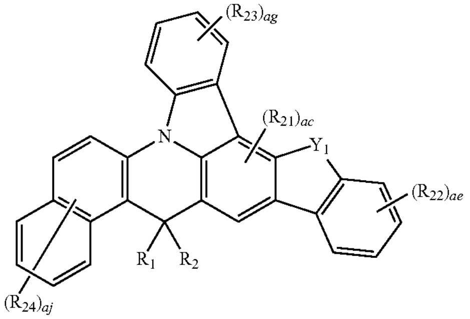
Formula 3-11
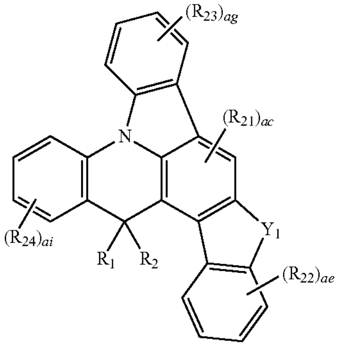
Formula 3-12
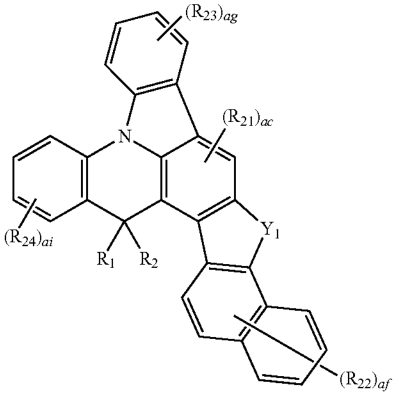
Formula 3-13
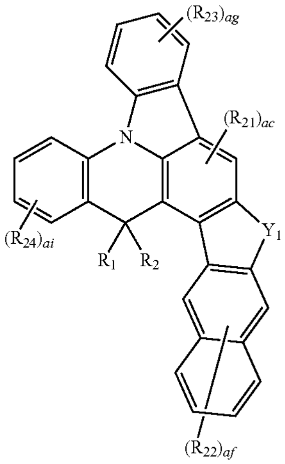
Formula 3-14
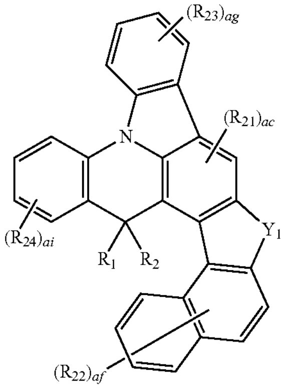
Formula 3-15
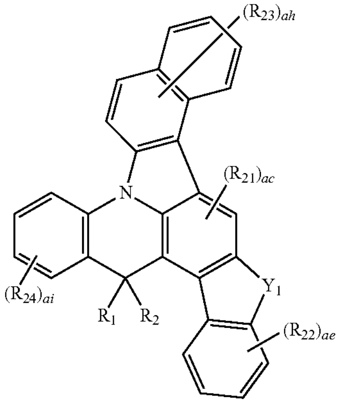

-continued

Formula 3-16

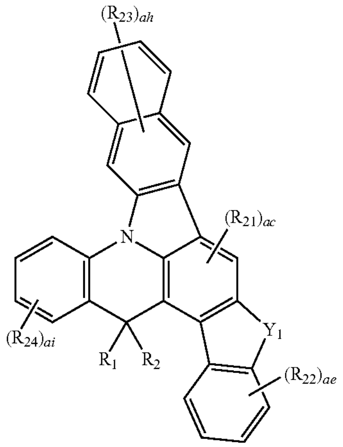

Formula 3-17

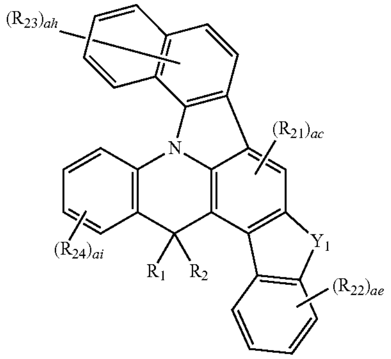

Formula 3-18

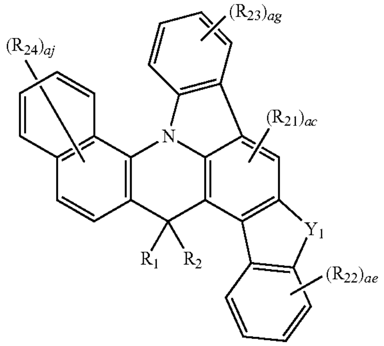

Formula 3-19

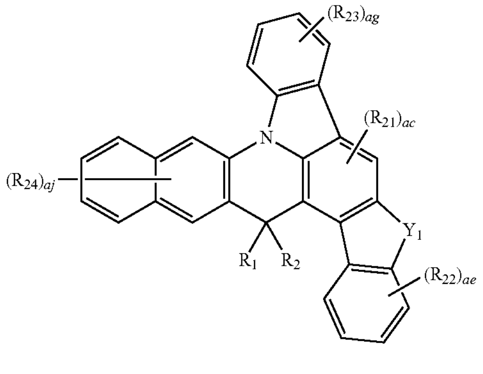

-continued

Formula 3-20

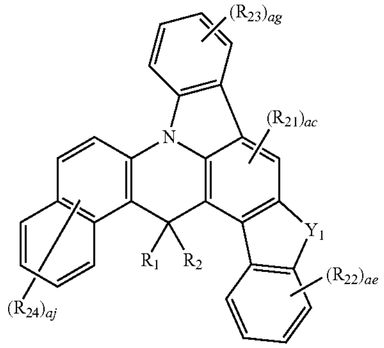

In Formulae 3-1 to 3-20, $R_1$, $R_2$, $R_{21}$ to $R_{24}$, $Y_1$, and ac to aj are as described above.

For example, in Formulae 3-1 to 3-20, $Y_1$ may be $N-(L_1)_{aa}-(R_{11})_{ab}$; and $R_{21}$ to $R_{24}$ may be hydrogen, but Formulae 3-1 to 3-20 are not limited thereto.

Alternatively, for example, in Formulae 3-1 to 3-20, $Y_1$ may be S or O; $R_{21}$ to $R_{24}$ may be hydrogen; al and aj may be 1; and $R_{24}$ may be $-(L_2)_{ao}-(R_{12})_{ap}$, but Formulae 3-1 to 3-20 are not limited thereto. $L_2$, ao, $R_{12}$, and ap are as described above.

According to an embodiment, the condensed-cyclic compound may be represented by any one of Formulae 4-1 to 4-20 below, but is not limited thereto.

Formula 4-1

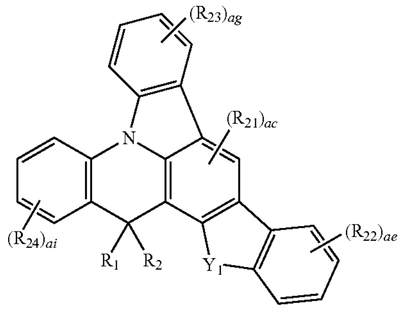

Formula 4-2

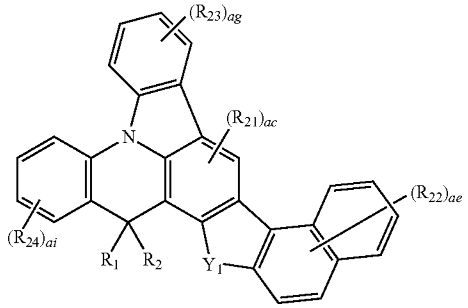

-continued
Formula 4-3
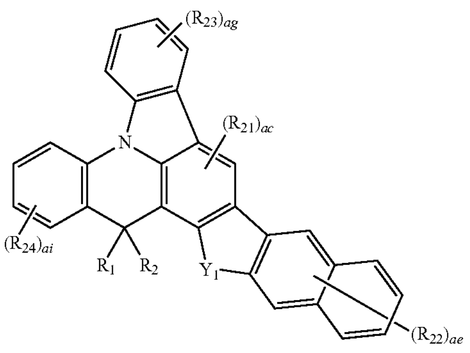
Formula 4-4
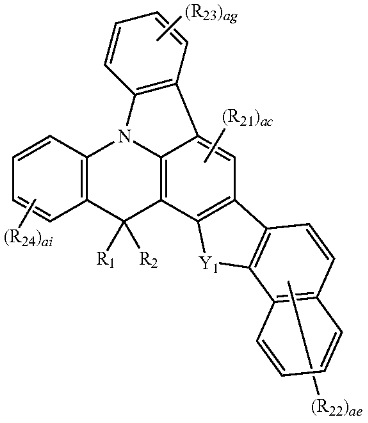
Formula 4-5
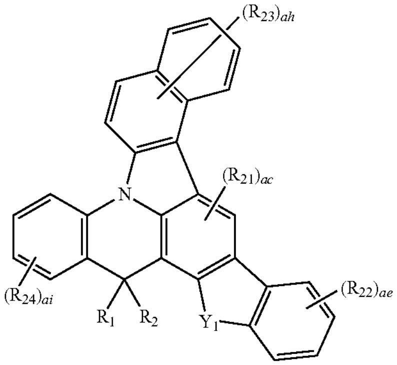
Formula 4-6
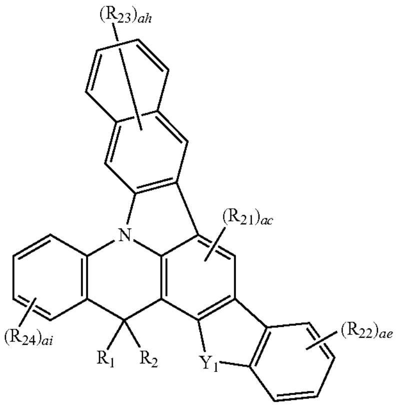
-continued
Formula 4-7
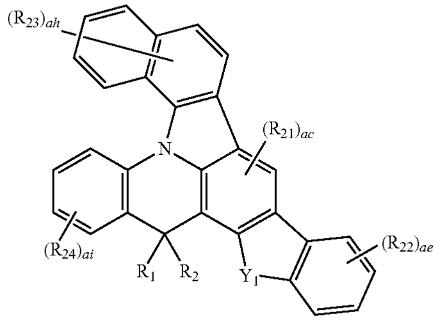
Formula 4-8
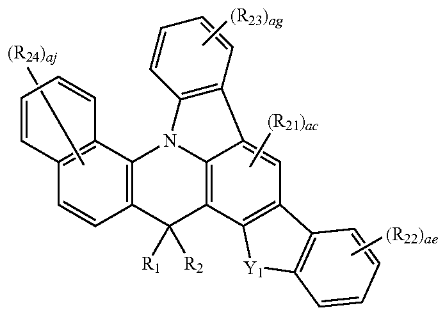
Formula 4-9
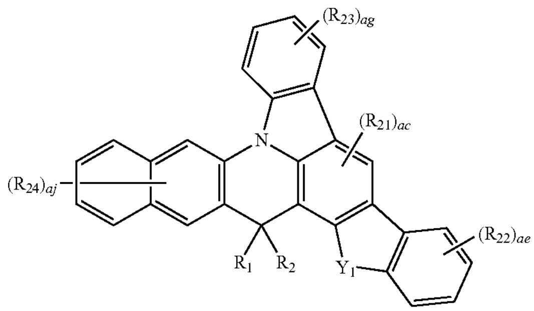
Formula 4-10
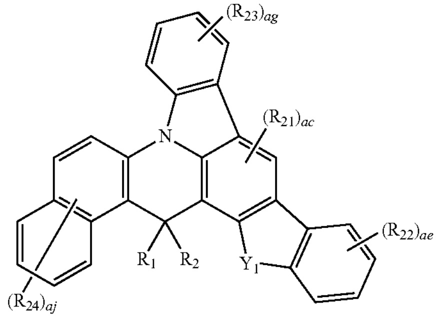

-continued
Formula 4-11
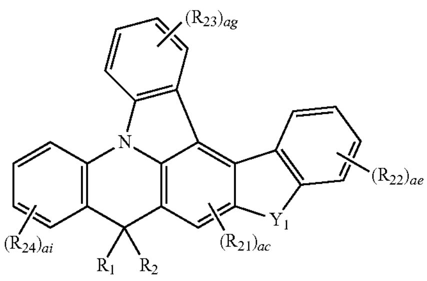
Formula 4-12
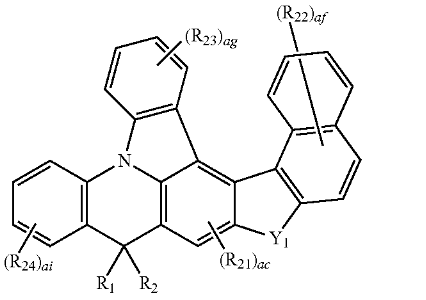
Formula 4-13
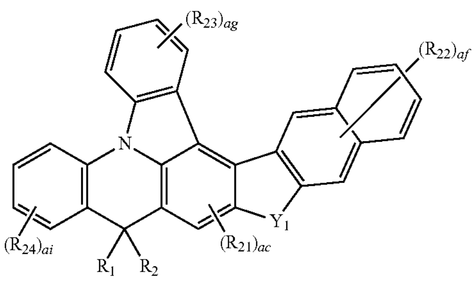
Formula 4-14
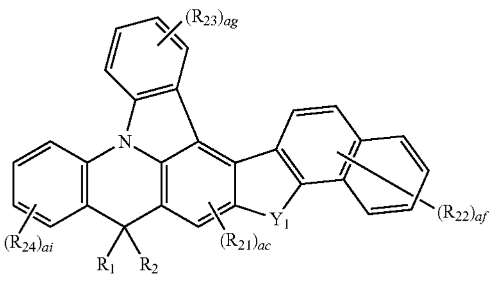
Formula 4-15
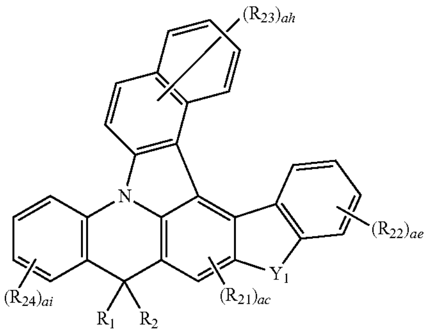
-continued
Formula 4-16
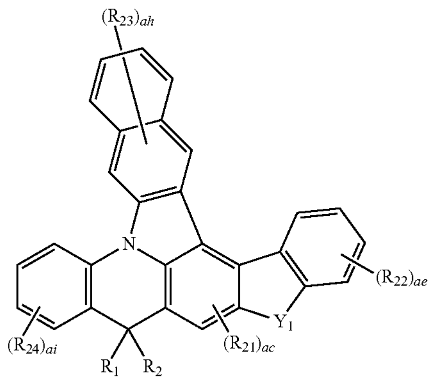
Formula 4-17
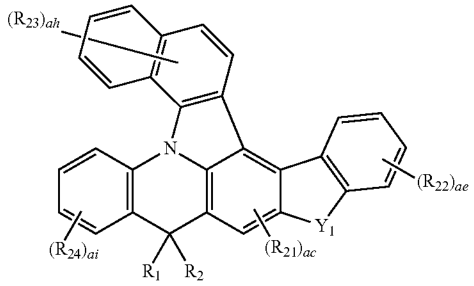
Formula 4-18
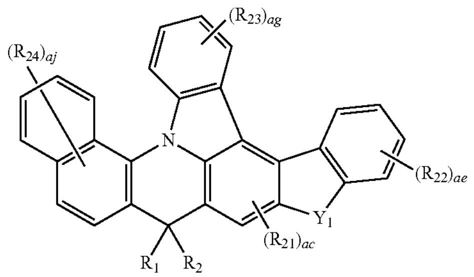
Formula 4-19
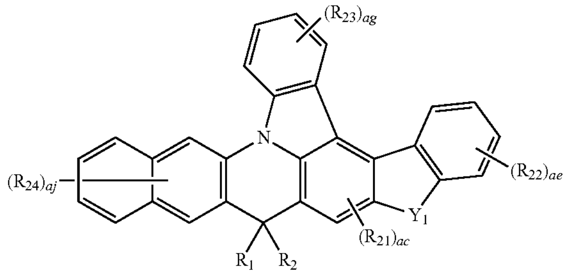

-continued

Formula 4-20

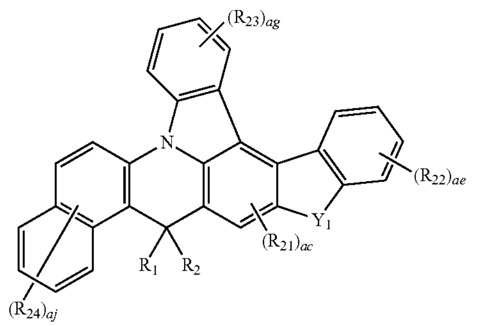

In Formulae 4-1 to 4-20, $R_1$, $R_2$, $R_{21}$ to $R_{24}$, $Y_1$, and ac to aj are as described above.

For example, in Formulae 3-1 to 3-20 and 4-1 to 4-20, $R_1$ and $R_2$ may each independently be a substituted or unsubstituted $C_1$-$C_{10}$ alkyl group, a substituted or unsubstituted $C_1$-$C_{10}$ alkoxy group, or a substituted or unsubstituted $C_6$-$C_{14}$ aryl group.

$R_{21}$ to $R_{24}$ may each independently be:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a hexyl group, a heptyl group, an octyl group, a methoxy group, an ethoxy group, a propoxy group, a butoxy group, or a pentoxy group; or a methyl group, an ethyl group, a propyl group, a butyl group, a pentyl group, a hexyl group, a heptyl group, an octyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a phenyl group, a naphthyl group, an anthracenyl group, a pyridinyl group, a pyrimidinyl group, a pyrazinyl group, or a triazinyl group; or a phenyl group, a naphthyl group, an anthracenyl group, a pyridinyl group, a pyrimidinyl group, a pyrazinyl group, or a triazinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; or $-(L_2)_{ao}-(R_{12})_{ap}$.

$Y_1$ may be O, S, or $N-(L_1)_{aa}-(R_{11})_{ab}$.

ac to aj may be 1 or 2.

$L_1$ may be a substituted or unsubstituted phenylene group, a substituted or unsubstituted naphthylene group, or a substituted or unsubstituted anthracenylene group.

aa may be 0, 1, or 2.

$R_{11}$ may be:

a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, or an isoquinolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, or an isoquinolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

ab may be 1 or 2.

For example, in Formulae 3-1 to 3-20 and 4-1 to 4-20, $R_1$ and $R_2$ may each independently be:

a methyl group, an ethyl group, a propyl group, a butyl group, a pentyl group, a hexyl group, a heptyl group, an octyl group, a methoxy group, an ethoxy group, a propoxy group, a butoxy group, or a pentoxy group; or a methyl group, an ethyl group, a propyl group, a butyl group, a pentyl group, a hexyl group, a heptyl group, an octyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a phenyl group, a naphthyl group, or an anthracenyl group; or a phenyl group, a naphthyl group, or an anthracenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

$R_{21}$ to $R_{24}$ may each be hydrogen.

$Y_1$ may be O, S, or $N-(L_1)_{aa}-(R_{11})_{ab}$.

ac to aj may be 1 or 2.

For example, $L_1$ may be a substituted or unsubstituted phenylene group, a substituted or unsubstituted naphthylene group, or a substituted or unsubstituted anthracenylene group. aa may be 0, 1, or 2. $R_{11}$ may be represented by Formula 9. ab may be 1 or 2.

For example, the condensed-cyclic compound may be represented by any one of Formulae 3-1, 3-6, 3-9, 3-11, and 3-14. $Y_1$ may be $N-(L_1)_{aa}-(R_{11})_{ab}$. $L_1$ may be a substituted or unsubstituted phenylene group, a substituted or unsubstituted naphthylene group, a substituted or unsubstituted fluorenylene group, a substituted or unsubstituted Spiro-fluorenylene group, a substituted or unsubstituted anthracenylene group, a substituted or unsubstituted fluoranthenylene group, a substituted or unsubstituted triphenylenylene group, or a substituted or unsubstituted pyrenylene. aa may be 0, 1, or 2. $R_{11}$ may be represented by Formula 9. ab may be 1 or 2. $R_1$ and $R_2$ may each independently be a methyl group, an ethyl group, a propyl group, a butyl group, a pentyl group, a phenyl group, a naphthyl group, or an anthracenyl group. However, the condensed-cyclic compound is not limited thereto.

In some embodiments, the condensed-cyclic compound may be represented by any one of Formulae 3-1, 3-6, 3-9, 3-11, and 3-14. $Y_1$ may be O or S. $R_{24}$ may be $(L_2)_{ao}$-$(R_{12})_{ap}$. $L_2$ may be a substituted or unsubstituted phenylene group, a substituted or unsubstituted naphthylene group, a substituted or unsubstituted fluorenylene group, a substituted or unsubstituted spiro-fluorenylene group, a substituted or unsubstituted anthracenylene group, a substituted or unsubstituted fluoranthenylene group, a substituted or unsubstituted triphenylenylene group, or a substituted or unsubstituted pyrenylene. ao may be 0, 1, or 2. $R_{12}$ may be represented by Formula 9. ap may be 1 or 2. $R_1$ and $R_2$ may each independently be a methyl group, an ethyl group, a propyl group, a butyl group, a pentyl group, a phenyl group, a naphthyl group, or an anthracenyl group. However, the condensed-cyclic compound is not limited thereto.

According to an embodiment, the condensed-cyclic compound may be any one of Compounds 1 to 13 below, but is not limited thereto.

1

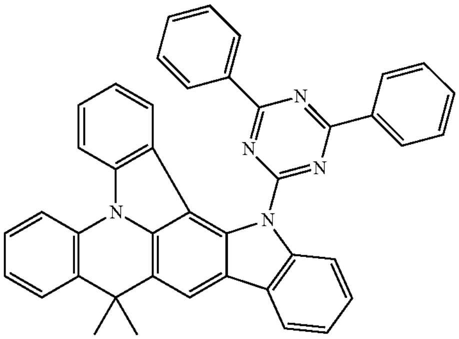

2

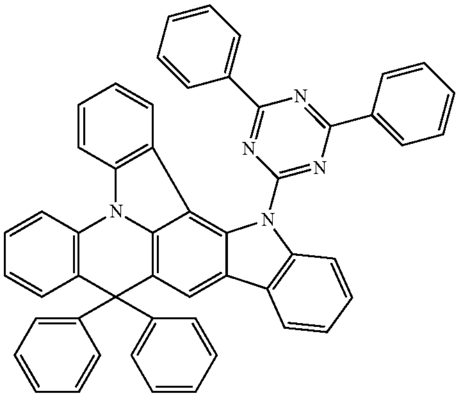

3

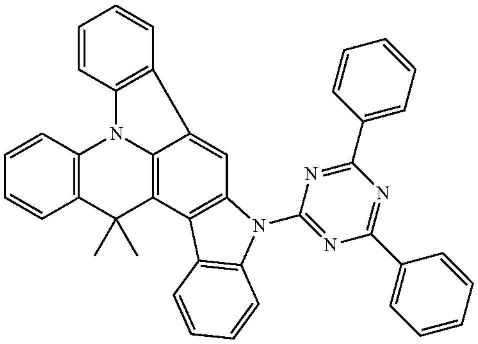

-continued

4

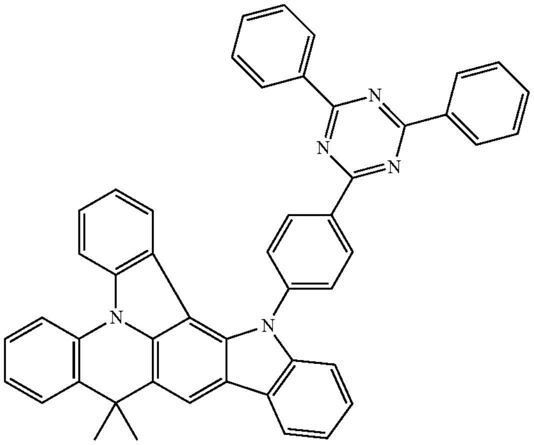

5

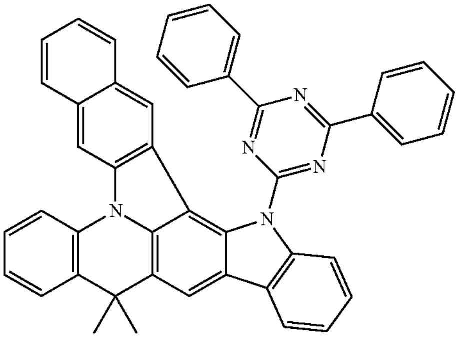

6

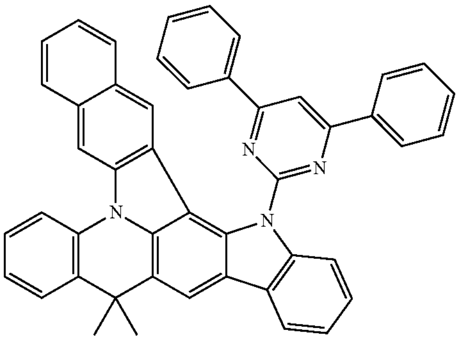

7

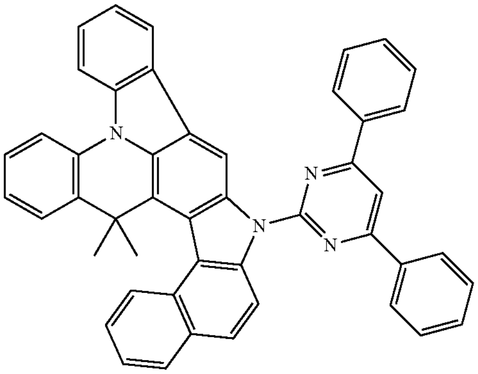

-continued

8

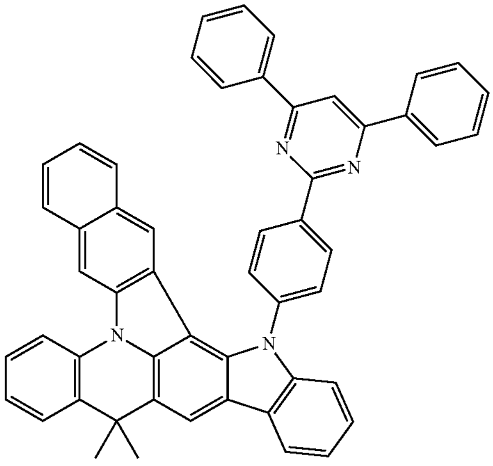

9

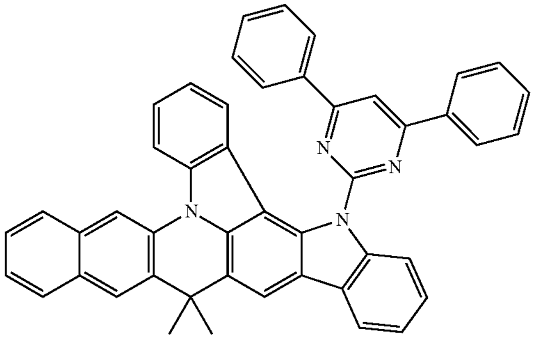

10

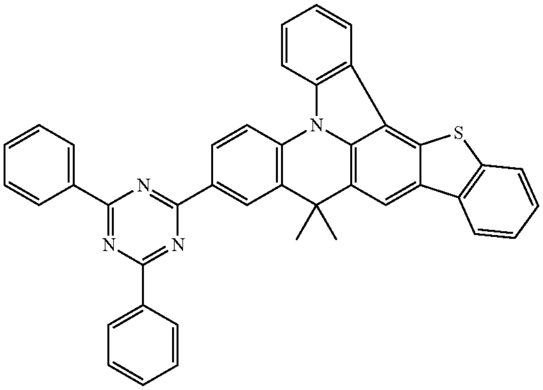

11

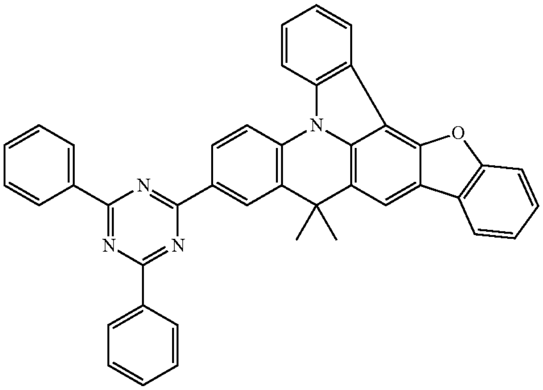

-continued

12

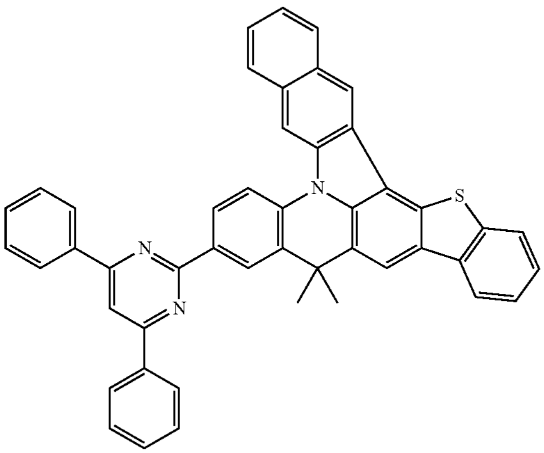

13

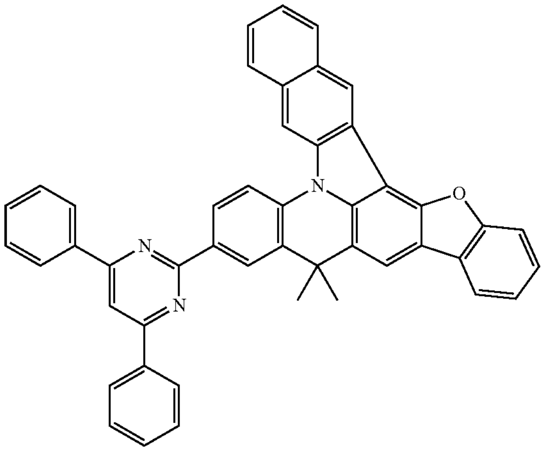

Since $Y_1$ of Formula 2 (which may be the ring $A_2$ of the condensed-cyclic compound represented by Formula 1) may be O, S, or N-$(L_1)_{aa}$-$(R_{11})_{ab}$, the condensed-cyclic compound of Formula 1 may improve hole mobility and electron mobility in a balanced way. Thus, the condensed-cyclic compound may be used as an efficient light-emitting material, and particularly as a phosphorescent host material of an organic light-emitting diode.

Formula 1

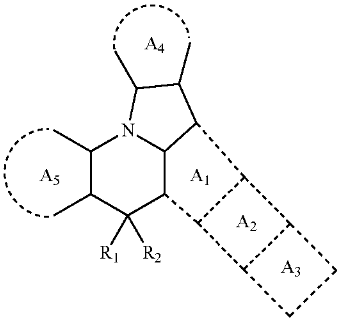

-continued

Formula 2

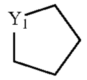

In addition, in the condensed-cyclic compound of Formula 1, $R_1$ and $R_2$ are not linked to each other. Since the condensed-cyclic compound of Formula 1 is easily synthesized, has a molecular weight suitable for deposition, and has thermal resistance, an organic light-emitting diode including the condensed-cyclic compound of Formula 1 may have a long lifespan.

Thus, an organic light-emitting diode including the condensed-cyclic compound may have low driving voltage, high efficiency, high brightness, and a long lifespan.

The condensed-cyclic compound represented by Formula 1 may be synthesized using known organic synthesis methods. Methods for synthesizing the condensed-cyclic compounds will be understood by those of ordinary skill in the art by reference to the examples described later.

The condensed-cyclic compound of Formula 1 may be placed between a pair of electrodes of an organic light-emitting diode. For example, the condensed-cyclic compound may be used in an emission layer (EML).

Therefore, according to embodiments of the present invention, an organic light-emitting diode includes a first electrode, a second electrode facing the first electrode, and an organic layer between the first electrode and the second electrode and including an emission layer. The organic layer includes at least one condensed-cyclic compound represented by Formula 1 as described above.

The organic layer may include i) at least one layer selected from a hole injection layer (HIL), a hole transport layer (HTL), a functional layer having both hole injecting and hole transporting capabilities (H-functional layer), a buffer layer, and an electron blocking layer (EBL) between the first electrode and the EML, and ii) at least one layer selected from a hole blocking layer (HBL), an electron transport layer (ETL), and an electron injection layer (EIL) between the EML and the second electrode.

The EML may include the condensed-cyclic compound represented by Formula 1. Here, the condensed-cyclic compound contained in the EML may be used as a host, and the EML may further include a dopant. The dopant may include an organometallic compound including Ir, Pt, Os, Ti, Zr, Hf, Eu, Tb, or Tm, but is not limited thereto.

As used herein, the phrase "(the organic layer) includes at least one condensed-cyclic compound" may be interpreted as "(the organic layer) includes a single condensed-cyclic compound represented by Formula 1, or at least two different condensed-cyclic compounds represented by Formula 1".

For example, the organic layer may include Compound 1 alone as the condensed-cyclic compound. In such an example, Compound 1 may be present in the EML of the organic light-emitting diode. Alternatively, the organic layer may include Compound 1 and Compound 2, as the condensed-cyclic compounds. In such an example, Compound 1 and Compound 2 may be present in the same layer (for example, Compound 1 and Compound 2 may both be present in the EML), or in different layers (for example, Compound 1 may be present in the EML and Compound 2 may be present in the ETL).

The organic layer may include at least one of a hole injection layer (HIL), a hole transport layer (HTL), a functional layer having both hole injecting and hole transporting capabilities ("H-functional layer"), a buffer layer, an electron blocking layer (EBL), an emission layer (EML), a hole blocking layer (HBL), an electron transport layer (ETL), an electron injection layer (EIL), and/or a functional layer having both electron injecting and electron transporting capabilities ("E-functional layer").

The term "organic layer," as used herein, refers to a single layer and/or multiple layers interposed between the first and second electrodes of the organic light-emitting diode.

FIG. 1 is a schematic cross-sectional view of an organic light-emitting diode 10 according to an embodiment of the present invention. Hereinafter, the organic light-emitting diode 10 and a method of fabricating the organic light-emitting diode 10 will be described with reference to FIG. 1.

A substrate 11, which may be any substrate commonly used in organic light-emitting diodes, may be a glass substrate or a transparent plastic substrate with mechanical strength, thermal stability, transparency, surface smoothness, ease of handling, and water resistance.

A first electrode 13 may be formed on the substrate 11 by depositing or sputtering a first electrode material. When the first electrode 13 is an anode, the first electrode material may be a high work function material to facilitate hole injection. The first electrode 13 may be a reflective electrode or a transmissive electrode. Transparent and conductive materials such as indium tin oxide (ITO), indium zinc oxide (IZO), tin oxide ($SnO_2$), and zinc oxide (ZnO) may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer or multi-layered structure. For example, the first electrode 13 may have a triple-layered structure of ITO/Ag/ITO, but is not limited thereto.

The organic emission layer 15 is formed on the first electrode 13.

The organic layer 15 may include an HIL, an HTL, a buffer layer, an EML, an ETL, and an EIL.

The HIL may be formed on the first electrode 13 by vacuum deposition, spin coating, casting, Langmuir-Blodgett (LB) deposition, or the like. When the HIL is formed using vacuum deposition, the deposition conditions may vary according to the compound used to form the HIL and the desired structural and thermal characteristics of the HIL to be formed. For example, the deposition conditions may include a deposition temperature of about 100 to about 500° C., a vacuum pressure of about $10^{-8}$ to about $10^{-3}$ torr, and a deposition rate of about 0.01 to about 100 Å/sec, but the deposition conditions are not limited thereto.

When the HIL is formed using spin coating, the coating conditions may vary according to the compound used to form the HIL, and the desired structural and thermal characteristics of the HIL to be formed. For example, the coating conditions may include a coating speed of about 2000 rpm to about 5000 rpm, and a thermal treatment temperature of about 80° C. to about 200° C., where the thermal treatment is performed to remove solvent after coating. However, the coating conditions are not limited thereto.

Any hole injecting materials may be used to form the HIL. Non-limiting examples of suitable hole injecting materials include N,N'-diphenyl-N,N'-bis-[4-(phenyl-m-tolyl-amino)-phenyl]-biphenyl-4,4'-diamine (DNTPD), phthalocyanine compounds such as copperphthalocyanine, 4,4',4"-tris(3- methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonic acid (Pani/CSA), and (polyaniline)/poly(4-styrene-sulfonate) (PANI/PSS).

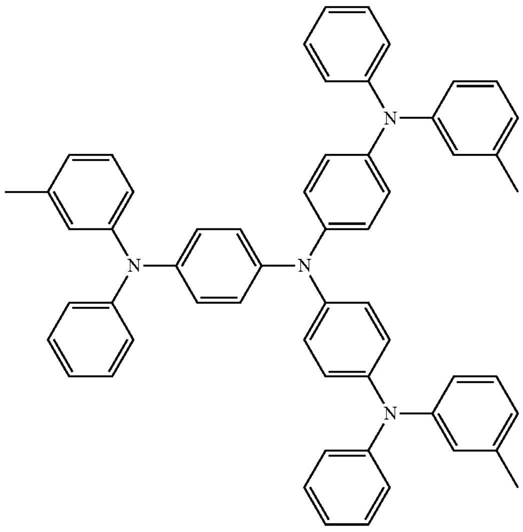

m-MTDATA

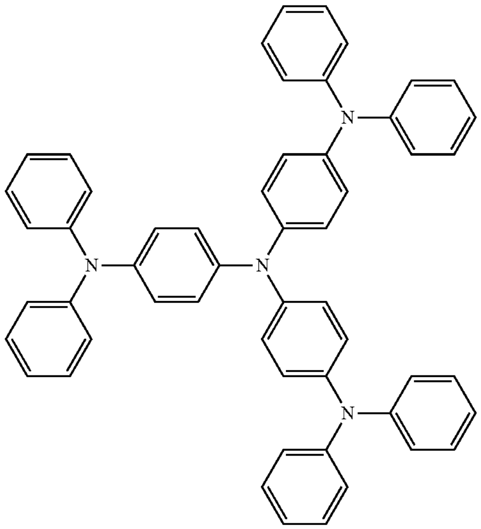

TDATA

-continued

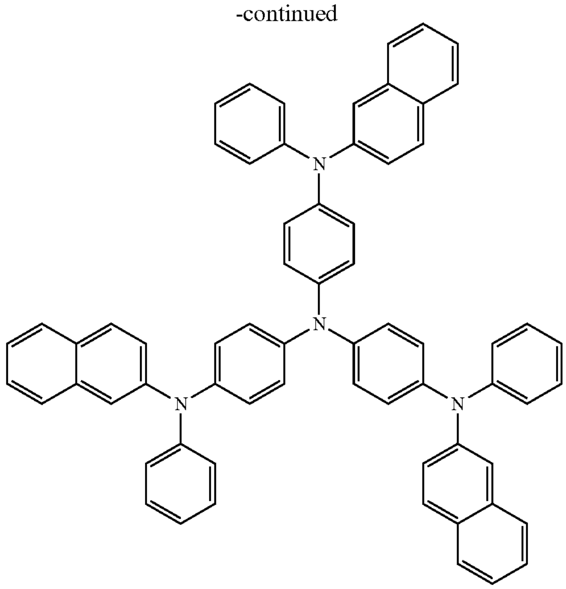

2-TNATA

The thickness of the HIL may be about 100 to about 10,000 Å, and for example, about 100 to about 1,000 Å. When the thickness of the HIL is within these ranges, the HIL may have good hole injecting ability without a substantial increase in driving voltage.

Then, the HTL may be formed on the HIL by vacuum deposition, spin coating, casting, LB deposition, or the like. When the HTL is formed by vacuum deposition or spin coating, the conditions for deposition or coating may be similar to those described above for the formation of the HIL, although the conditions for the deposition or coating may vary according to the material used to form the HTL.

Non-limiting examples of suitable hole transporting materials for the HTL include carbazole derivatives such as N-phenylcarbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine (NPB).

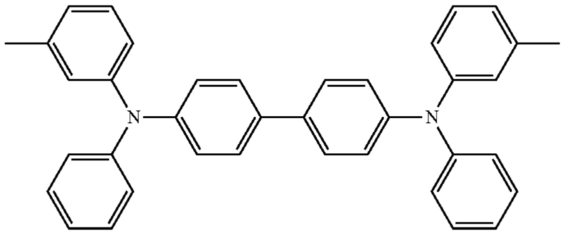

TPD

The thickness of the HTL may be about 50 to about 2,000 Å, for example, about 100 to about 1,500 Å. When the thickness of the HTL is within these ranges, the HTL may have good hole transporting ability without a substantial increase in driving voltage.

The H-functional layer may include at least one of the hole injecting materials and hole transporting materials described above, and the thickness of the H-functional layer may be about 100 Å to about 10,000 Å, for example, about 100 Å to about 1,000 Å. When the thickness of the H-functional layer is within these ranges, the H-functional layer may have good hole injecting and transporting abilities without a substantial increase in driving voltage.

At least one of the HIL, HTL, and the H-functional layer may include at least one compound represented by one of Formulae 300 and 350 below.

Formula 300

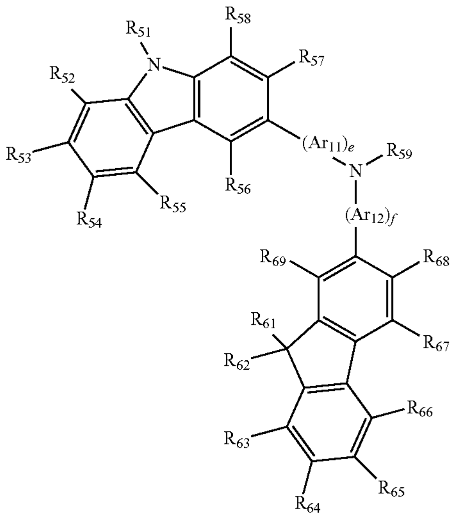

Formula 350

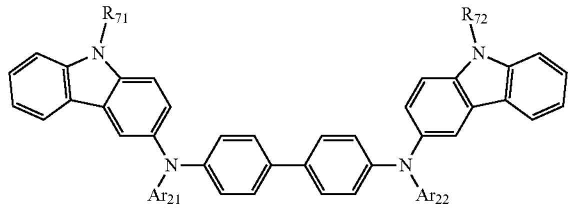

In Formula 300, $Ar_{11}$ and $Ar_{12}$ may each independently be a substituted or unsubstituted $C_6$-$C_{60}$ arylene group. For example, $Ar_{11}$ and $Ar_{12}$ may each independently be:

a phenylene group, a pentalenylene group, a indenylene group, a naphthylene group, a azulenylene group, a heptalenylene group, a acenaphthylene group, a fluorenylene group, a phenalenylene group, a phenanthrenylene group, a anthracenylene group, a fluoranthenylene group, a triphenylenylene group, a pyrenylene group, a chrysenylene group, a naphthacenylene group, a picenylene group, a perylenylene group, or a pentacenylene group; or a phenylene group, a pentalenylene group, a indenylene group, a naphthylene group, a azulenylene group, a heptalenylene group, a acenaphthylene group, a fluorenylene group, a phenalenylene group, a phenanthrenylene group, a anthracenylene group, a fluoranthenylene group, a triphenylenylene group, a pyrenylene group, a chrysenylene group, a naphthacenylene group, a picenylene group, a perylenylene group, or a pentacenylene group substituted with at least one of a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ heterocycloalkenyl group, a $C_3$-$C_{10}$ cycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group.

In Formula 300, e and f may each independently be an integer of 0 to 5, for example 0, 1, or 2. For example, e may be 1, and f may be 0, but Formula 300 is not limited thereto.

In Formulae 300 and 350, $R_{51}$ to $R_{58}$ $R_{61}$ to $R_{69}$, and $R_{71}$ to $R_{72}$ may each independently be a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group.

For example, $R_{51}$ to $R_{58}$, $R_{61}$ to $R_{69}$, and $R_{71}$ to $R_{72}$ may each independently be:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, a pentyl group, or a hexyl group), or a $C_1$-$C_{10}$ alkoxy group (e.g., a methoxy group, an ethoxy group, a propoxy group, a butoxy group, or a pentoxy group); or a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or a phosphoric acid group or a salt thereof; or a phenyl group, a naphthyl group, an anthracenyl group, a fluorenyl group, or a pyrenyl group; or a phenyl group, a naphthyl group, an anthracenyl group, a fluorenyl group, or a pyrenyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group. However, $R_{51}$ to $R_{58}$, $R_{61}$ to $R_{69}$, and $R_{71}$ to $R_{72}$ are not limited thereto.

In Formulae 300 and 350, $R_{59}$, $Ar_{21}$, and $Ar_{22}$ may each independently be a phenyl group, a naphthyl group, an anthracenyl group, a biphenyl group, or a pyridyl group; or a phenyl group, a naphthyl group, an anthracenyl group, a biphenyl group, or a pyridyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment of the present invention, the compound of Formula 300 may be represented by Formula 300A below, but is not limited thereto.

Formula 300A
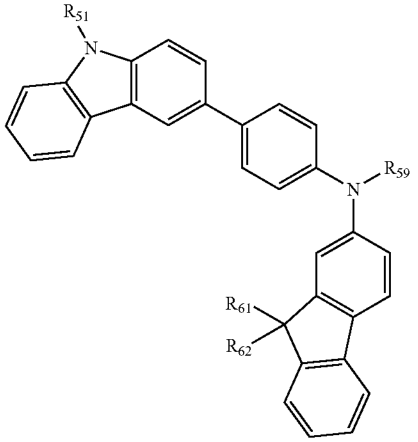
In Formula 300A, $R_{51}$, $R_{61}$, $R_{62}$ and $R_{59}$ are as described above with respect to Formula 300.
For example, at least one of the HIL, the HTL, and the H-functional layer may include at least one of Compounds 301 to 320 below, but the HIL, HTL and H-functional layers are not limited thereto.
301
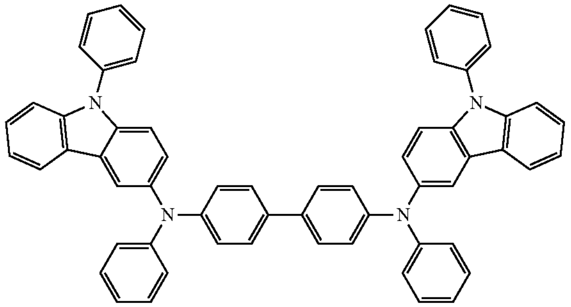
302
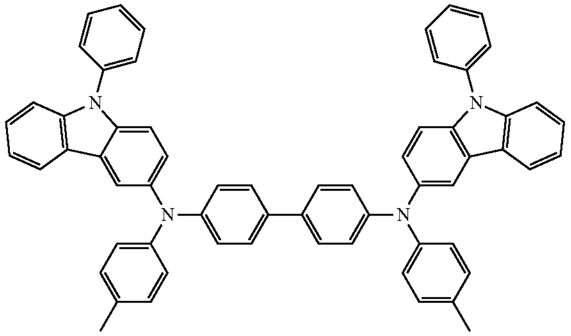
-continued
303
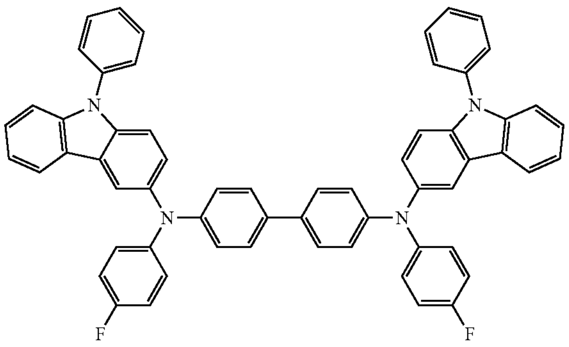
304
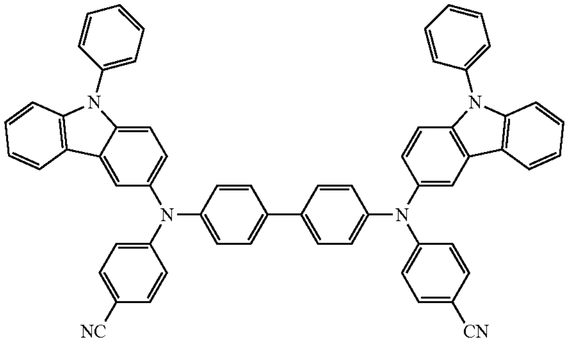
305
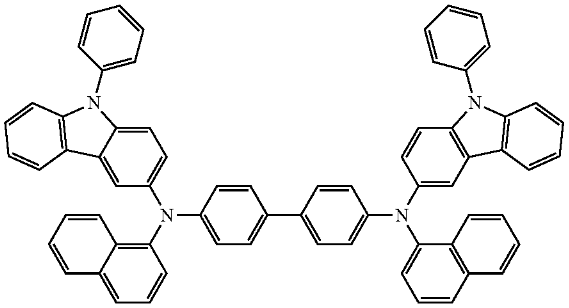
306
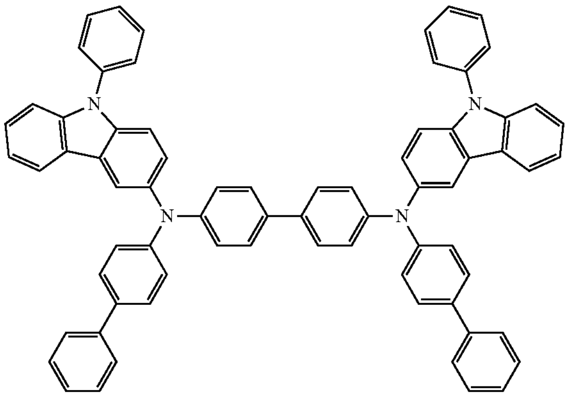

-continued
307
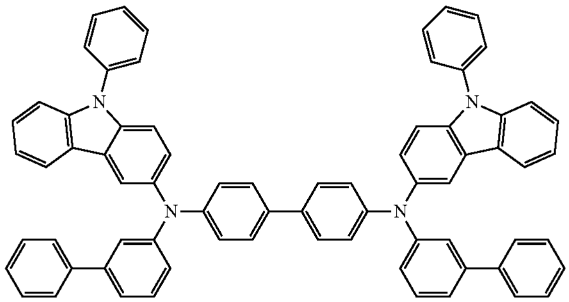
308
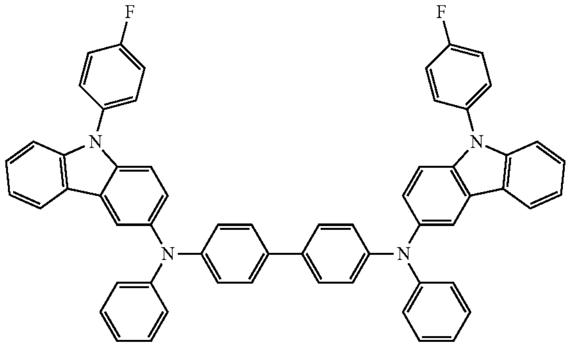
309
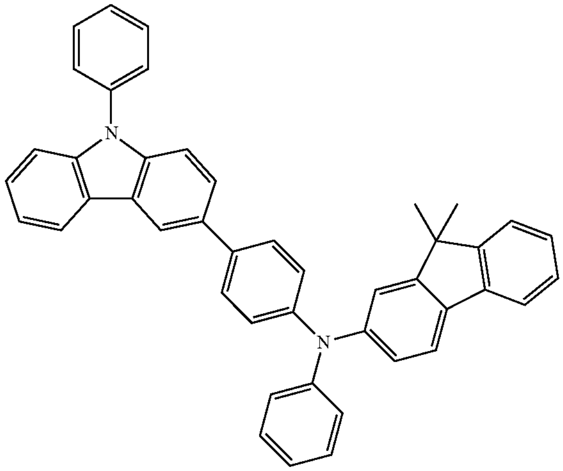
-continued
310
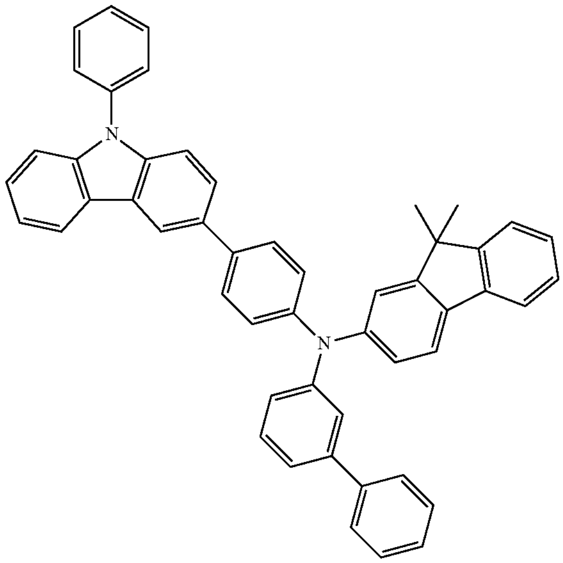
311
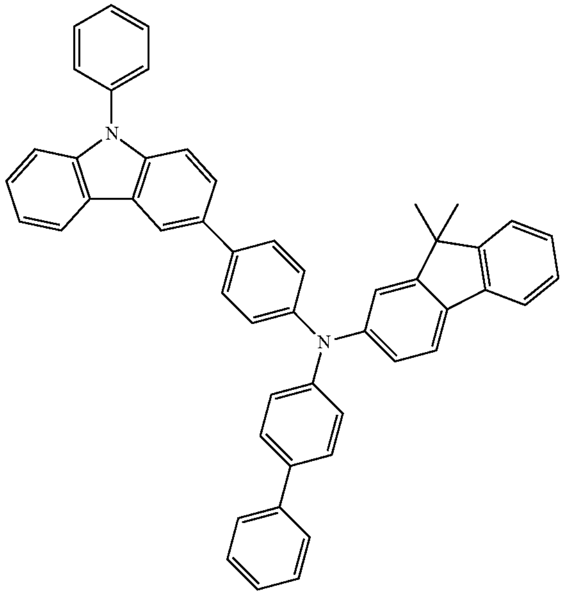

-continued
312
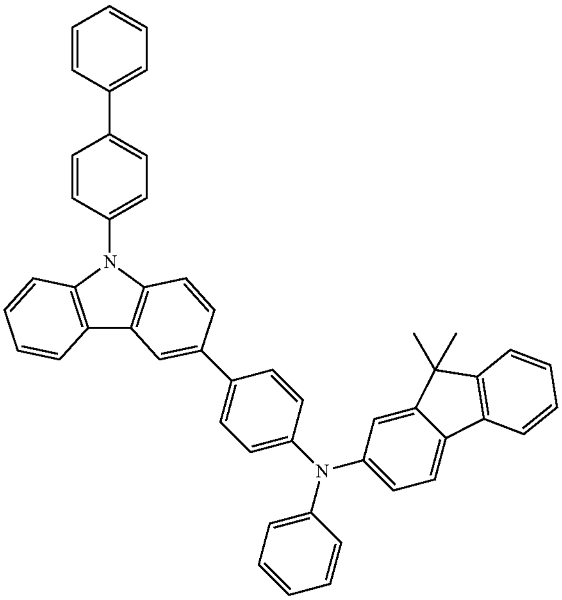
313
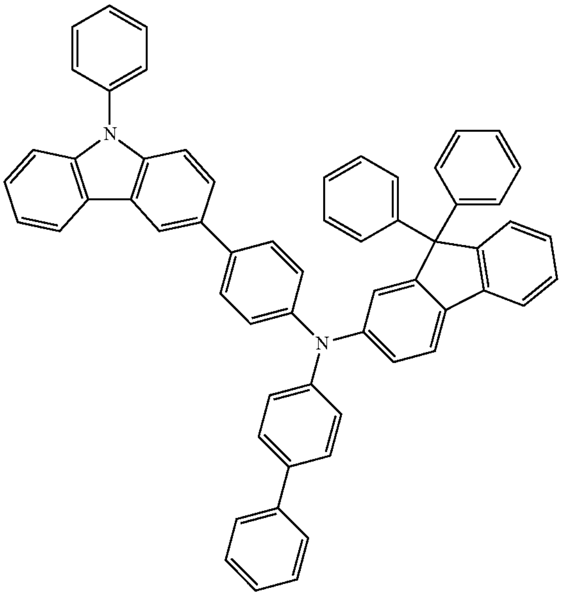
-continued
314
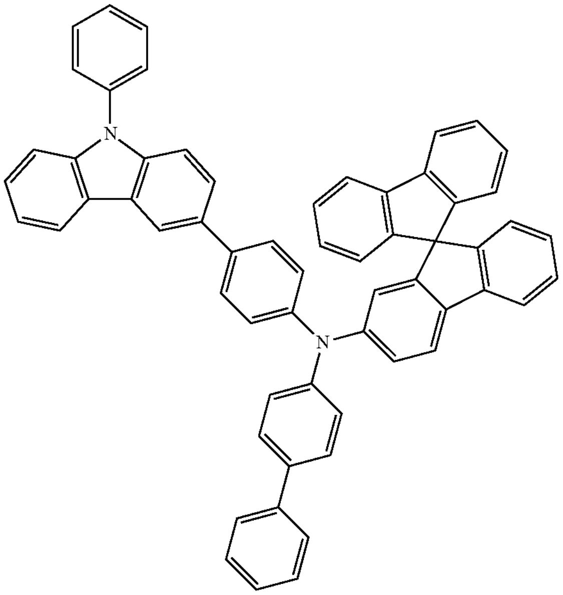
315
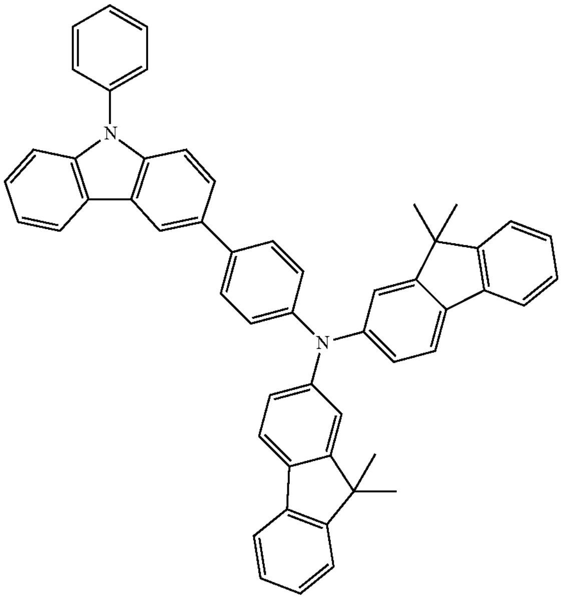

-continued

316

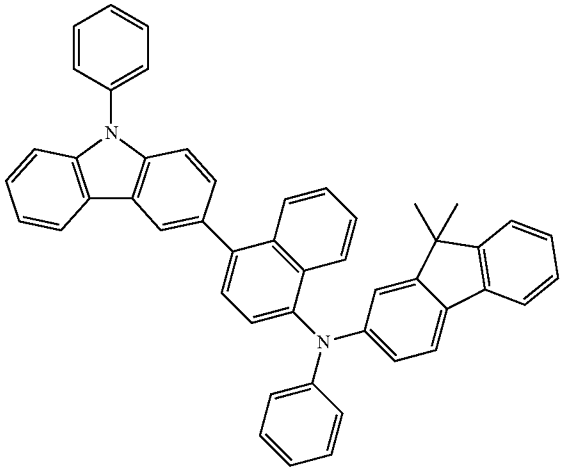

317

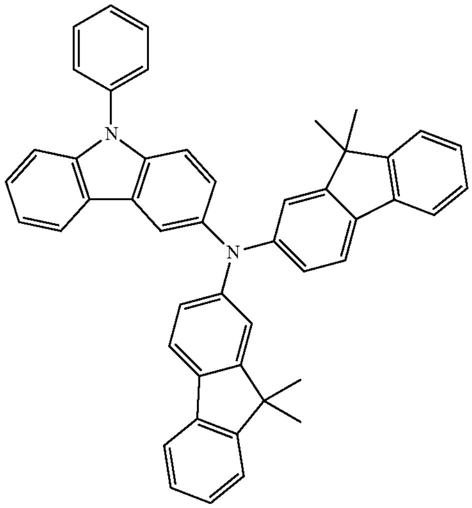

318

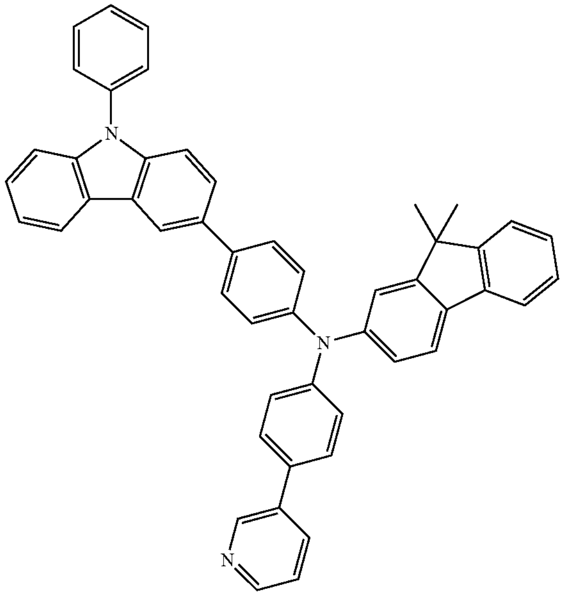

-continued

319

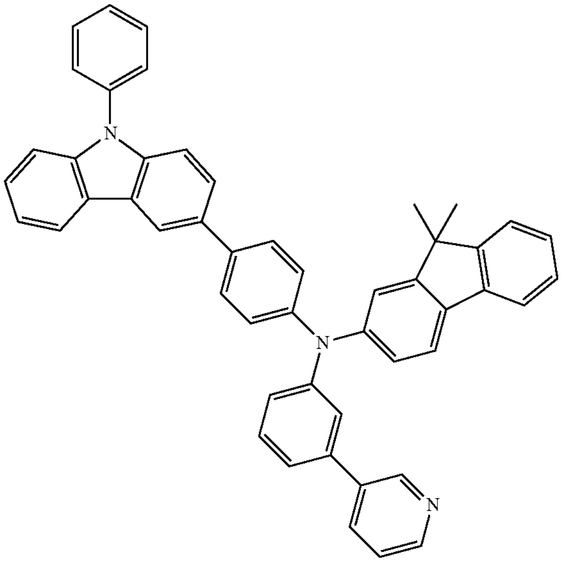

320

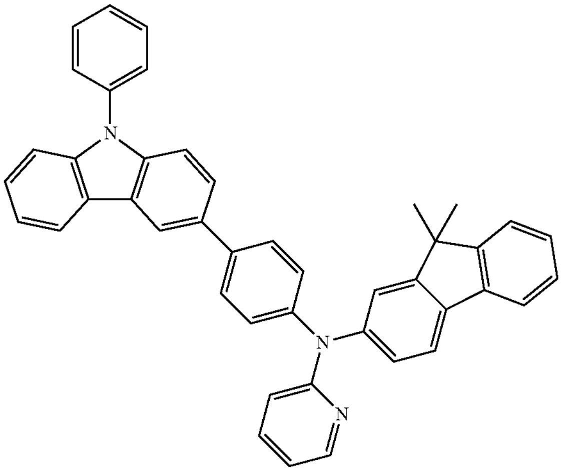

In order to improve conductivity of the layer, at least one of the HIL, the HTL, and the H-functional layer may further include a charge-generating material in addition to the hole injecting material, hole transporting material, and/or material having both hole injecting and hole transporting capabilities.

The charge-generating material may be a p-dopant. The p-dopant may be a quinone derivative, a metal oxide, or a cyano group-containing compound, but is not limited thereto. Non-limiting examples of the p-dopant include quinone derivatives such as tetracyanoquinonedimethane (TCNQ) and 2,3,5,6-tetrafluoro-tetracyano-1,4-benzoquinonedimethane (F4TCNQ); metal oxides such as tungsten oxides and molybdenum oxides; and cyano group-containing compounds such as Compound 200 below, but the p-dopant is not limited thereto.

Compound 200

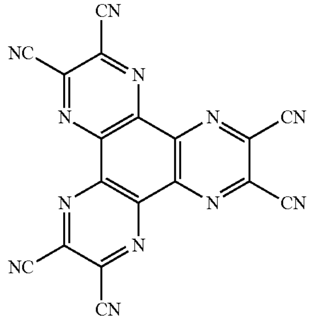

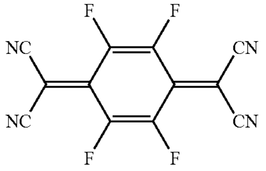

F4-TCNQ

If the HIL, the HTL, or the H-functional layer further includes the charge-generating material, the charge-generating material may be homogeneously or non-homogeneously dispersed in the HIL, the HTL, or the H-functional layer, or a variety of modifications may be possible.

A buffer layer may be disposed between the EML and at least one of the HIL, the HTL, and the H-functional layer. The buffer layer may increase efficiency by compensating for an optical resonance distance according to a wavelength of light emitted from the EML. The buffer layer may include a hole injecting material or a hole transporting material. The buffer layer may also include the same material as that contained in the HIL, the HTL, and the H-functional layer disposed under the buffer layer.

The EML may be formed on the HTL, the H-functional layer, or the buffer layer by vacuum deposition, spin coating, casting, LB deposition, or the like. When the EML is formed by vacuum deposition or spin coating, the deposition or coating conditions may be similar to those described above to form the HIL, although the deposition or coating conditions may vary according to the compound used to form the EML.

The EML may include a host and a dopant. As the host, the condensed-cyclic compound represented by Formula 1 as described above may be used.

If the organic light-emitting diode is a full-color organic light-emitting diode, the EML may be patterned into a red EML, a green EML, and a blue EML. Alternatively, the EML may have a structure in which a red EML, a green EML, and/or a blue EML are deposited, and may emit white light.

At least one of the red, green, and blue EMLs may include the following dopants (ppy=phenylpyridine).

For example, non-limiting examples of a blue dopant include the following compounds.

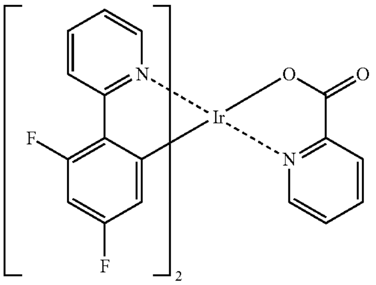

$F_2Irpic$

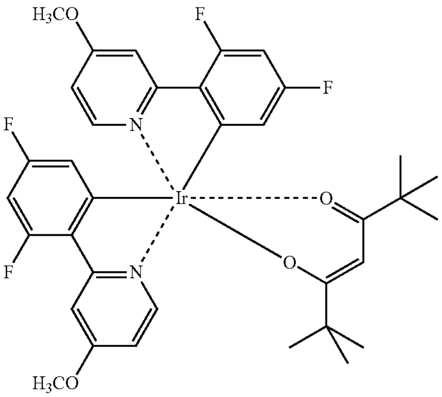

(F2ppy)2Ir(tmd)

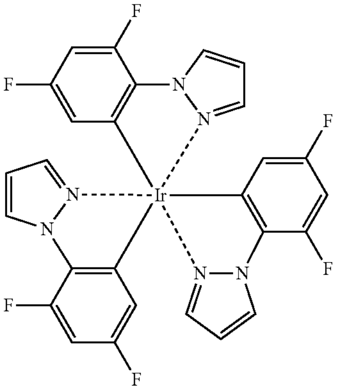

$Ir(dfppz)_3$

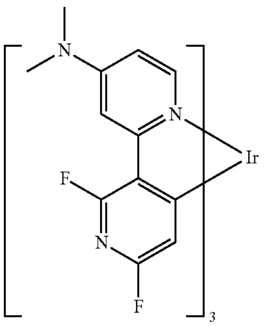

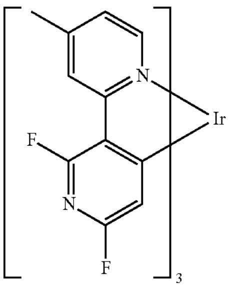

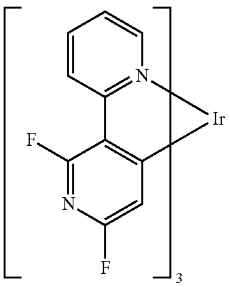

-continued
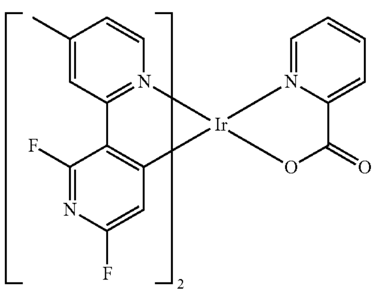
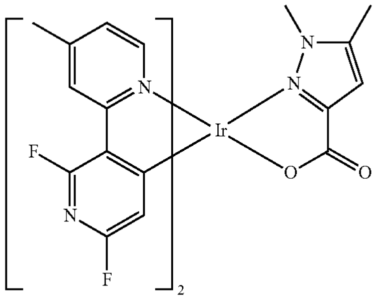
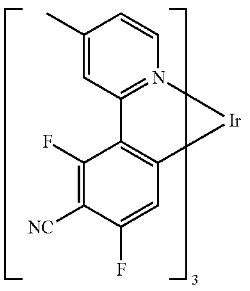
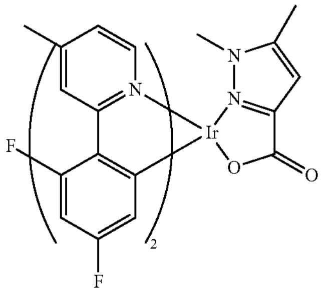
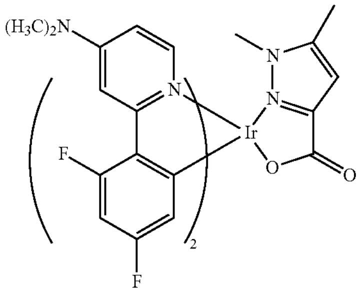
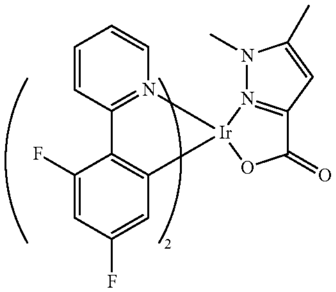
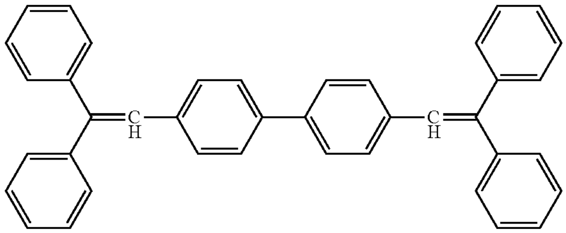
DPVBi
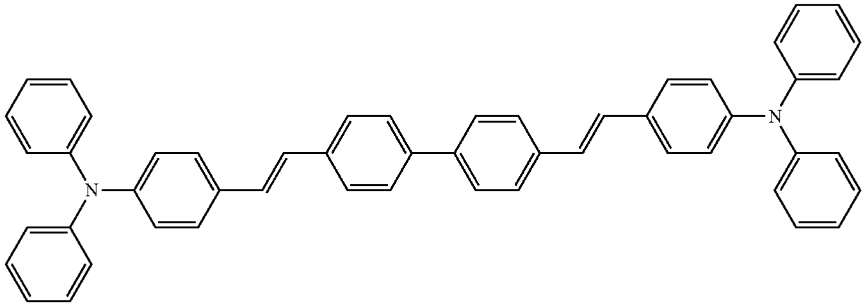
DPAVBi
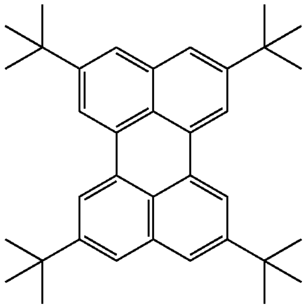
TBPe For example, non-limiting examples of a red dopant include the following compounds. Alternatively, DCM or DCJTB (which will be described later) may be used as a red dopant.
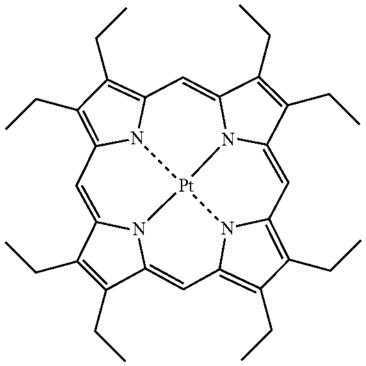
PtOEP
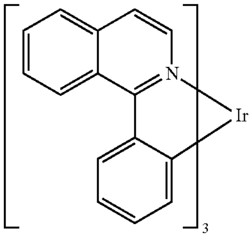
$Ir(piq)_3$
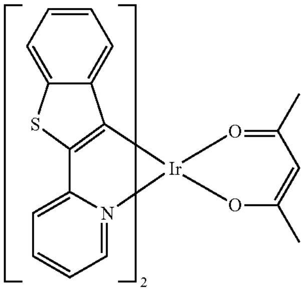
$Btp_2Ir(acac)$
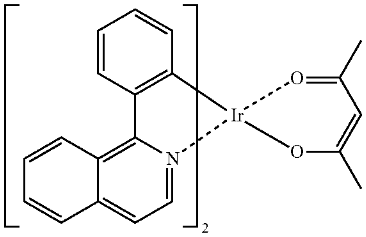
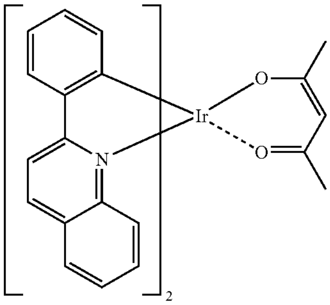
$Ir(pq)_2(acac)$
-continued
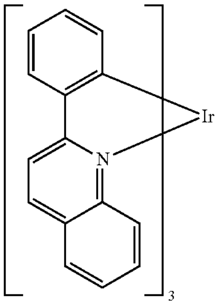
$Ir(2\text{-}phq)_3$
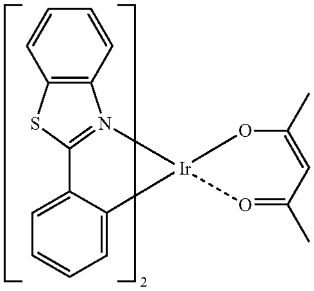
$Ir(BT)_2(acac)$
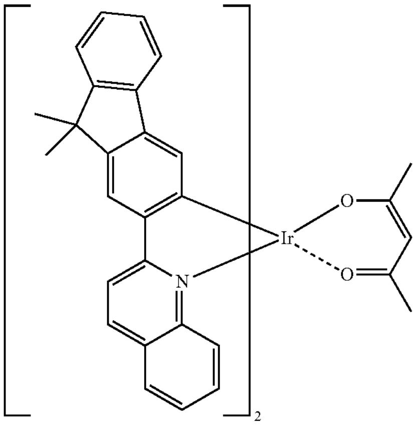
$Ir(flq)_2(acac)$
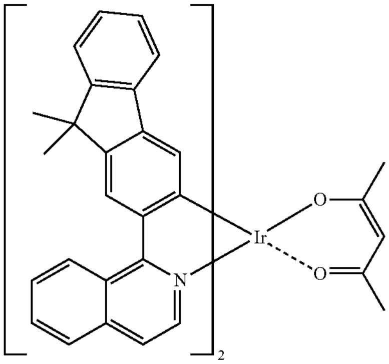
$Ir(fliq)_2(acac)$ -continued
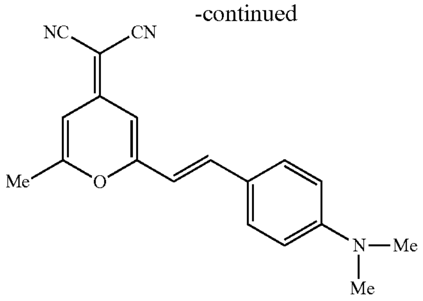
DCM
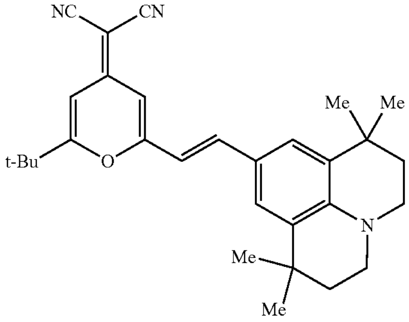
DCJTB
For example, non-limiting examples of a green dopant include the following compounds. Alternatively, C545T below may be used as a green dopant.
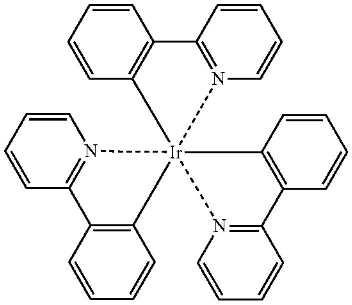
Ir(ppy)$_3$
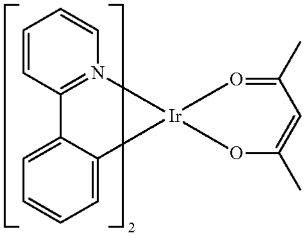
Ir(ppy)$_2$(acac)
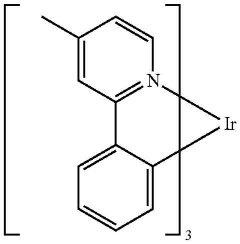
Ir(mppy)$_3$
-continued
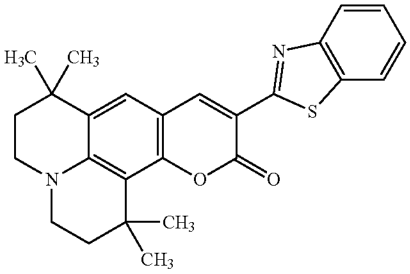
C545T
The dopant used in the EML may be a Pd or Pt complex, non-limiting examples of which include the following compounds D1 through D50.
D1
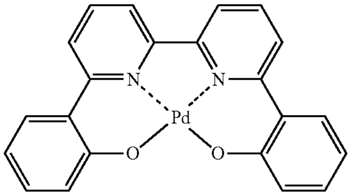
D2
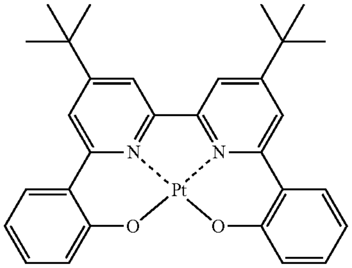
D3
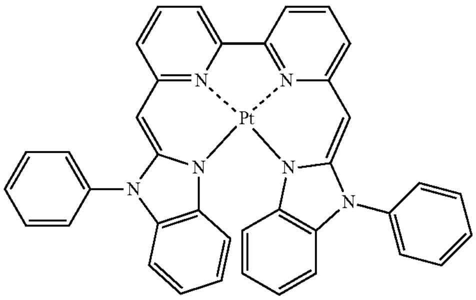
D4
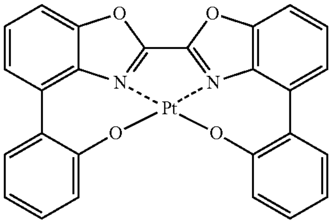

-continued
D5
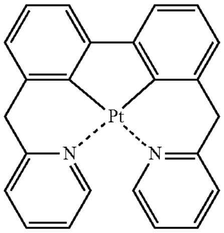
D6
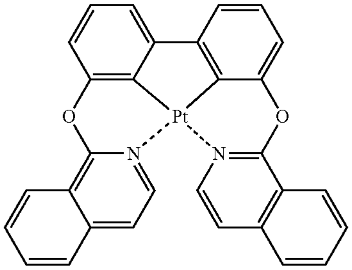
D7
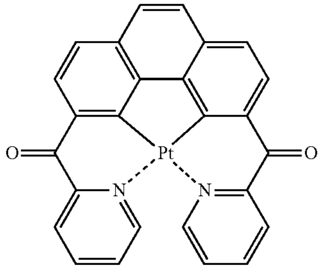
D8
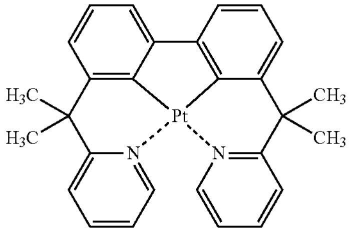
D9
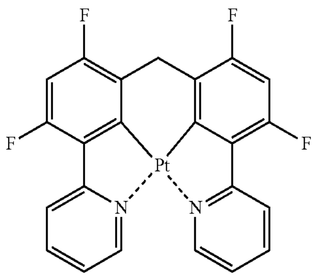
D10
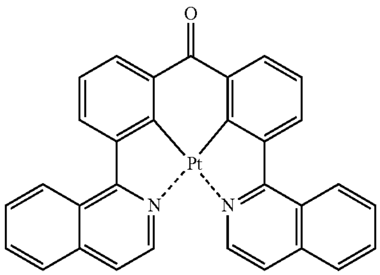
-continued
D11
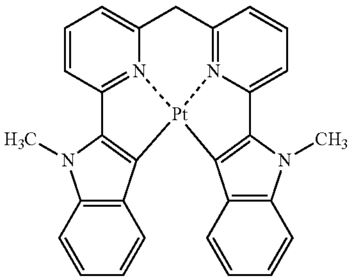
D12
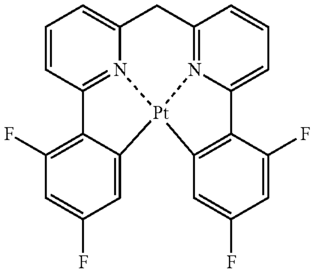
D13
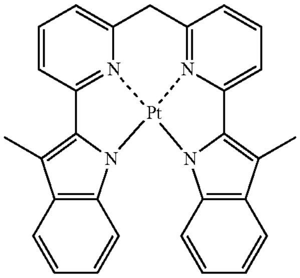
D14
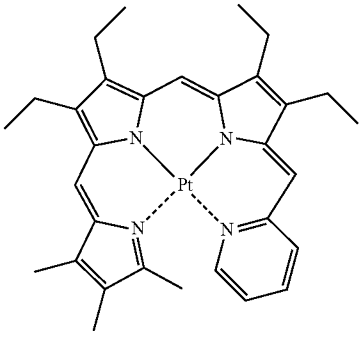
D15
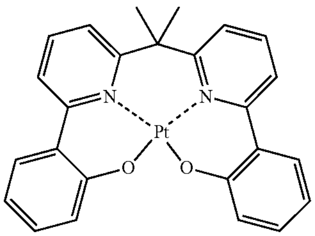

-continued
D16
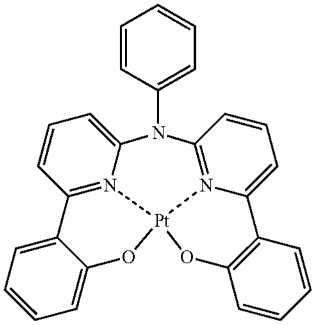
D17
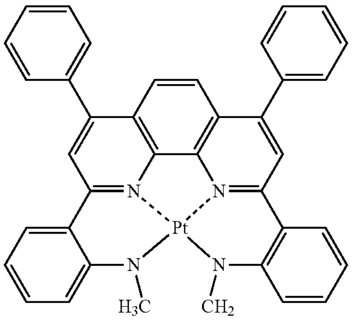
D18
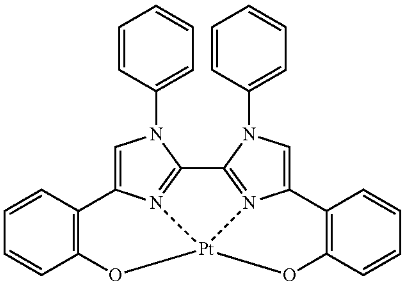
D19
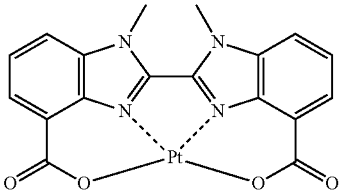
D20
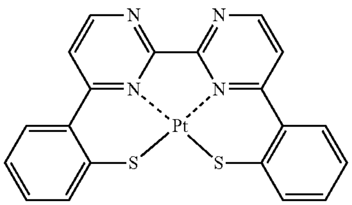
-continued
D21
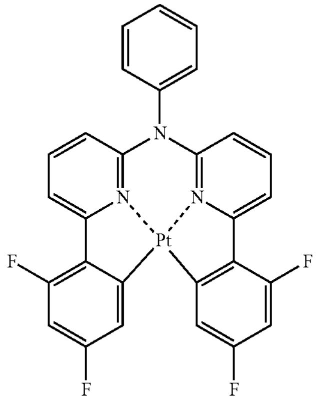
D22
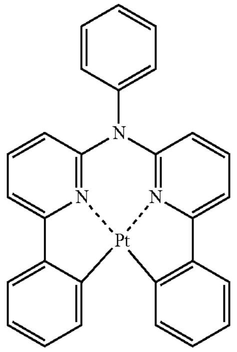
D23
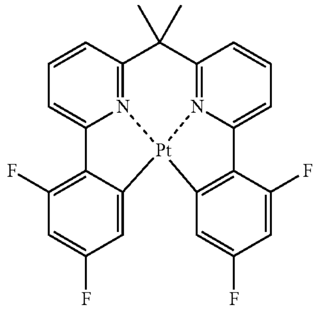
D24
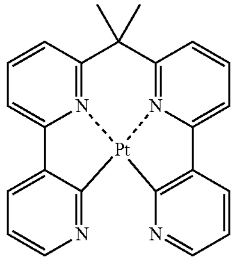
D25
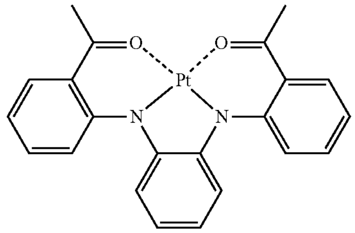

-continued
D26
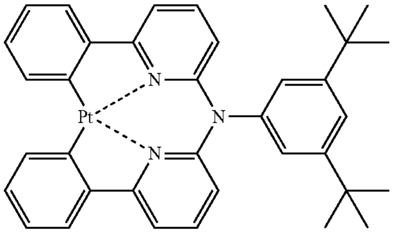
D27
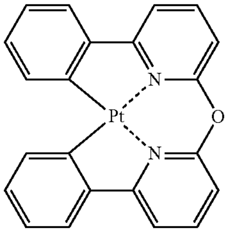
D28
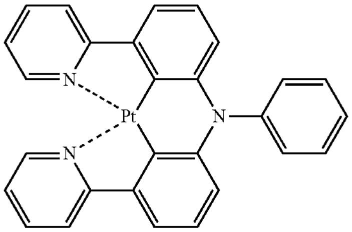
D29
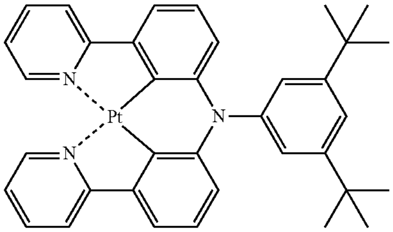
D30
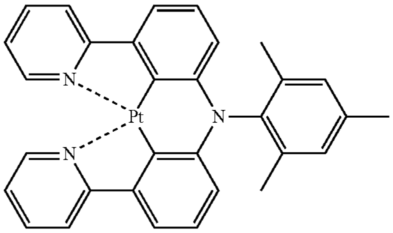
D31
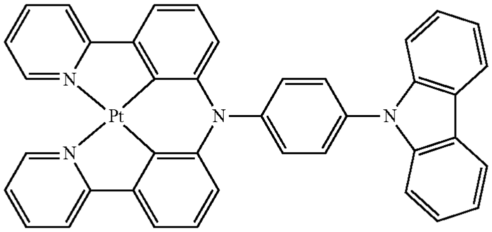
-continued
D32
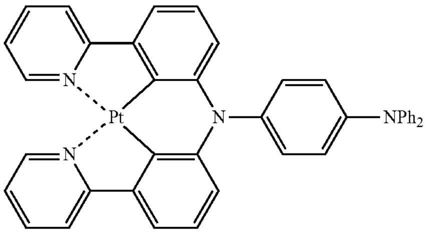
D33
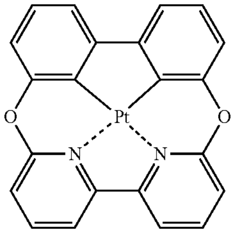
D34
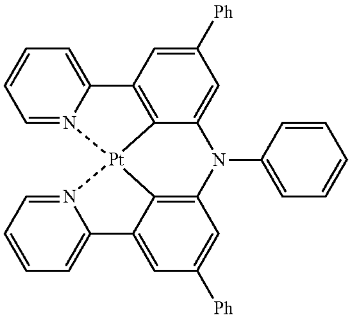
D35
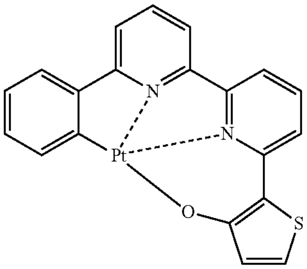
D36
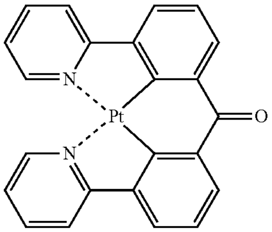

-continued
D37
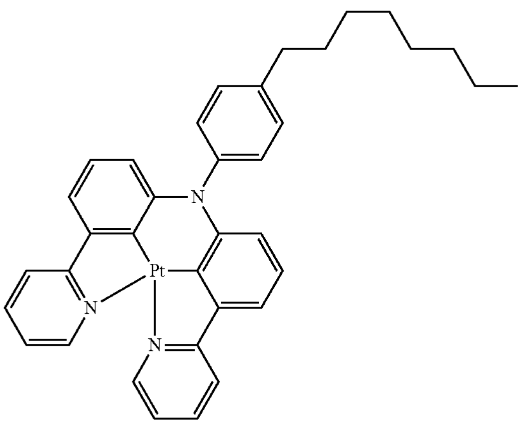
D38
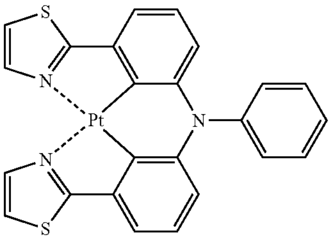
D39
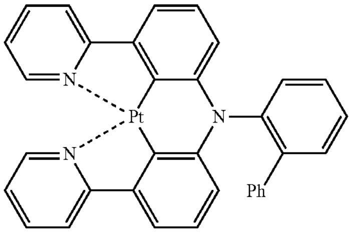
D40
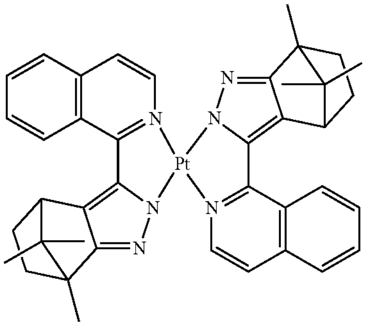
D41
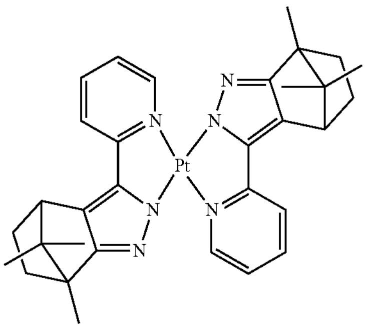
-continued
D42
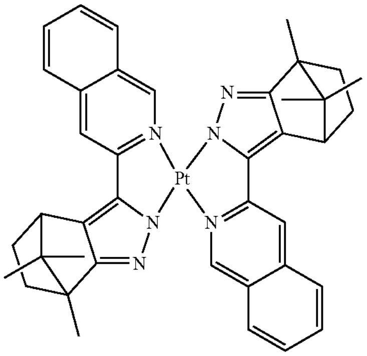
D43
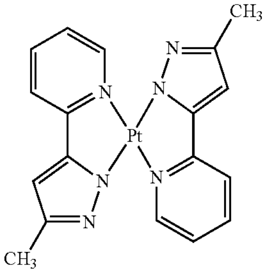
D44
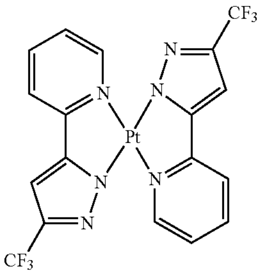
D45
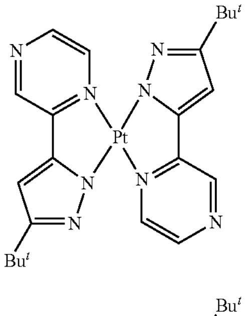
D46
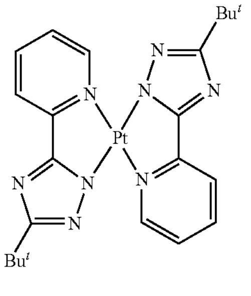

-continued

D47

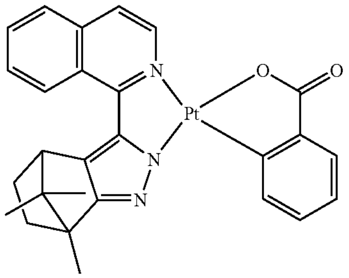

D48

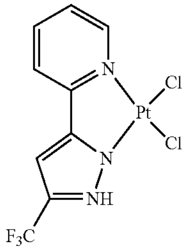

D49

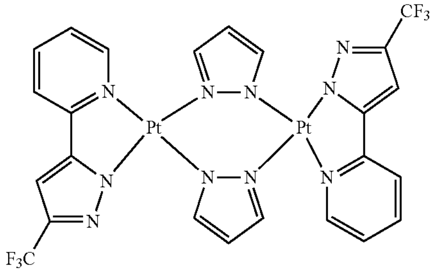

D50

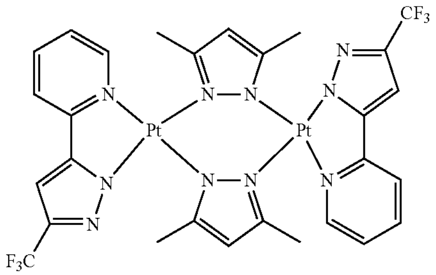

In addition, the dopant used in the EML may be an Os-complex, non-limiting examples of which include the following compounds.

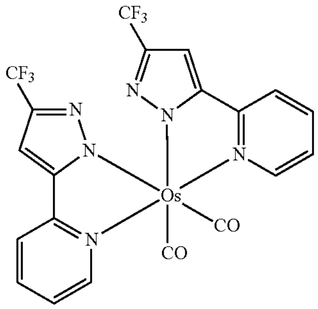

$Os(fppz)_2(CO)_2$

-continued

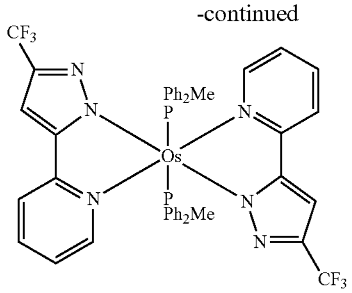

$Os(fppz)_2(PPh_2Me)_2$

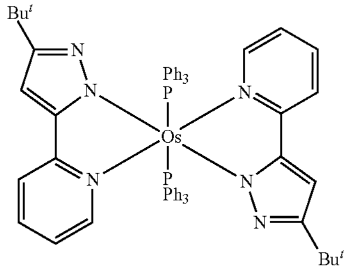

$Os(bppz)_2(PPh_3)_2$

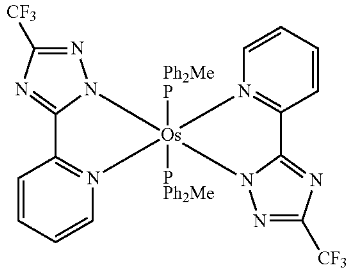

$Os(fptz)_2(PPh_2Me)_2$

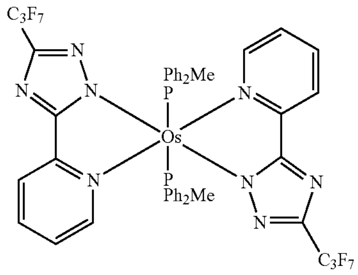

$Os(hptz)_2(PPhMe)_2$

If the EML includes a host and a dopant, the amount of the dopant may be about 0.01 to about 15 parts by weight based on 100 parts by weight of the host, but the EML is not limited thereto.

The thickness of the EML may be about 100 Å to about 1000 Å, for example, about 200 Å to about 600 Å. When the thickness of the EML is within these ranges, the EML may have good light emitting ability without a substantial increase in driving voltage.

Then, the ETL may be formed on the EML by vacuum deposition, spin coating, casting, or the like. When the ETL is formed using vacuum deposition or spin coating, the deposition or coating conditions may be similar to those described above for formation of the HIL, although the deposition or coating conditions may vary according to the compound used to form the ETL. The material used to form the ETL may be any material capable of stably transporting electrons injected from the electron injecting electrode (cathode) and any suitable material may be used. Non-limiting examples of suitable electron transporting materials include quinoline derivatives, such as tris-(8-hydroxyquinoline) aluminum ($Alq_3$), TAZ, Balq, beryllium bis(benzoquinolin-10-olate) ($Balq_2$), ADN, Compound 201, and Compound 202.

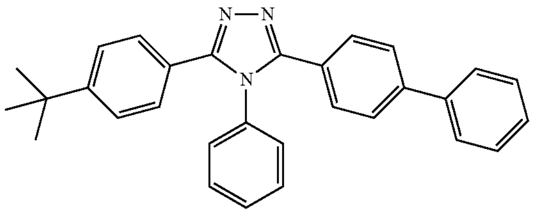

TAZ

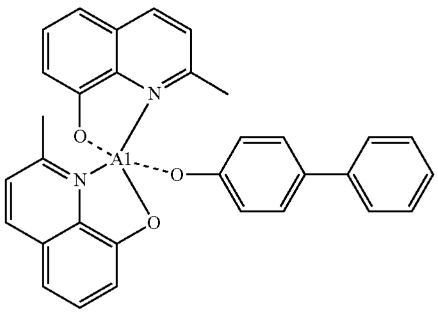

BAlq

Compound 201

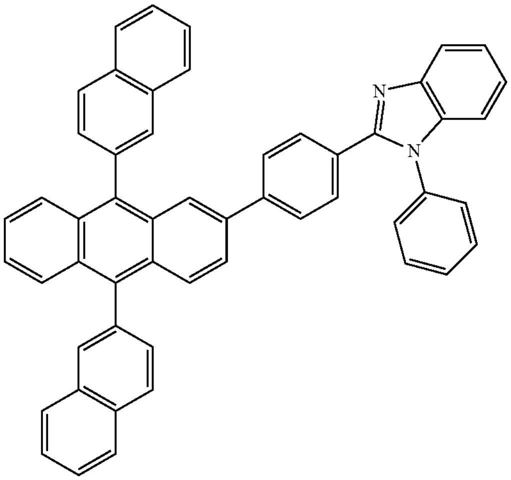

-continued

Compound 202

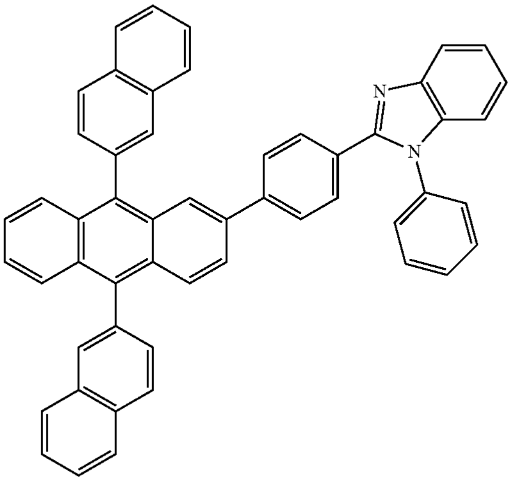

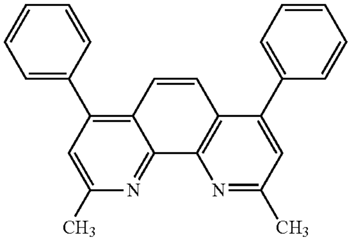

BCP

The thickness of the ETL may be about 100 Å to about 1,000 Å, for example, about 150 Å to about 500 Å. When the thickness of the ETL is within these ranges, the ETL may have good electron transporting ability without a substantial increase in driving voltage.

Alternatively, the ETL may further include a metal-containing material in addition to electron transporting organic compounds. The metal-containing material may include a Li complex. Non-limiting examples of the Li complex include lithium quinolate (LiQ) or Compound 203 below.

Compound 203

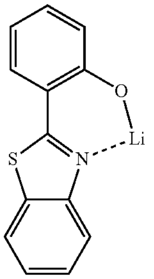

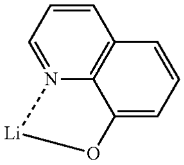

LiQ

In addition, the EIL may be formed on the ETL using any material that allows electrons to be easily injected from the cathode. Non-limiting examples of electron injecting materials include LiF, NaCl, CsF, $Li_2O$, and BaO. The conditions for deposition of the EIL may be similar to those described above for formation of the HIL, although the deposition conditions may vary according to the material used to form the EIL.

The thickness of the EIL may be about 1 to about 100 Å, for example, about 3 to about 90 Å. When the thickness of the EIL is within these ranges, the EIL may have good electron injecting ability without a substantial increase in driving voltage.

A second electrode 17 is disposed on the organic layer 15. The second electrode 17 may be a cathode, which is an electron injecting electrode. The material used to form the second electrode 17 may be a metal, an alloy, or an electrically conductive compound, all of which have low work functions, or a mixture thereof. For example, the second electrode 17 may be a transmissive electrode formed of lithium (Li), magnesium (Mg), aluminum (Al), an Al:Li alloy, calcium (Ca), a Mg:In alloy, or a Mg:Ag thin film. In order to manufacture a top-emission type organic light-emitting device, a transmissive electrode formed of ITO or IZO may be used, and various modifications may be applied thereto.

The organic light-emitting diode has been described with reference to FIG. 1, but the present invention is not limited thereto.

In addition, when a phosphorescent dopant is used to form the EML, in order to prevent diffusion of triplet excitons or holes into the ETL, an HBL may be formed between the HTL and the EML or between the H-functional layer and the EML by vacuum deposition, spin coating, casting, LB deposition, or the like. When the HBL is formed using vacuum deposition or spin coating, the conditions for deposition or coating may be similar to those described above for the formation of the HIL, although the conditions for deposition or coating may vary according to the material used to form the HBL. Any hole blocking material that is commonly used in the art may be used. Non-limiting examples of suitable hole blocking materials include oxadiazole derivatives, triazole derivatives, and phenanthroline derivatives. For example, BCP may be used as the hole blocking material.

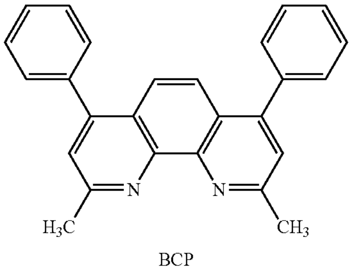

BCP

The thickness of the HBL may be about 20 to about 1,000 Å, for example, about 30 to about 300 Å. When the thickness of the HBL is within these ranges, the HBL may have good hole blocking ability without a substantial increase in driving voltage.

Hereinafter, one or more embodiments will be described with reference to the following examples. These examples are presented for illustrative purposes only, and are not intended to limit the purpose or scope of the one or more embodiments of the present invention.

Non-limiting examples of the unsubstituted $C_1$-$C_{60}$ alkyl group (or the $C_1$-$C_{60}$ alkyl group) include linear or branched $C_1$-$C_{60}$ alkyl groups, such as methyl, ethyl, propyl, isobutyl, sec-butyl, pentyl, iso-amyl, and hexyl. The substituted $C_1$-$C_{60}$ alkyl group refers to the substitution of at least one hydrogen atom of the alkyl group with:

a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group; or a $C_1$-$C_{60}$ alkyl group, a $C_2$-$C_{60}$ alkenyl group, a $C_2$-$C_{60}$ alkynyl group, or a $C_1$-$C_{60}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, or phosphoric acid group or a salt thereof; or a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group; or a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, or a $C_2$-$C_{60}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a triazinyl group, a quinolinyl group, or an isoquinolinyl group; or —$N(Q_{11})(Q_{12})$, and $Si(Q_{13})(Q_{14})(Q_{15})$, where $Q_{11}$ and $Q_{12}$ are each independently a $C_6$-$C_{60}$ aryl group or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

The unsubstituted $C_1$-$C_{60}$ alkoxy group (or the $C_1$-$C_{60}$ alkoxy group) may be represented by —OA, where A is an unsubstituted $C_1$-$C_{60}$ alkyl group. Non-limiting examples of the $C_1$-$C_{60}$ alkoxy group include methoxy, ethoxy, and isopropyloxy. The substituted $C_1$-$C_{60}$ alkoxy group refers to the substitution of at least one hydrogen atom of the alkoxy group with the substituents described above with respect to the substituted $C_1$-$C_{60}$ alkyl group.

The unsubstituted $C_2$-$C_{60}$ alkenyl group (or $C_2$-$C_{60}$ alkenyl group) refers to a hydrocarbon chain having at least one carbon-carbon double bond within or at a terminal end of the unsubstituted $C_2$-$C_{60}$ alkyl group. Non-limiting examples of the $C_2$-$C_{60}$ alkenyl group include ethenyl, propenyl, and butenyl. The substituted $C_2$-$C_{60}$ alkenyl group refers to the substitution of at least one hydrogen atom of the alkenyl group with the substituents described above with respect to the substituted $C_1$-$C_{60}$ alkyl group.

The unsubstituted $C_2$-$C_{60}$ alkynyl group (or the $C_2$-$C_{60}$ alkynyl group) refers to a hydrocarbon chain having at least one carbon-carbon triple bond within or at a terminal end of the unsubstituted $C_2$-$C_{60}$ alkyl group. Non-limiting examples of the $C_2$-$C_{60}$ alkenyl group include ethynyl and propynyl. The substituted $C_2$-$C_{60}$ alkynyl group refers to the substitution of at least one hydrogen atom of the alkynyl group with the substituents described above with respect to the substituted $C_1$-$C_{60}$ alkyl group.

The unsubstituted $C_6$-$C_{60}$ aryl group refers to a monovalent group having a $C_6$-$C_{60}$ carbocyclic aromatic system including at least one aromatic ring. The unsubstituted $C_6$-$C_{60}$ arylene group refers to a divalent group having a $C_6$-$C_{60}$ carbocyclic aromatic system including at least one aromatic ring. If the aryl group and arylene group include two or more rings, the rings may be fused to each other. The substituted $C_6$-$C_{60}$ aryl group and substituted $C_6$-$C_{60}$ arylene group refer to the substitution of at least one hydrogen atom of the aryl group and arylene group, respectively, with the substituents described above with respect to the substituted $C_1$-$C_{60}$ alkyl group.

Non-limiting examples of the substituted or unsubstituted $C_6$-$C_{60}$ aryl group include a phenyl group, a $C_1$-$C_{10}$ alkylphenyl group (e.g., ethylphenyl group), a $C_1$-$C_{10}$ alkylbiphenyl group (e.g., ethylbiphenyl group), a halophenyl group (e.g., o-, m-, or p-fluorophenyl group or dichlorophenyl group), a dicyanophenyl group, a trifluoromethoxyphenyl group, an o-, m-, or p-tolyl group, an o-, m-, or p-cumenyl group, a mesityl group, a phenoxyphenyl group, an (α,α-dimethylbenzene)phenyl group, an (N,N'-dimethyl)aminophenyl group, an (N,N'-diphenyl)aminophenyl group, a pentalenyl group, an indenyl group, a naphthyl group, a halonaphthyl group (e.g., fluoronaphthyl group), a $C_1$-$C_{10}$ alkylnaphthyl group (e.g., methylnaphthyl group), a $C_1$-$C_{10}$ alkoxynaphthyl group (e.g., methoxynaphthyl group), an anthracenyl group, an azulenyl group, a heptalenyl group, an acenaphthylenyl group, a phenalenyl group, a fluorenyl group, an anthraquinolinyl group, a methylanthracenyl group, a phenanthrenyl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Non-limiting examples of the substituted or unsubstituted $C_6$-$C_{60}$ arylene group may be easily derived from the examples of the substituted or unsubstituted $C_6$-$C_{60}$ aryl group.

The unsubstituted $C_2$-$C_{60}$ heteroaryl group is a monovalent group having at least one aromatic ring having at least one heteroatom selected from N, O, P, and S. The unsubstituted $C_2$-$C_{60}$ heteroarylene group is a divalent group having at least one aromatic ring having at least one of heteroatom selected from N, O, P, and S. When the heteroaryl group or the heteroarylene group has at least two rings, the rings may be fused to each other. The substituted $C_2$-$C_{60}$ heteroaryl group and substituted $C_2$-$C_{60}$ heteroarylene group refers to the substitution of at least one hydrogen atom of the heteroaryl and heteroarylene groups, respectively, with the substituents described above with respect to the substituted $C_1$-$C_{60}$ alkyl group.

Non-limiting examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Non-limiting examples of the unsubstituted $C_2$-$C_{60}$ heteroarylene group may be easily derived from the examples of the unsubstituted $C_2$-$C_{60}$ heteroaryl group.

The substituted or unsubstituted $C_6$-$C_{60}$ aryloxy group is —$OA_2$, where $A_2$ is a substituted or unsubstituted $C_6$-$C_{60}$ aryl group. The substituted or unsubstituted $C_6$-$C_{60}$ arylthio group is —$SA_3$, where $A_3$ is a substituted or unsubstituted $C_6$-$C_{60}$ aryl group.

EXAMPLES

Synthesis Example 1: Synthesis of Compound 1

Compound 1 was synthesized via Reaction Scheme 1 below.

Reaction Scheme 1

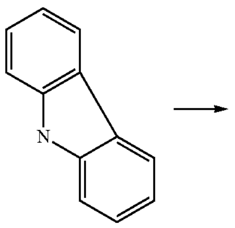

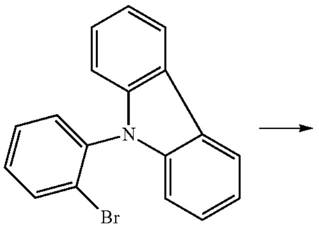

Intermediate 1-1

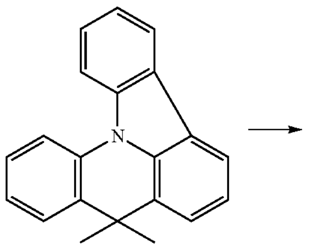

Intermediate 1-2

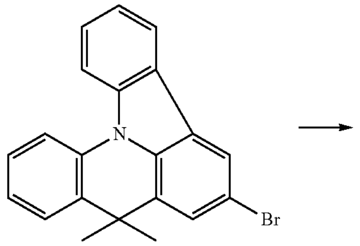

Intermediate 1-3

-continued

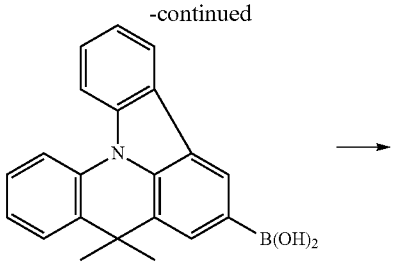

Intermediate 1-4

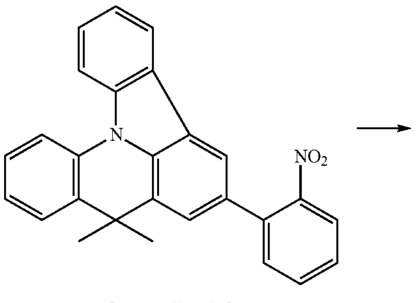

Intermediate 1-5

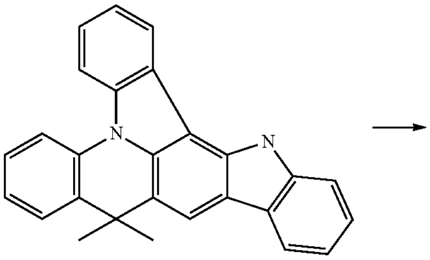

Intermediate 1-6

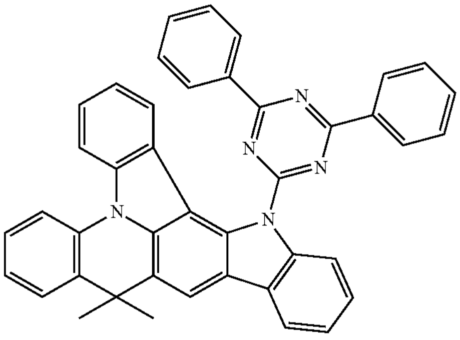

Compound 1

Synthesis of Intermediate 1-1

20 g (119.61 mmol) of carbazole, 67.68 g (239.22 mmol) of 2-bromoidobenzene, 11.40 g (59.81 mmol) of copper iodide, and 33.06 g (239.22 mmol) of potassium carbonate were dissolved in xylene in a nitrogen atmosphere, and the mixture was refluxed while stirring. After 12 hours, the mixture was cooled to room temperature, distilled water was added thereto, and the mixture was subjected to extraction using methyl chloride (MC), dried using magnesium sulfate, and distilled under reduced pressure. The resultant was separation-purified using column chromatography to obtain 32.64 g (101.67 mmol, 85% yield) of Intermediate 1-1.

Synthesis of Intermediate 1-2

20 g (62.30 mmol) of Intermediate 1-1 was dissolved in 100 ml of THF, and 24.91 ml (62.30 mmol, 2.5 M in hexane) of n-buLi was slowly added thereto at −78° C. After stirring for 2 hours, 4.70 ml (80.99 mmol) of acetone was added thereto, and the mixture was slowly heated to room temperature. Then, a $NaHCO_3$ aqueous solution was added thereto, and the mixture was subjected to extraction using MC. The resultant was dried using magnesium sulfate, distilled under reduced pressure, and added to a separate two-neck flask to be mixed with 100 ml of acetic acid. An HCl aqueous solution having the same amount as the catalyst (5 mol %, 12 N) was added thereto, and the mixture was refluxed while stirring. After 12 hours, the mixture was cooled to room temperature, and distilled water was added thereto. The mixture was subjected to extraction using MC, dried using magnesium sulfate, and distilled under reduced pressure. The resultant was separation-purified using column chromatography to obtain 11.47 g (40.50 mmol, 65% yield) of Intermediate 1-2.

Synthesis of Intermediate 1-3

20 g (70.64 mmol) of Intermediate 1-2 was dissolved in 200 ml of dimethylformamide (DMF), and then 13.83 g (77.70 mmol) of N-bromosuccinimide (NBS) was added thereto. After the mixture was stirred at room temperature for 10 hours, the organic solvent was distilled under reduced pressure, and distilled water was added thereto. Then, the resultant was subjected to extraction using ethyl acetate (EA). The resultant was dried using magnesium sulfate, distilled under reduced pressure, and separation-purified using column chromatography to obtain 22.19 g (61.45 mmol, 87% yield) of Intermediate 1-3.

Synthesis of Intermediate 1-4

20 g (55.39 mmol) of Intermediate 1-3 was dissolved in 200 ml of THF, and 22.15 ml (55.39 mmol, 2.5 M in hexane) of n-buLi was slowly added thereto at −78° C. After stirring for 1 hour, 8.02 ml (72.01 mmol) of trimethyl borate was added thereto, and the mixture was heated to room temperature and stirred for 12 hours. Distilled water was added thereto, and the mixture was subjected to extraction using EA, dried using magnesium sulfate, and distilled under reduced pressure. The resultant was separation-purified using column chromatography to obtain 10.87 g (33.24 mmol, 60% yield) of Intermediate 1-4.

Synthesis of Intermediate 1-5

20 g (61.14 mmol) of Intermediate 1-4, 14.81 g (73.36 mmol) of bromo-2-nitrobenzene, 1.78 g (1.53 mmol) of tetrakis(triphenylphosphine)palladium(0) ($Pd(PPh_3)_4$), 49.98 ml (101.89 mmol) of 2M $K_2CO_3$ aqueous solution, 160 ml of toluene, and 60 ml of ethanol were refluxed while stirring. After 4 hours, the mixture was cooled to room temperature, and distilled water was added thereto. The mixture was subjected to extraction using EA, dried using magnesium sulfate, and distilled under reduced pressure. The resultant was separation-purified using column chromatography to obtain 18.78 g (46.46 mmol, 76% yield) of Intermediate 1-5.

Synthesis of Intermediate 1-6

10 g (24.74 mmol) of Intermediate 1-5 was mixed with 100 ml of triethylphosphite, and the mixture was stirred at 180° C. After 10 hours, the mixture was cooled to room temperature, and the organic solvent was distilled under reduced pressure. Distilled water was added thereto, and the mixture was subjected to extraction using EA, dried using magnesium sulfate, and distilled under reduced pressure. The resultant was separation-purified using column chromatography to obtain 5.51 g (14.85 mmol, 60% yield) of Intermediate 1-6.

Synthesis of Compound 1

10 g (26.92 mmol) of Intermediate 1-6 was dissolved in 100 ml of DMF, and the solution was added to a reactor in which 1.62 g (40.38 mmol, 60% dispersion in mineral oil) of NaH was dissolved in 100 ml of DMF. After one hour, 8.65 g (32.31 mmol) of 2-chloro-4,6-diphenyltriazine dissolved in 100 ml of DMF was added thereto. The mixture was stirred for 12 hours, and then distilled water was added thereto to obtain a solid. The solid was filtered under reduced pressure and recrystallized using EA and DMF to obtain 8.77 g (14.54 mmol, 54% yield) of Compound 1.

MS: m/z 603.24 $[M]^+$ $^1$H NMR ($CDCl_3$) δ 8.55 (1H), 8.32 (1H), 8.28 (4H), 8.12 (1H), 7.94 (1H), 7.63 (1H), 7.51 (4H), 7.50 (1H), 7.41 (2H), 7.40 (1H), 7.37 (1H), 7.33 (1H), 7.30 (1H), 7.29 (1H), 7.26 (1H), 7.25 (1H), 1.72 (6H)

Synthesis Example 2: Synthesis of Compound 2

Compound 2 was prepared with a yield of 52% in the same manner as in Synthesis Example 1, except that benzophenone was used instead of acetone in the synthesis of Intermediate 1-2.

MS m/z 727.27 $[M]^+$ $^1$H NMR ($CDCl_3$) δ 8.55 (1H), 8.28 (4H), 8.25 (1H), 8.12 (1H), 7.94 (1H), 7.63 (1H), 7.51 (4H), 7.50 (1H), 7.41 (2H), 7.39 (1H), 7.33 (6H), 7.29 (1H), 7.26 (2H), 7.25 (1H), 7.23 (1H), 7.22 (1H), 7.11 (4H)

Synthesis Example 3: Synthesis of Compound 3

Compound 3 was synthesized via Reaction Scheme 2 below.

Reaction Scheme 2

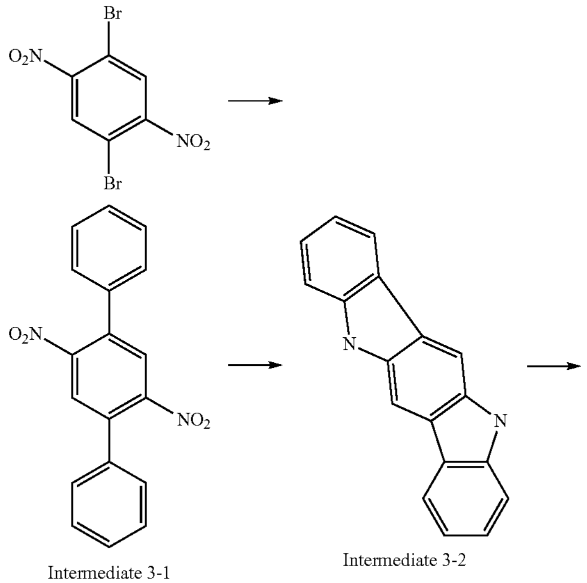

Intermediate 3-1

Intermediate 3-2

-continued

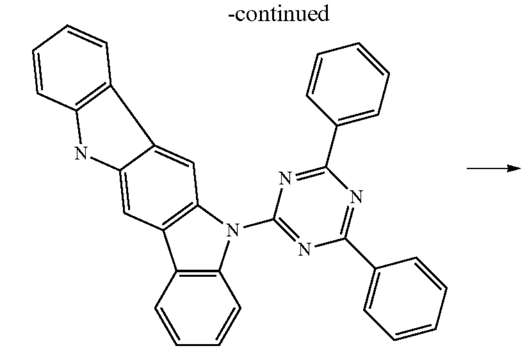

Intermediate 3-3

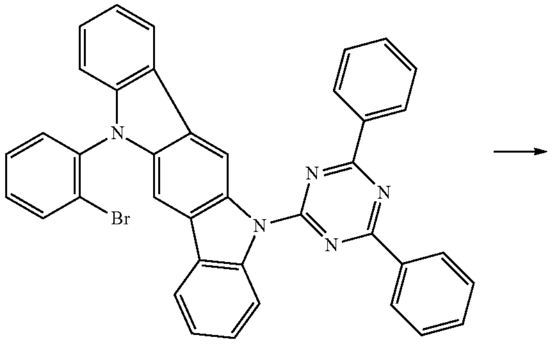

Intermediate 3-4

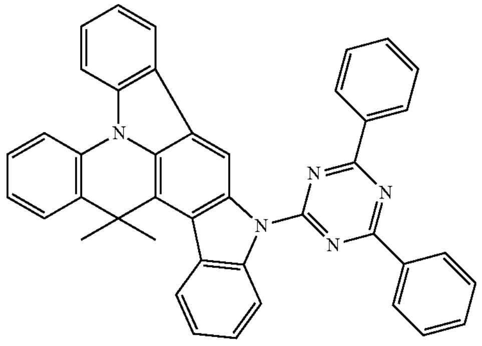

Compound 3

Synthesis of Intermediate 3-1

20 g (61.76 mmol) of 1,4-dibromo-2,5-dinitro benzene, 18.83 g (154.40 mmol) of 1-phenylboronic acid, 4.32 g (3.71 mmol) of $Pd(PPh_3)_4$, 90.88 ml (185.28 mmol) of 2M $K_2CO_3$ aqueous solution, 200 ml of toluene, and 100 ml of ethanol were mixed and refluxed while stirring. After 10 hours, the mixture was cooled to room temperature, and distilled water was added thereto. The mixture was subjected to extraction using EA, dried using magnesium sulfate, and distilled under reduced pressure. The resultant was separation-purified using column chromatography to obtain 17.79 g (55.58 mmol, 90% yield) of Intermediate 3-1.

Synthesis of Intermediate 3-2

Intermediate 3-2 was prepared in the same manner as in the synthesis of Intermediate 1-6 of Synthesis Example 1, except that Intermediate 3-1 was used instead of Intermediate 1-5.

Synthesis of Intermediate 3-3

Intermediate 3-3 was prepared in the same manner as in the synthesis of Compound 1 of Synthesis Example 1, except that Intermediate 3-2 was used instead of Intermediate 1-6.

Synthesis of Intermediate 3-4

Intermediate 3-4 was prepared in the same manner as in the synthesis of Intermediate 1-1 of Synthesis Example 1, except that Intermediate 3-3 was used instead of carbazole.

Synthesis of Compound 3

Compound 3 was prepared with a yield of 56% in the same manner as in the synthesis of Intermediate 1-2 of Synthesis Example 1, except that Intermediate 1-1 was used instead of Intermediate 3-4.

MS: m/z 603.24 $[M]^+$ $^1$H NMR ($CDCl_3$) δ 8.55 (1H), 8.28 (4H), 8.12 (1H), 7.94 (1H), 7.63 (1H), 7.51 (4H), 7.50 (1H), 7.41 (2H), 7.40 (1H), 7.37 (2H), 7.33 (1H), 7.30 (1H), 7.29 (1H), 7.26 (1H), 7.25 (1H), 1.72 (6H)

Synthesis Example 4: Synthesis of Compound 4

Compound 4 was prepared with a yield of 60% in the same manner as Synthesis Example 1, except that 2-(4-chlorophenyl)-4,6-diphenyl-triazine was used instead of 2-chloro-4,6-diphenyl-triazine in the synthesis of Compound 1.

MS: m/z 679.27 $[M]^+$ $^1$H NMR ($CDCl_3$) δ 8.55 (1H), 8.32 (1H), 8.28 (4H), 8.12 (1H), 7.94 (1H), 7.79 (2H), 7.68 (2H), 7.63 (1H), 7.51 (4H), 7.50 (1H), 7.41 (2H), 7.40 (1H), 7.37 (1H), 7.33 (1H), 7.30 (1H), 7.29 (1H), 7.26 (1H), 7.25 (1H), 1.72 (6H)

Synthesis Example 5: Synthesis of Compound 5

Compound 5 was prepared with a yield of 58% in the same manner as Synthesis Example 1, except that benzocarbazole was used instead of carbazole in the synthesis of Intermediate 1-1.

MS: m/z 653.26 $[M]^+$ $^1$H NMR ($CDCl_3$) δ 8.55 (1H), 8.32 (1H), 8.28 (4H), 8.16 (2H), 7.94 (1H), 7.67 (2H), 7.55 (1H), 7.51 (4H), 7.41 (2H), 7.40 (2H), 7.37 (1H), 7.33 (1H), 7.30 (1H), 7.26 (1H), 7.25 (1H), 1.72 (6H)

Synthesis Example 6: Synthesis of Compound 6

Compound 6 was prepared with a yield of 62% in the same manner as Synthesis Example 1, except that benzocarbazole was used instead of carbazole in the synthesis of Intermediate 1-1, and 2-chloro-4,6-diphenyl-pyrimidine was used instead of 2-chloro-4,6-diphenyl-triazine in the synthesis of Compound 1.

MS: m/z 652.26 $[M]^+$ $^1$H NMR ($CDCl_3$) δ 8.63 (1H), 8.55 (1H), 8.32 (1H), 8.16 (2H), 7.94 (1H), 7.79 (4H), 7.67 (2H), 7.55 (1H), 7.51 (4H), 7.40 (2H), 7.37 (1H), 7.33 (1H), 7.30 (1H), 7.26 (1H), 7.25 (1H), 1.72 (6H)

Synthesis Example 7: Synthesis of Compound 7

Compound 7 was prepared with a yield of 54% in the same manner as Synthesis Example 1, except that bromo-2-nitronaphthalene was used instead of bromo-2-nitrobenzene in the synthesis of Intermediate 1-5, and 2-chloro-4,6-diphenyl-pyrimidine was used instead of 2-chloro-4,6-diphenyl-triazine in the synthesis of Compound 1.

MS: m/z 652.26 $[M]^+$ $^1$H NMR ($CDCl_3$) δ 8.63 (1H), 8.54 (1H), 8.16 (1H), 8.12 (1H), 7.96 (1H), 7.94 (1H), 7.79 (4H), 7.67 (2H), 7.63 (1H), 7.51 (4H), 7.50 (1H), 7.41 (2H), 7.40 (1H), 7.37 (2H), 7.30 (1H), 7.29 (1H), 7.26 (1H), 1.72 (6H)

Synthesis Example 8: Synthesis of Compound 8

Compound 8 was prepared with a yield of 58% in the same manner as Synthesis Example 1, except that benzocarbazole was used instead of carbazole in the synthesis of Intermediate 1-1, and 2-(4-chlorophenyl)-4,6-diphenyl-pyrimidine was used instead of 2-chloro-4,6-diphenyl-triazine in the synthesis of Compound 1.

MS: m/z 728.29 $[M]^+$ $^1$H NMR ($CDCl_3$) δ 8.55 (1H), 8.32 (1H), 8.23 (1H), 8.16 (2H), 7.94 (1H), 7.79 (6H), 7.68 (2H), 7.67 (2H), 7.55 (1H), 7.51 (4H), 7.41 (2H), 7.40 (2H), 7.37 (1H), 7.33 (1H), 7.30 (1H), 7.26 (1H), 7.25 (1H), 1.72 (6H)

Synthesis Example 9: Synthesis of Compound 9

Compound 9 was prepared with a yield of 52% in the same manner as Synthesis Example 1, except that 2-bromoidonaphthalene was used instead of 2-bromoidobenzene in the synthesis of Intermediate 1-1, and 2-chloro-4,6-diphenyl-pyrimidine was used instead of 2-chloro-4,6-diphenyl-triazine in the synthesis of Compound 1.

MS: m/z 652.26 $[M]^+$ $^1$H NMR ($CDCl_3$) δ 8.63 (1H), 8.55 (1H), 8.32 (1H), 8.12 (1H), 8.01 (1H), 7.97 (1H), 7.94 (1H), 7.79 (4H), 7.77 (1H), 7.73 (1H), 7.63 (1H), 7.58 (1H), 7.55 (1H), 7.51 (4H), 7.50 (1H), 7.41 (2H), 7.33 (1H), 7.29 (1H), 7.25 (1H), 1.78 (6H)

Synthesis Example 10: Synthesis of Compound 10

Compound 10 was synthesized via Reaction Scheme 3 below.

Reaction Scheme 3

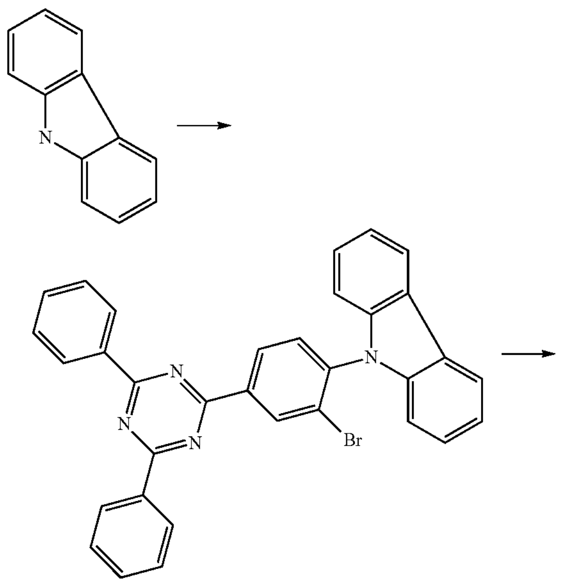

Intermediate 10-1

-continued

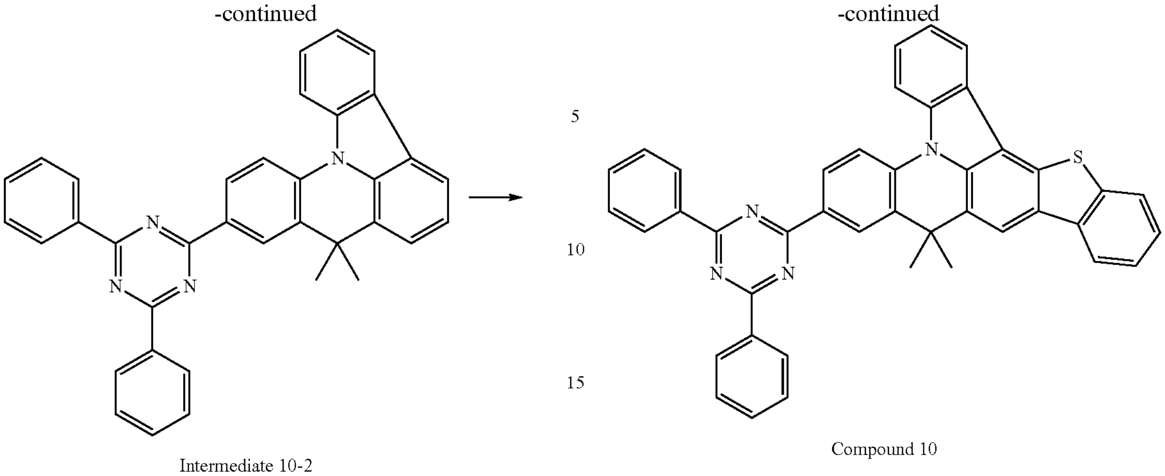

Intermediate 10-2

Compound 10

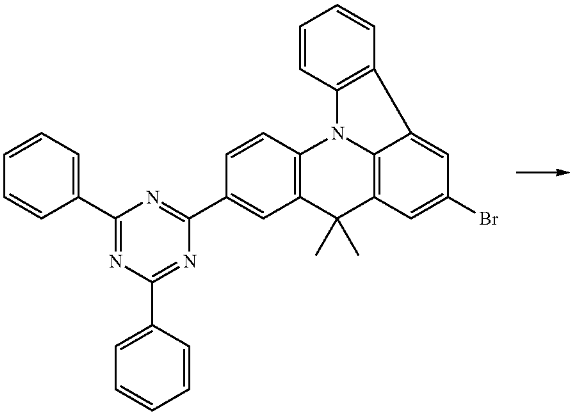

Intermediate 10-3

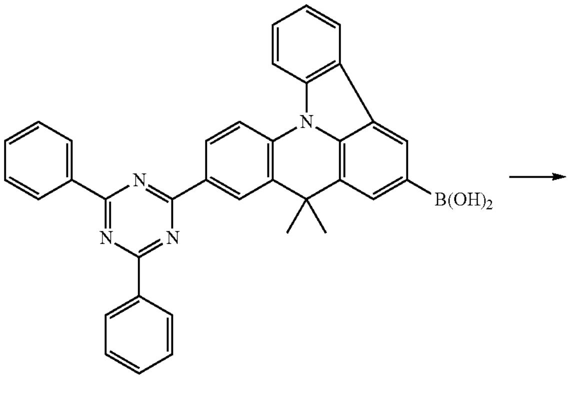

Intermediate 1-4

Synthesis of Intermediate 10-1

Intermediate 10-1 was prepared in the same manner as in the synthesis of Intermediate 1-1 of Synthesis Example 1, except that 2-(3-bromo-4-idophenyl)-4,6-diphenyl-1,3,5-triazine was used instead of 2-bromoidobenzene.

Synthesis of Intermediates 10-2, 10-3, and 10-4

Intermediates 10-2, 10-3, and 10-4 were sequentially prepared in the same manner as in the synthesis of Intermediates 1-2, 1-3, and 1-4 of Synthesis Example 1, except that Intermediate 10-1 was used instead of Intermediate 1-1.

Synthesis of Compound 10

Compound 10 was prepared with a yield of 48% in the same manner as in the synthesis of Intermediate 1-5 of Synthesis Example 1, except that Intermediate 10-4 was used instead of Intermediate 1-4, and 2-bromobenzenethiol was used instead of bromo-2-nitrobenzene.

MS: m/z 620.20 [M]+

$^1$H NMR ($CDCl_3$) δ 8.45 (1H), 8.28 (4H), 8.12 (1H), 7.98 (1H), 7.86 (1H), 7.68 (1H), 7.63 (1H), 7.61 (1H), 7.60 (1H), 7.52 (1H), 7.51 (4H), 7.50 (2H), 7.41 (2H), 7.29 (1H), 1.72 (6H)

Synthesis Example 11: Synthesis of Compound 11

Compound 11 was prepared with a yield of 50% in the same manner as Synthesis Example 10, except that 2-bromophenol was used instead of 2-bromobenzenethiol in the synthesis of Compound 10.

MS: m/z 604.23 $[M]^+$ $^1$H NMR ($CDCl_3$) δ 8.28 (4H), 8.12 (1H), 7.89 (1H), 7.86 (1H), 7.66 (1H), 7.63 (1H), 7.61 (1H), 7.60 (1H), 7.51 (4H), 7.50 (1H), 7.41 (2H), 7.38 (1H), 7.36 (1H), 7.32 (1H), 7.29 (1H), 1.72 (6H)

Synthesis Example 12: Synthesis of Compound 12

Compound 12 was prepared with a yield of 48% in the same manner as Synthesis Example 10, except that benzocarbazole was used instead of carbazole, and 2-(3-bromo-4-idophenyl)-4,6-diphenylpyrimidine was used instead of 2-(3-bromo-4-idophenyl)-4,6-diphenyl-1,3,5-triazine in the synthesis of Intermediate 10-1.

MS: m/z 669.22 $[M]^+$ $^1$H NMR ($CDCl_3$) δ 8.45 (1H), 8.23 (1H), 8.16 (2H), 7.98 (1H), 7.86 (1H), 7.79 (4H), 7.68 (1H), 7.67 (2H), 7.61 (1H), 7.60 (1H), 7.55 (1H), 7.52 (1H), 7.51 (4H), 7.50 (1H), 7.41 (2H), 7.40 (1H), 1.72 (6H)

Synthesis Example 13: Synthesis of Compound 13

Compound 13 was prepared with a yield of 52% in the same manner as Synthesis Example 10, except that benzocarbazole and 2-(3-bromo-4-idophenyl)-4,6-diphenylpyrimidine were used instead of carbazole and 2-(3-bromo-4-idophenyl)-4,6-diphenyl-1,3,5-triazine, respectively, in the synthesis of Intermediate 10-1, and 2-bromophenol was used instead of 2-bromobenzenthiol in the synthesis of Compound 10.

MS: m/z 653.25 $[M]^+$ $^1$H NMR ($CDCl_3$) δ 8.23 (1H), 8.16 (2H), 7.89 (1H), 7.86 (1H), 7.79 (4H), 7.67 (2H), 7.66 (1H), 7.61 (1H), 7.60 (1H), 7.55 (1H), 7.51 (4H), 7.41 (2H), 7.40 (1H), 7.38 (1H), 7.36 (1H), 7.32 (1H), 1.72 (6H)

Example 1

An ITO glass substrate (50×50 mm, 15 $\Omega/cm^2$), as a glass substrate for an organic light-emitting diode (OLED), manufactured by Samsung-Corning was ultrasonically cleaned using distilled water and then isopropanol, and then cleaned using UV/ozone for 30 minutes. The cleaned glass substrate to which a transparent electrode line is attached was installed on a substrate holder of a vacuum deposition apparatus, and 4,4',4"-tris(N-(2-naphthyl)-N-phenyl-amino)-triphenylamine (2T-NATA) was deposited (using a resistance heating deposition method) on an ITO electrode (anode) to form an HIL with a thickness of 60 nm. N,N'-bis(naphthalen-1-yl)-N,N'-bis(phenyl)benzidine (NPB) was deposited on the HIL to form an HTL with a thickness of 20 nm, and Compound 1 (host) and tris(2-phenylpyridine) iridium (III) ($Ir(ppy)_3$) (dopant, 8 wt %) were co-deposited on the HTL to form an EML with a thickness of 30 nm. Then, tris-(8-hydroxyquinoline)aluminum-(III) ($Alq_3$) was deposited thereon to form an ETL with a thickness of 20 nm. 8-hydroxyquinolinolato-lithium (LiQ) was deposited on the ETL to form an EIL with a thickness of 1 nm, and Al was deposited on the EIL to form a cathode with a thickness of 100 m, thereby manufacturing an organic light-emitting diode.

Example 2

An organic light-emitting diode was manufactured as in Example 1, except that Compound 2 was used as a host instead of Compound 1 in forming the EML.

Example 3

An organic light-emitting diode was manufactured as in Example 1, except that Compound 3 was used as a host instead of Compound 1 in forming the EML.

Example 4

An organic light-emitting diode was manufactured as in Example 1, except that Compound 4 was used as a host instead of Compound 1 in forming the EML.

Example 5

An organic light-emitting diode was manufactured as in Example 1, except that Compound 10 was used as a host instead of Compound 1 in forming the EML.

Example 6

An organic light-emitting diode was manufactured as in Example 1, except that Compound 11 was used as a host instead of Compound 1 in forming the EML.

Comparative Example 1

An organic light-emitting diode was manufactured as in Example 1, except that CBP was used as a host instead of Compound 1 in forming the EML.

Comparative Example 2

An organic light-emitting diode was manufactured as in Example 1, except that Compound A was used as a host instead of Compound 1 in forming the EML.

Compound A

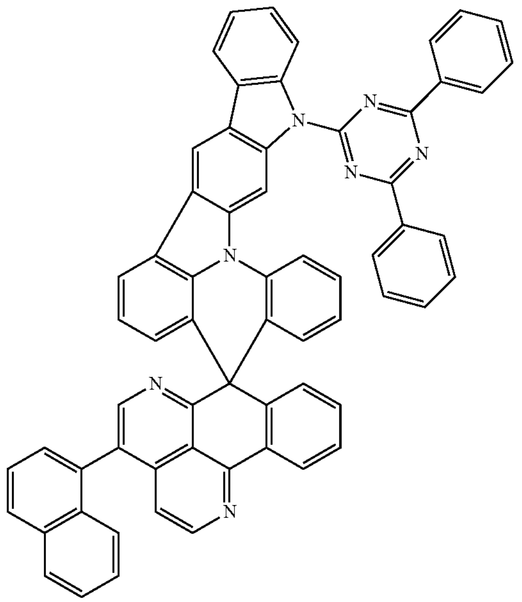

Example 7

An organic light-emitting diode was manufactured as in Example 1, except that Compound 5 was used as a host instead of Compound 1, and $Ir(piq)_2(acac)$ was used as a dopant instead of $Ir(ppy)_3$ in forming the EML.

Example 8

An organic light-emitting diode was manufactured as in Example 7, except that Compound 6 was used as a host instead of Compound 5 in forming the EML.

Example 9

An organic light-emitting diode was manufactured as in Example 7, except that Compound 7 was used as a host instead of Compound 5 in forming the EML.

Example 10

An organic light-emitting diode was manufactured as in Example 7, except that Compound 8 was used as a host instead of Compound 5 in forming the EML.

Example 11

An organic light-emitting diode was manufactured as in Example 7, except that Compound 9 was used as a host instead of Compound 5 in forming the EML.

Example 12

An organic light-emitting diode was manufactured as in Example 7, except that Compound 12 was used as a host instead of Compound 5 in forming the EML.

Example 13

An organic light-emitting diode was manufactured as in Example 7, except that Compound 13 was used as a host instead of Compound 5 in forming the EML.

Comparative Example 3

An organic light-emitting diode was manufactured as in Example 7, except that CBP was used as a host instead of Compound 5 in forming the EML.

Evaluation Example 1

Driving voltage, efficiency, and color purity of the organic light-emitting diodes manufactured according to Examples 1 to 13 and Comparative Examples 1 to 3 were measured according to the following methods, and the results are shown in Table 1 below.

Color coordinates: measured using a luminance meter (PR650 SpectraScan Colorimeter from Photo Research, Inc.) while supplying power by a current-voltmeter (SMU 236 from Keithley Instruments, Inc.).

Brightness: measured using a luminance meter (PR650 SpectraScan Colorimeter from Photo Research, Inc.) while supplying power by a current-voltmeter (SMU 236 from Keithley Instruments, Inc.).

Efficiency: measured using a luminance meter (PR650 SpectraScan Colorimeter from Photo Research, Inc.) while supplying power by a current-voltmeter (SMU 236 from Keithley Instruments, Inc.).

Lifespan 195 indicates the time (hr) it took for initial brightness (at 10 $mA/cm^2$), which was set as 100%, to decrease to 95%.

TABLE 1

| | EML | | Driving voltage | Efficiency | Color | Lifespan |
|---|---|---|---|---|---|---|
| | Host | Dopant | (V) | (Cd/A) | coordinates | T95 (hr) |
| Example 1 | Compound 1 | $Ir(ppy)_3$ | 6.2 | 29.5 | (0.282 to 0.607) | 190 |
| Example 2 | Compound 2 | $Ir(ppy)_3$ | 6.3 | 28.5 | (0.280 to 0.606) | 210 |
| Example 3 | Compound 3 | $Ir(ppy)_3$ | 6.1 | 29.3 | (0.280 to 0.606) | 220 |
| Example 4 | Compound 4 | $Ir(ppy)_3$ | 6.4 | 27.5 | (0.281 to 0.607) | 180 |
| Example 5 | Compound 10 | $Ir(ppy)_3$ | 6.6 | 27.2 | (0.282 to 0.606) | 160 |
| Example 6 | Compound 11 | $Ir(ppy)_3$ | 6.7 | 27.9 | (0.281 to 0.606) | 170 |
| Comparative Example 1 | CBP | $Ir(ppy)_3$ | 7.3 | 24.2 | (0.312 to 0.605) | 70 |
| Comparative Example 2 | Compound A | $Ir(ppy)_3$ | 7.8 | 21.5 | (0.320 to 0.602) | 120 |
| Example 5 | Compound 5 | $Ir(piq)_2(acac)$ | 6.4 | 12.5 | (0.642 to 0.352) | 480 |
| Example 6 | Compound 6 | $Ir(piq)_2(acac)$ | 5.5 | 14.3 | (0.645 to 0.350) | 520 |
| Example 7 | Compound 7 | $Ir(piq)_2(acac)$ | 5.8 | 13.9 | (0.646 to 0.350) | 470 |
| Example 8 | Compound 8 | $Ir(piq)_2(acac)$ | 6.0 | 12.8 | (0.646 to 0.349) | 450 |
| Example 9 | Compound 9 | $Ir(piq)_2(acac)$ | 5.7 | 13.5 | (0.645 to 0.350) | 480 |
| Example 10 | Compound 12 | $Ir(piq)_2(acac)$ | 5.8 | 13.4 | (0.645 to 0.350) | 440 |
| Example 11 | Compound 13 | $Ir(piq)_2(acac)$ | 6.0 | 125 | (0.645 to 0.350) | 420 |
| Comparative Example 3 | CBP | $Ir(piq)_2(acac)$ | 6.8 | 10.2 | (0.635 to 0.355) | 230 |

Referring to Table 1, the driving voltage, efficiency, and color purity of the organic light-emitting diodes manufactured according to Examples 1 to 6 were better than those of the organic light-emitting diodes manufactured according to Comparative Examples 1 and 2. Also, the driving voltage, efficiency, and color purity of the organic light-emitting diodes manufactured according to Examples 7 to 13 were better than those of the organic light-emitting diode manufactured according to Comparative Example 3.

As described above, according to one or more embodiments of the present invention, an organic light-emitting diode including the described condensed-cyclic compound may have low driving voltage, high efficiency, and high color purity.

While the present invention has been illustrated and described with reference to certain exemplary embodiments, those of ordinary skill in the art will understand that various modifications may be made to the described embodiments without departing from the spirit and scope of the present invention as defined by the following claims.

What is claimed is:

1. A condensed-cyclic compound represented by Formula 1:

Formula 1

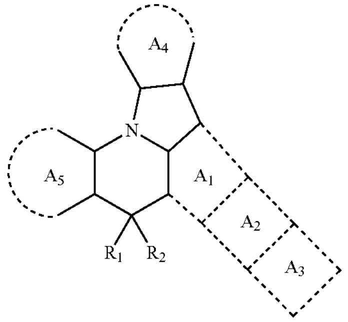

Formula 2

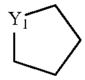

wherein:

ring $A_1$, ring $A_2$, and ring $A_3$ are condensed with each other;

ring $A_2$ is represented by Formula 2, wherein Y1 is $N-(L_1)_{aa}-(R_{11})_{ab}$;

ring $A_1$, ring $A_3$, ring $A_4$, and ring $A_5$ are each independently a substituted or unsubstituted benzene ring or a substituted or unsubstituted naphthalene ring;

$R_1$ and $R_2$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group, wherein $R_1$ and $R_2$ are non-ring forming substituents which are not linked to each other and do not form a ring;

$L_1$ is a substituted or unsubstituted $C_6$-$C_{60}$ arylene group or a substituted or unsubstituted $C_2$-$C_{60}$ heteroarylene group;

aa is an integer of 0 to 5;

$R_{11}$ is a substituted or unsubstituted 5-membered hetero ring, or a substituted or unsubstituted 6-membered hetero ring in which at least one ring-forming atom is nitrogen (N); and ab is an integer of 1 to 10.

2. The condensed-cyclic compound of claim 1, wherein the condensed-cyclic compound is represented by Formula 3 or 4:

Formula 3

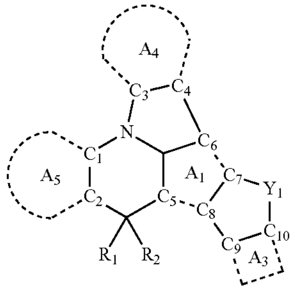

Formula 4

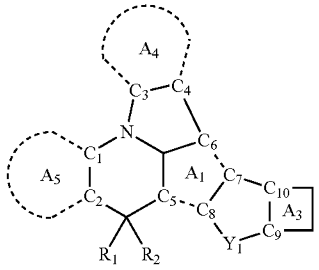

wherein $C_1$ to $C_{10}$ indicate distinct carbon atoms.

3. The condensed-cyclic compound of claim 2, wherein the ring $A_1$ is represented by one of Formulae 5(1) and 5(2), the ring $A_3$ is represented by one of Formulae 6(1) to 6(4), the ring $A_4$ is represented by one of Formulae 7(1) to 7(4), and the ring $A_5$ is represented by one of Formulae 8(1) to 8(4):

Formula 5(1)

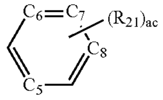

Formula 5(2)

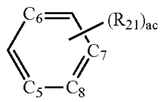

Formula 6(1)

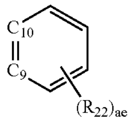

-continued

Formula 6(2)

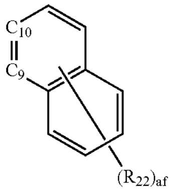

Formula 6(3)

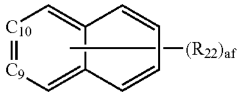

Formula 6(4)

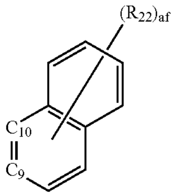

Formula 7(1)

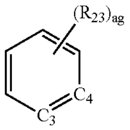

Formula 7(2)

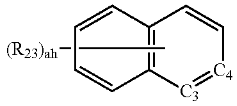

Formula 7(3)

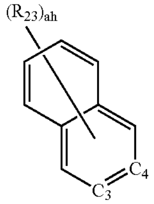

Formula 7(4)

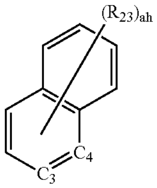

Formula 8(1)

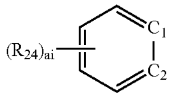

Formula 8(2)

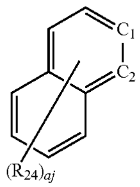

Formula 8(3)

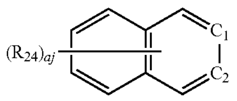

-continued

Formula 8(4)

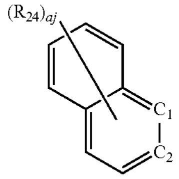

wherein:

$R_{21}$ to $R_{24}$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_2$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or $-(L_2)_{ao}-(R_{12})_{ap}$;

ac is 1 or 2;

ag is an integer of 1 to 3;

ae and ai are each independently an integer of 1 to 4;

ah is an integer of 1 to 5;

af and aj are each independently an integer of 1 to 6;

$L_2$ is a substituted or unsubstituted $C_6$-$C_{60}$ arylene group or a substituted or unsubstituted $C_2$-$C_{60}$ heteroarylene group;

ao is an integer of 0 to 5;

$R_{12}$ is a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, or a substituted or unsubstituted $C_2$-$C_{60}$ heteroaryl group; and ap is an integer of 1 to 10.

4. The condensed-cyclic compound of claim 3, wherein $R_{21}$ to $R_{24}$ are each independently:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, or a $C_1$-$C_{20}$ alkoxy group; or a $C_1$-$C_{20}$ alkyl group or a $C_1$-$C_{20}$ alkoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a $C_6$-$C_{14}$ aryl group or a $C_2$-$C_{14}$ heteroaryl group; or a $C_6$-$C_{14}$ aryl group or a $C_2$-$C_{14}$ heteroaryl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; or $-(L_2)_{ao}(R_{12})_{ap}$, wherein:

$L_2$ is a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group;

ao is 0, 1, or 2;

$R_{12}$ is a substituted or unsubstituted 5-membered hetero ring, a substituted or unsubstituted 6-membered hetero ring, a substituted or unsubstituted 9-membered hetero ring, or a substituted or unsubstituted 10-membered hetero ring, in which at least one ring-forming atom is nitrogen (N); and ap is 1 or 2.

5. The condensed-cyclic compound of claim 4, wherein $R_{21}$ to $R_{24}$ are each independently:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a hexyl group, a heptyl group, an octyl group, a methoxy group, an ethoxy group, a propoxy group, a butoxy group, or a pentoxy group; or a methyl group, an ethyl group, a propyl group, a butyl group, a pentyl group, a hexyl group, a heptyl group, an octyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a phenyl group, a naphthyl group, an anthracenyl group, a pyridinyl group, a pyrimidinyl group, a pyrazinyl group, or a triazinyl group; or a phenyl group, a naphthyl group, an anthracenyl group, a pyridinyl group, a pyrimidinyl group, a pyrazinyl group, or a triazinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; or $-(L_2)_{ao}-(R_{12})_{ap}$ wherein:

$L_2$ is:

a phenylene group, a naphthylene group, a fluorenylene group, or an anthracenylene group; or a phenylene group, a naphthylene group, a fluorenylene group, or an anthracenylene group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group;

ao is 0, 1, or 2;

$R_{12}$ is:

a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; and ap is 1 or 2.

6. The condensed-cyclic compound of claim 2, wherein the condensed-cyclic compound is represented by Formula 3, the ring $A_1$ is represented by one of Formulae 5(1) and 5(2), the ring $A_3$ is represented by one of Formulae 6(1) and 6(2), the ring $A_4$ is represented by one of Formulae 7(1) and 7(3), and the ring $A_5$ is represented by one of Formulae 8(1) and 8(3):

Formula 5(1)

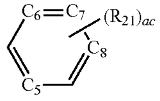

Formula 5(2)

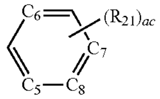

Formula 6(1)

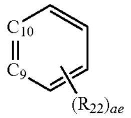

-continued

Formula 6(2)

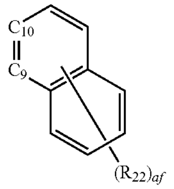

Formula 7(1)

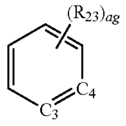

Formula 7(3)

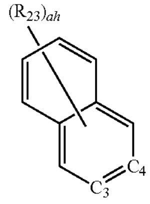

Formula 8(1)

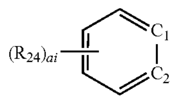

Formula 8(3)

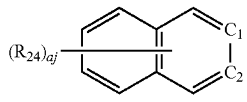

wherein:

ac is 1 or 2;

ag is an integer of 1 to 3;

ae and ai are each independently an integer of 1 to 4;

ah is an integer of 1 to 5;

af and aj are each independently an integer of 1 to 6;

$R_{21}$ to $R_{24}$ are each independently:

a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a methyl group, an ethyl group, a propyl group, a butyl group, a pentyl group, a hexyl group, a heptyl group, an octyl group, a methoxy group, an ethoxy group, a propoxy group, a butoxy group, or a pentoxy group; or a methyl group, an ethyl group, a propyl group, a butyl group, a pentyl group, a hexyl group, a heptyl group, an octyl group, a methoxy group, an ethoxy group, a propoxy group, a butoxy group, or a pentoxy group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a phenyl group, a naphthyl group, or an anthracenyl group; or a phenyl group, a naphthyl group, an anthracenyl group, a pyridinyl group, a pyrimidinyl group, a pyrazinyl group, or a triazinyl group; or a phenyl group, a naphthyl group, an anthracenyl group, a pyridinyl group, a pyrimidinyl group, a pyrazinyl group, or a triazinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; or $-(L_2)_{ao}-(R_{12})_{ap}$;

wherein:

$L_2$ is a phenylene group, a naphthylene group, a fluorenylene group, or an anthracenylene group; or a phenylene group, a naphthylene group, a fluorenylene group, or an anthracenylene group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group;

ao is 0, 1, or 2;

$R_{12}$ is a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; and ap is 1 or 2.

7. The condensed-cyclic compound of claim 1, wherein, in Formula 2, $Y_1$ is $N-(L_1)_{aa}-(R_{11})_{ab}$, wherein:

$L_1$ is a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group;

aa is 0, 1, or 2;

$R_{11}$ is a substituted or unsubstituted 5-membered hetero ring, a substituted or unsubstituted 6-membered hetero ring, a substituted or unsubstituted 9-membered hetero ring, or a substituted or unsubstituted 10-membered hetero ring in which at least one ring-forming atom is nitrogen (N); and ab is 1 or 2.

8. The condensed-cyclic compound of claim 7, wherein $R_{11}$ is:

a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group.

9. The condensed-cyclic compound of claim 7, wherein $R_{11}$ is represented by one of Formulae 9 to 15:

Formula 9

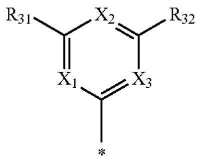

Formula 10

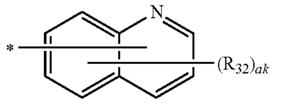

Formula 11

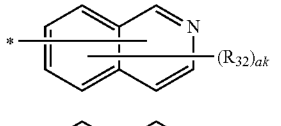

Formula 12

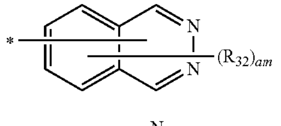

Formula 13

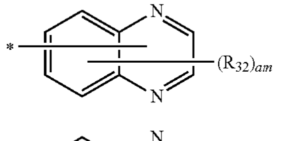

Formula 14

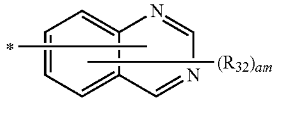

-continued

Formula 15

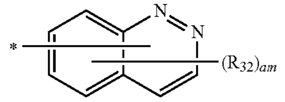

wherein:

$X_1$ is N or $C(R_{33})$, $X_2$ is N or $C(R_{34})$, and $X_3$ is N or $C(R_{35})$, wherein at least one of $X_1$, $X_2$, and $X_3$ is N;

$R_{31}$ to $R_{35}$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group;

ak is an integer from 1 to 6;

am is an integer from 1 to 5; and

* is a binding site to $L_1$ or nitrogen in $Y_1$.

10. The condensed-cyclic compound of claim 9, wherein, in Formula 9:

$X_1$, $X_2$ and $X_3$ are N; or $X_1$ and $X_3$ are N, and $X_2$ is $C(R_{34})$; or $X_1$ and $X_2$ are N, and $X_3$ is $C(R_{35})$.

11. The condensed-cyclic compound of claim 1, wherein $Y_1$ is S or O, and the ring $A_5$ is represented by one of Formulae 8(1) to 8(4):

Formula 8(1)

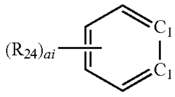

Formula 8(2)

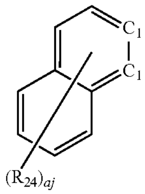

Formula 8(3)

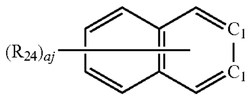

Formula 8(4)

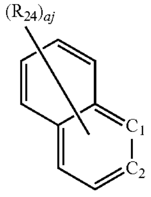

wherein:

$R_{24}$ is a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or $-(L_2)_{ao}-(R_{12})_{ap}$;

ai is an integer from 1 to 4;

aj is an integer from 1 to 6;

at least one of the $R_{24}$s of Formula 8(1) and at least one of the $R_{24}$s of Formulae 8(2) to 8(4) are $-(L_2)_{ao}-(R_{12})_{ap}$;

$L_2$ is a substituted or unsubstituted phenylene group, a substituted or unsubstituted naphthylene group, a substituted or unsubstituted a fluorenylene group, or a substituted or unsubstituted anthracenylene group;

ao is 0, 1, or 2;

$R_{12}$ is a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group; or a pyrrolyl group, a pyrazolyl group, an imidazolyl group, a pyridinyl group, a pyrazinyl group, a pyrimidinyl group, an indolyl group, a purinyl group, a benzoimidazolyl group, a quinolinyl group, an isoquinolinyl group, a phthalazinyl group, a quinoxalinyl group, a quinazolinyl group, or a cinnolinyl group substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, or an anthracenyl group; and ap is 1 or 2.

12. The condensed-cyclic compound of claim 1, wherein the condensed-cyclic compound is represented by one of Formulae 3-1 to 3-20:

Formula 3-1

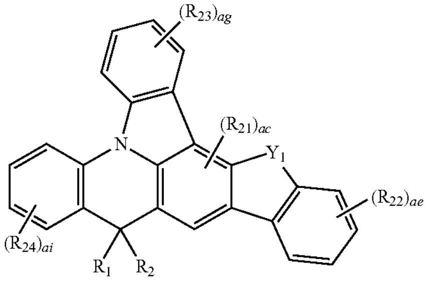

Formula 3-2

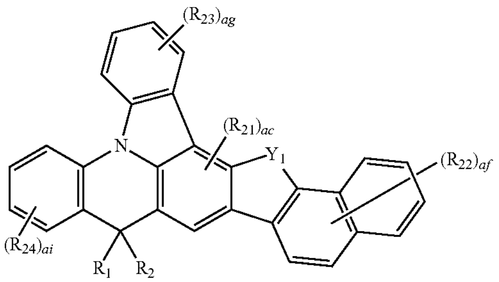

-continued

Formula 3-3

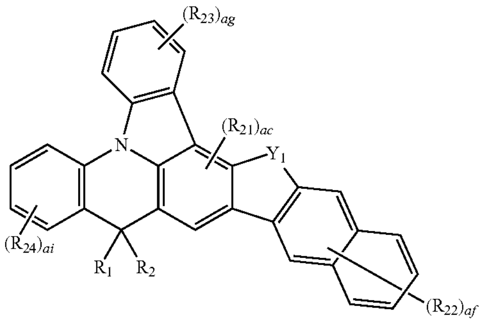

Formula 3-4

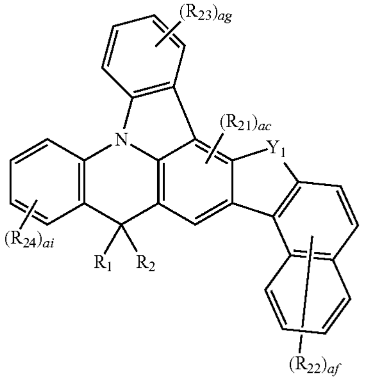

Formula 3-5

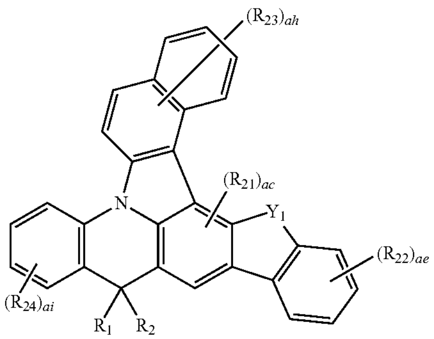

Formula 3-6

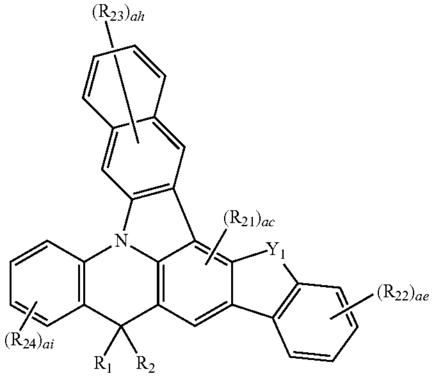

Formula 3-7
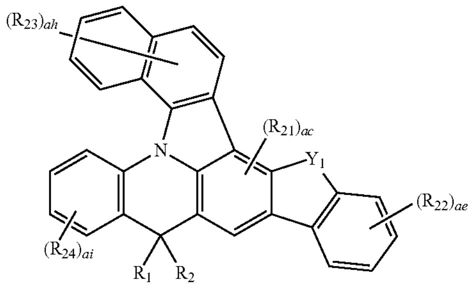
Formula 3-8
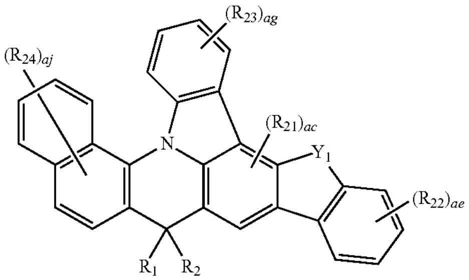
Formula 3-9
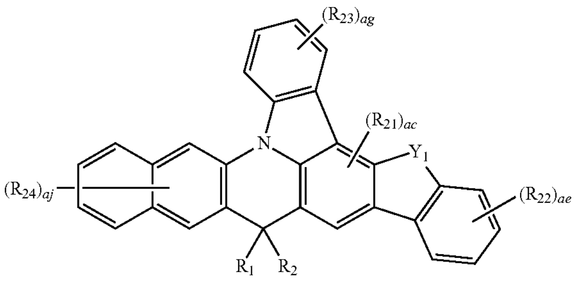
Formula 3-10
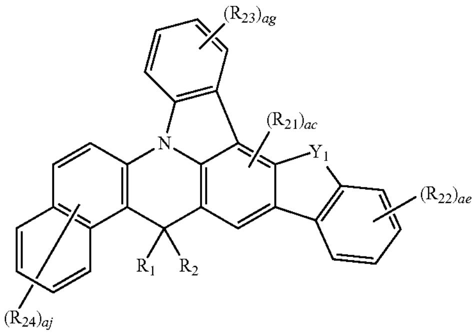
Formula 3-11
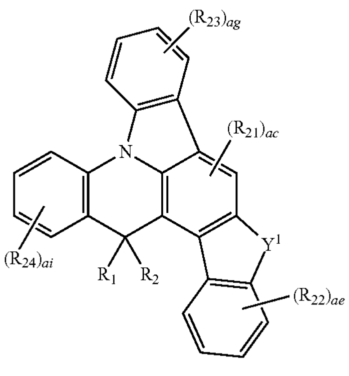
Formula 3-12
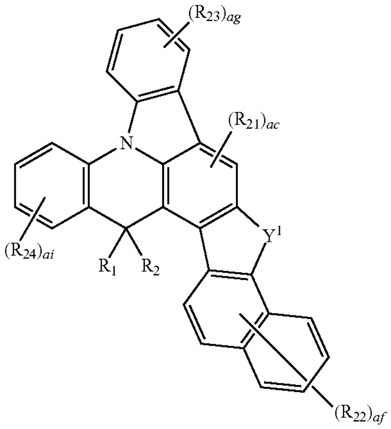
Formula 3-13
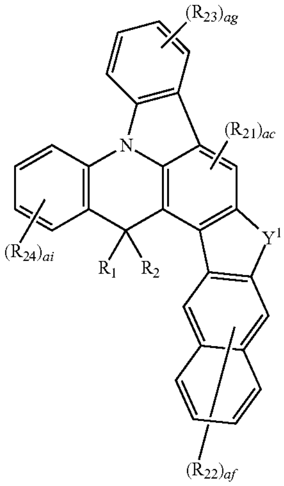
Formula 3-14
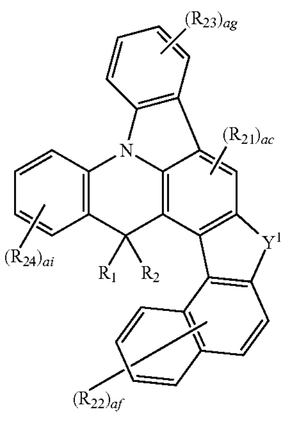

-continued

Formula 3-15

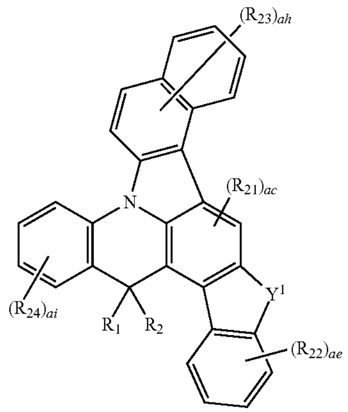

Formula 3-16

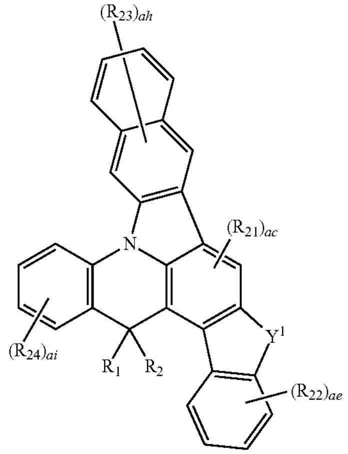

Formula 3-17

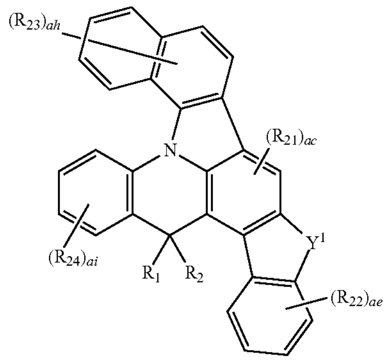

Formula 3-18

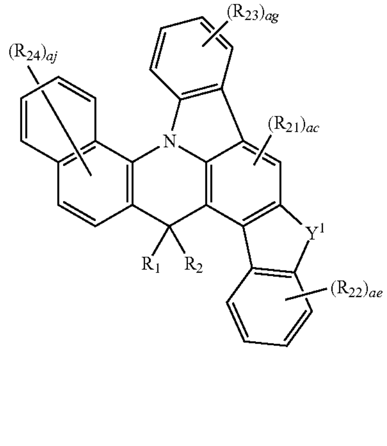

-continued

Formula 3-19

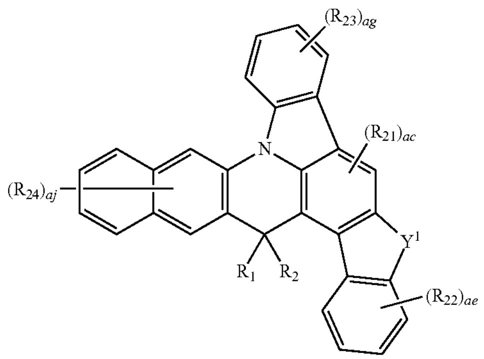

Formula 3-20

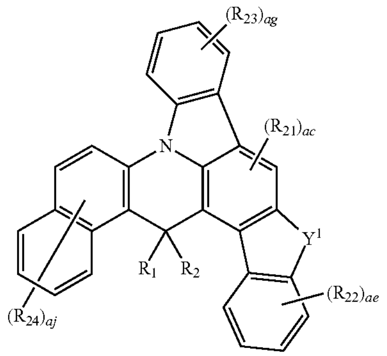

wherein:

$R_{21}$ to $R_{24}$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, or $-(L_2)ao-(R_{12})_{ap}$;

ac is 1 or 2;

ag is an integer of 1 to 3;

ad, ae, and ai are each independently an integer of 1 to 4;

ah is an integer of 1 to 5;

af and aj are each independently an integer of 1 to 6;

$L_2$ is a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted spiro-fluorenyl group, a substituted or unsubstituted phenalenylene group, a substituted or unsubstituted phenanthrenylene group, a substituted or unsubstituted anthracenylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, or a substituted or unsubstituted hexacenylene group;

ao is 0, 1, or 2;

$R_{12}$ is a substituted or unsubstituted 5-membered hetero ring, a substituted or unsubstituted 6-membered hetero ring, a substituted or unsubstituted 9-membered hetero ring, or a substituted or unsubstituted 10-membered hetero ring, in which at least one ring-forming atom is nitrogen (N); and ap is 1 or 2.

13. The condensed-cyclic compound of claim 12, wherein $Y_1$ is N-$(L_1)_{aa}$-$(R_{11})_{ab}$, and $R_{21}$ to $R_{24}$ are all hydrogen.

14. The condensed-cyclic compound of claim 12, wherein $Y_1$ is S or O, $R_{21}$ to $R_{24}$ are all hydrogen, ai and aj are 1, and $R_{24}$ is -$(L_2)_{ao}$-$(R_{12})_{ap}$.

15. The condensed-cyclic compound of claim 1, wherein the condensed-cyclic compound is represented by one of Formulae 4-1 to 4-20:

Formula 4-1

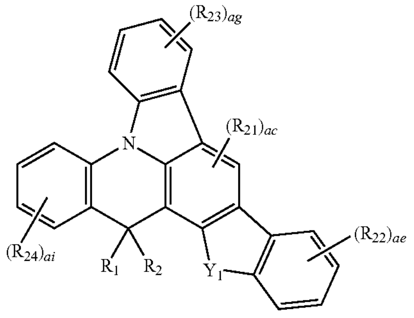

Formula 4-2

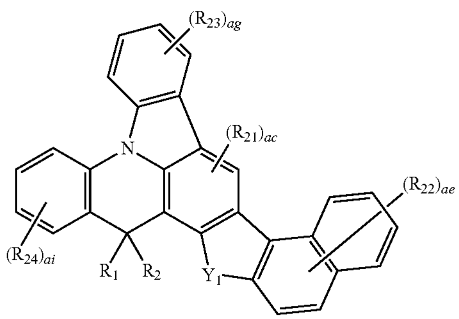

-continued

Formula 4-3

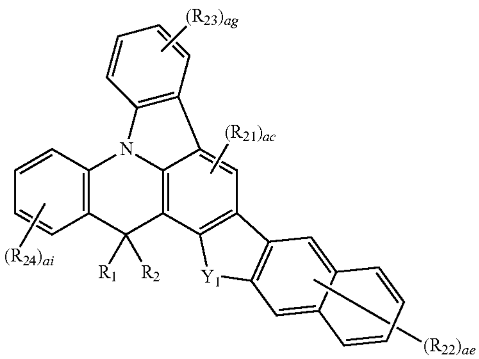

Formula 4-4

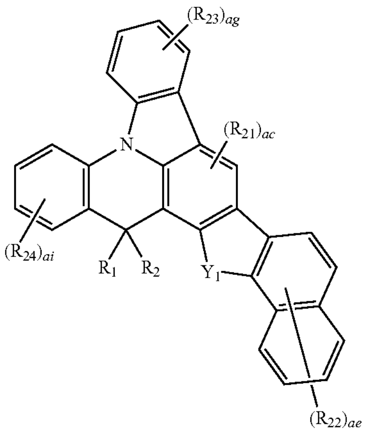

Formula 4-5

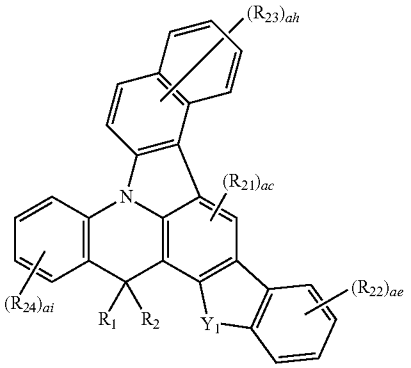

Formula 4-6

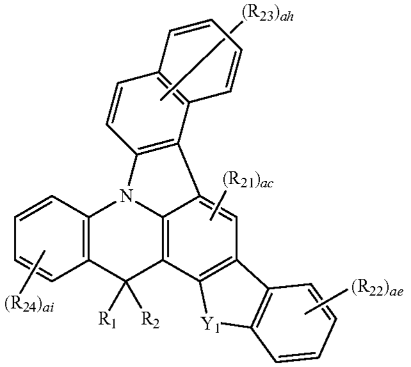

-continued
Formula 4-7
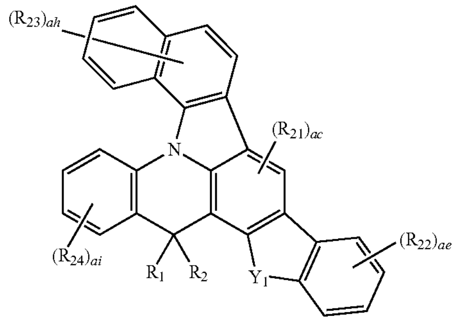
Formula 4-8
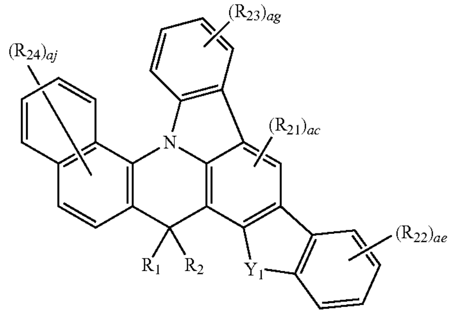
Formula 4-9
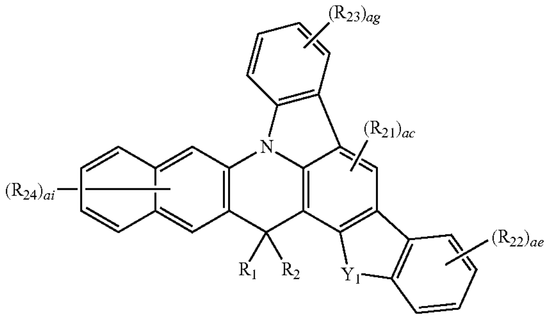
Formula 4-10
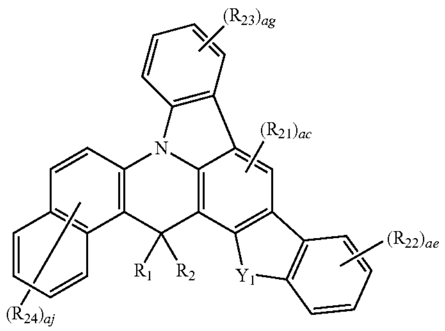
-continued
Formula 4-11
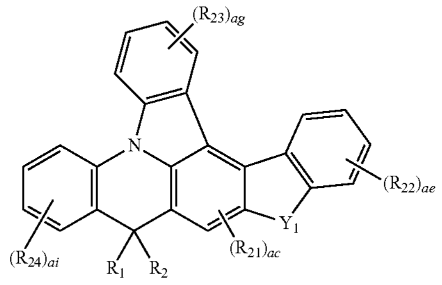
Formula 4-12
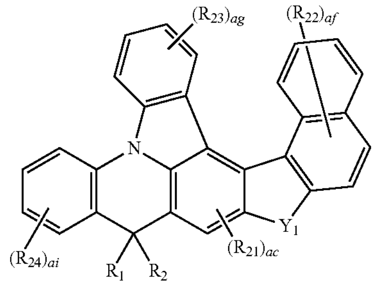
Formula 4-13
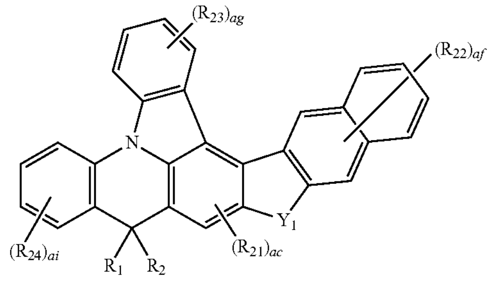
Formula 4-14
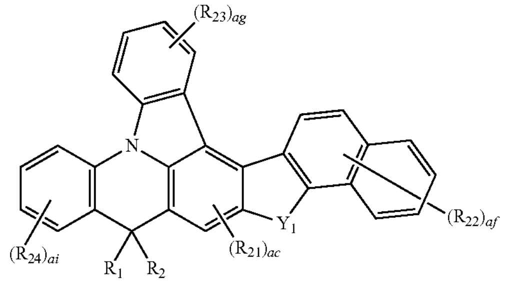
Formula 4-15
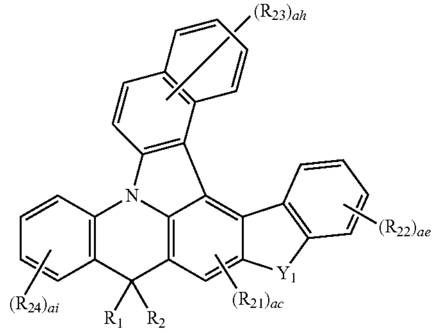

-continued

Formula 4-16

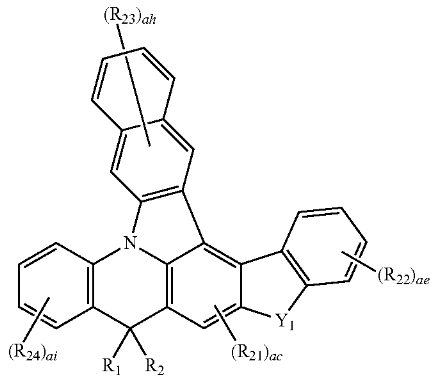

Formula 4-17

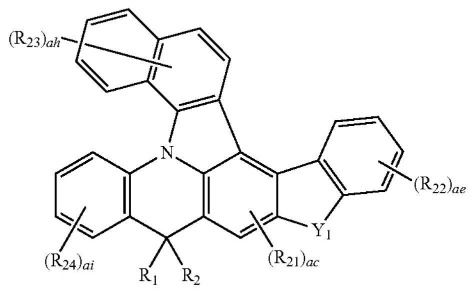

Formula 4-18

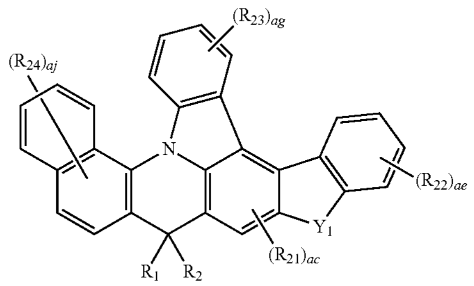

Formula 4-19

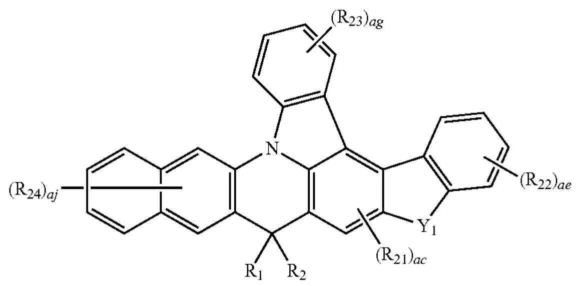

-continued

Formula 4-20

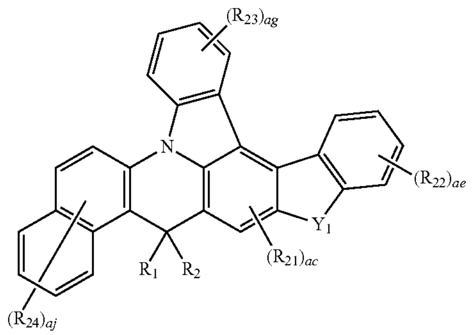

wherein:

$R_{21}$ to $R_{24}$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group;

ac is 1 or 2;

ag is an integer of 1 to 3;

ae and ai are each independently an integer of 1 to 4;

ah is an integer of 1 to 5; and af and aj are each independently an integer of 1 to 6.

16. A condensed-cyclic compound represented by one of Compounds 1 to 13:

1

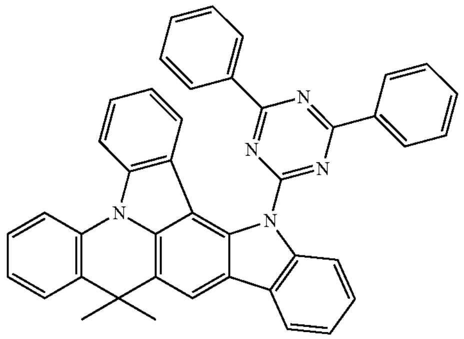

-continued
2
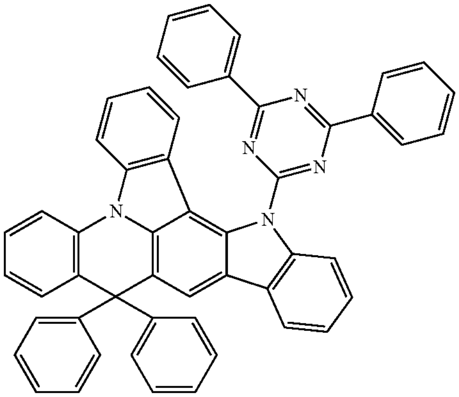
3
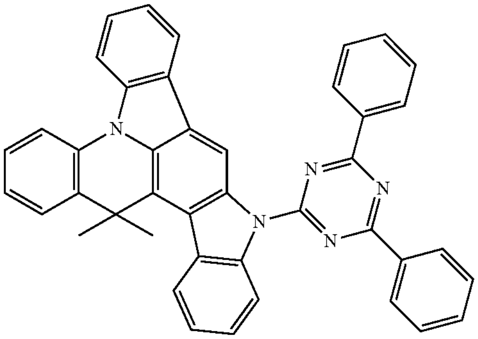
4
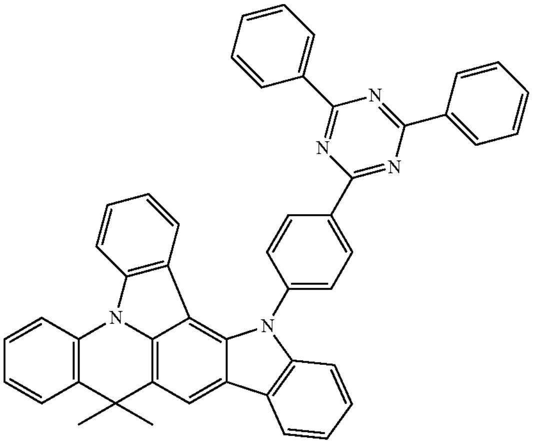
5
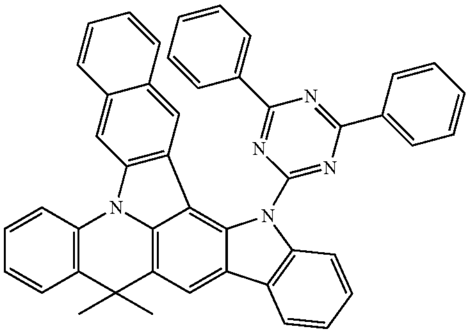
-continued
6
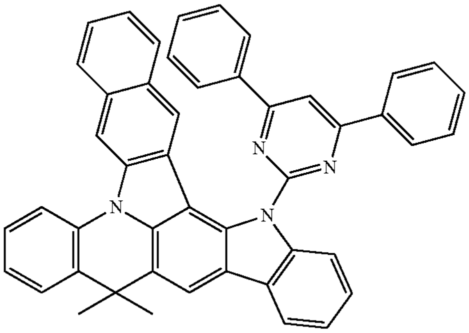
7
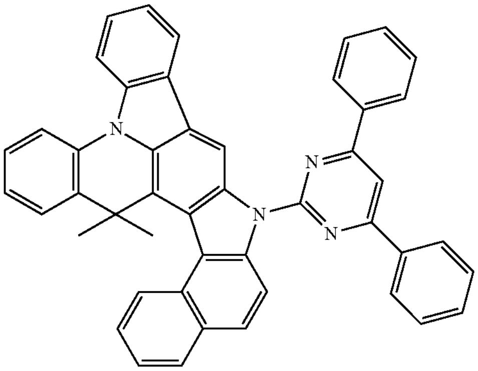
8
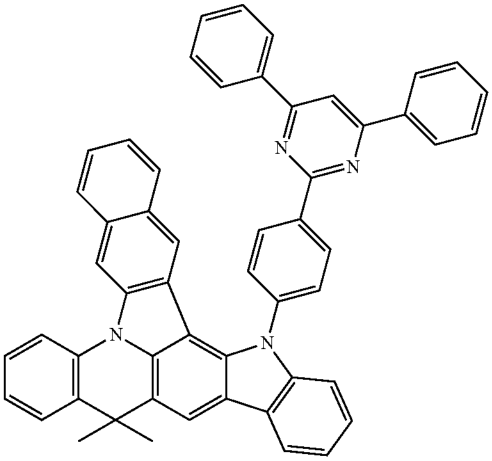
9
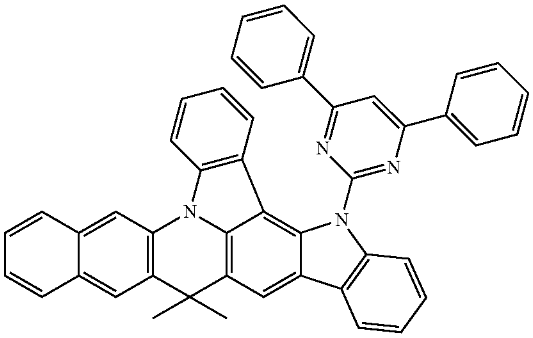

-continued

10

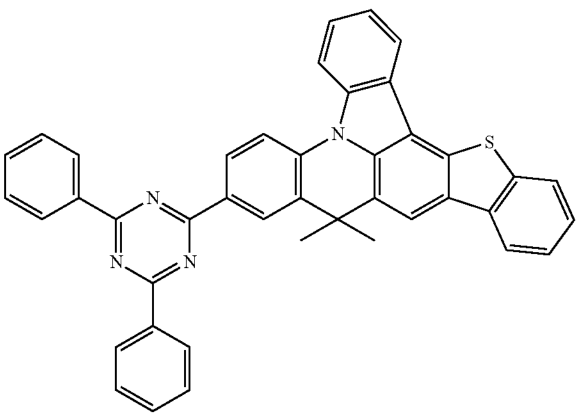

11

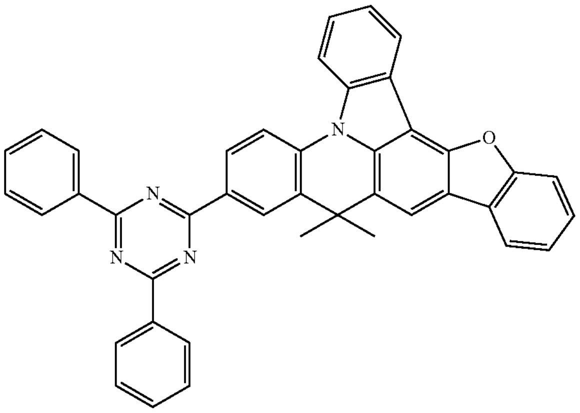

12

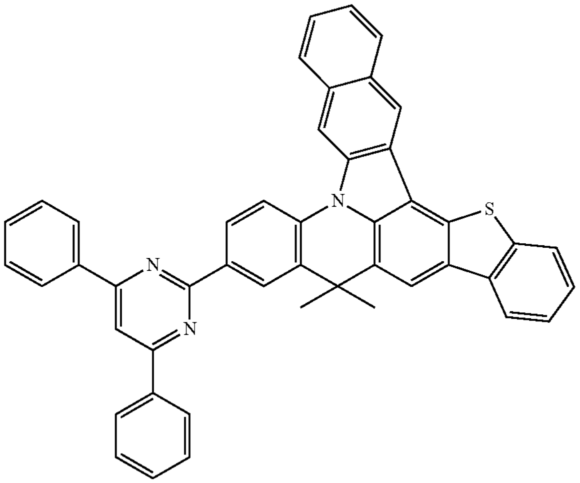

-continued

13

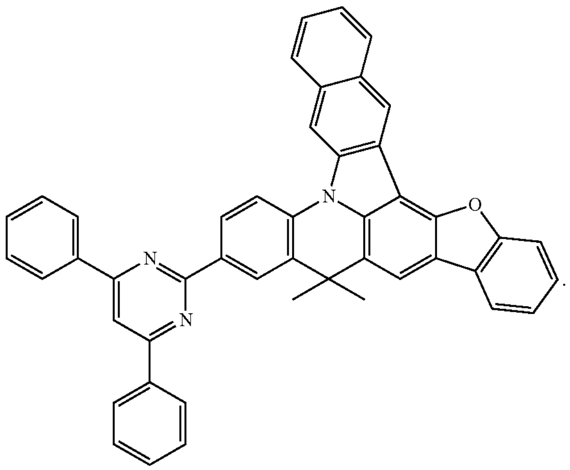

17. An organic light-emitting diode comprising:

a first electrode;

a second electrode facing the first electrode; and an organic layer between the first electrode and the second electrode and comprising an emission layer, wherein the organic layer comprises the condensed-cyclic compound according to claim 1.

18. The organic light-emitting diode of claim 17, wherein the organic layer comprises:

at least one of a hole injection layer, a hole transport layer, a functional layer having both hole injecting and hole transporting capabilities, a buffer layer or an electron blocking layer between the first electrode and the emission layer; and a hole blocking layer, an electron transport layer and an electron injection layer between the emission layer and the second electrode.

19. The organic light-emitting diode of claim 17, wherein the emission layer comprises the condensed-cyclic compound.

20. The organic light-emitting diode of claim 19, wherein the condensed-cyclic compound in the emission layer is a host, and the emission layer further comprises a dopant.

21. A condensed-cyclic compound represented by Formula 1:

Formula 1

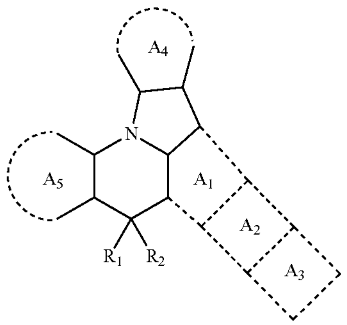

Formula 2

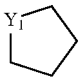

wherein:

ring $A_1$, ring $A_2$, and ring $A_3$ are condensed with each other;

ring $A_2$ is represented by Formula 2, wherein Y1 is N-$(L_1)_{aa}$-$(R_{11})_{ab}$;

ring $A_1$, ring $A_3$, ring $A_4$, and ring $A_5$ are each independently a substituted or unsubstituted benzene ring or a substituted or unsubstituted naphthalene ring, and at least one of ring $A_4$ or ring $A_5$ is a substituted benzene ring or a substituted or unsubstituted naphthalene ring;

$R_1$ and $R_2$ are each independently a hydrogen, a deuterium, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_3$-$C_{60}$ cycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group, wherein $R_1$ and $R_2$ are non-ring forming substituents which are not linked to each other and do not form a ring;

$L_1$ is a substituted or unsubstituted $C_6$-$C_{60}$ arylene group or a substituted or unsubstituted $C_2$-$C_{60}$ heteroarylene group;

aa is an integer of 0 to 5;

$R_{11}$ is a substituted or unsubstituted 5-membered hetero ring, a substituted or unsubstituted 6-membered hetero ring, a substituted or unsubstituted 9-membered hetero ring, or a substituted or unsubstituted 10-membered hetero ring in which at least one ring-forming atom is nitrogen (N); and ab is an integer of 1 to 10.

* * * * *